US011521157B2

(12) United States Patent
Blackburn et al.

(10) Patent No.: US 11,521,157 B2
(45) Date of Patent: *Dec. 6, 2022

(54) SYSTEM FOR VERIFICATION AND MANAGEMENT OF PAIRED ASSETS RELATED APPLICATIONS

(71) Applicant: Scientia Potentia Est., LLC., Charleston, SC (US)

(72) Inventors: Jeremy Blackburn, Charleston, SC (US); Justin Southward, Charleston, SC (US); W. Kurt Taylor, N. Charleston, SC (US); Karl David, Charleston, SC (US); Austi Critchfield, Clearwater, FL (US); Michael Lu, N. Charleston, SC (US); Tim McVicker, Charleston, SC (US)

(73) Assignee: Scientia Potentia Est II, LLC, Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/128,084

(22) Filed: Dec. 19, 2020

(65) Prior Publication Data

US 2021/0110342 A1   Apr. 15, 2021

Related U.S. Application Data

(63) Continuation-in-part of application No. 16/997,840, filed on Aug. 19, 2020, which is a
(Continued)

(51) Int. Cl.
*G06Q 10/08* (2012.01)
*G06F 21/64* (2013.01)

(52) U.S. Cl.
CPC .............. *G06Q 10/0833* (2013.01)

(58) Field of Classification Search
CPC ............. G06Q 10/0833; G06Q 10/103; G06Q 10/0875; G06Q 10/1057; G06Q 10/109;
(Continued)

(56) References Cited

U.S. PATENT DOCUMENTS

| 1,059,298 | A  | 4/1913 | Hoyne |
| 6,681,990 | B2 | 1/2004 | Vogler et al. |

(Continued)

FOREIGN PATENT DOCUMENTS

| EP | 3617824 A1 | 4/2020 |
| WO | 2018163044 | 9/2018 |
| WO | 2018177568 | 10/2018 |

OTHER PUBLICATIONS

Hughes, Dave, The Impact of Blockchain Technology on the Construction Industry:, Feb. 19, 2017; medium.com, 8 pages. (Year: 2017).

(Continued)

*Primary Examiner* — Garcia Ade
(74) *Attorney, Agent, or Firm* — Kim and Lahey Law Firm, LLC; Douglas W. Kim

(57) ABSTRACT

A computerized system for verifiable pairing physical assets with digital representations comprising a set of non-transitory computer readable instructions for retrieving a design record having a material list, retrieving a supplier record according to the design record and according to a first verification, retrieving a shipping record according to the supplier record and according to a second verification, and creating a material receipt record including a third verification representing that the material is received at the location and is the same material that was designated in the designer, provided by the supplier, received by the shipper and delivered to the location.

23 Claims, 38 Drawing Sheets

Related U.S. Application Data continuation-in-part of application No. 16/994,585, filed on Aug. 15, 2020, which is a continuation-in-part of application No. 16/991,916, filed on Aug. 12, 2020, which is a continuation-in-part of application No. 16/876,080, filed on May 17, 2020, which is a continuation-in-part of application No. 16/810,782, filed on Mar. 5, 2020, which is a continuation-in-part of application No. 16/510,642, filed on Jul. 12, 2019, and a continuation-in-part of application No. 16/510,634, filed on Jul. 12, 2019, now Pat. No. 10,713,737, which is a continuation-in-part of application No. 16/452,076, filed on Jun. 25, 2019, now Pat. No. 10,713,737, said application No. 16/510,642 is a continuation-in-part of application No. 16/452,076, filed on Jun. 25, 2019, said application No. 16/810,782 is a continuation-in-part of application No. 16/452,076, filed on Jun. 25, 2019.

(58) Field of Classification Search
CPC ...... G06Q 40/08; G06Q 40/125; G06Q 50/08; G06Q 50/265; Y02P 90/90; G06K 9/00771; G06K 9/00288; G16H 40/20; H04N 5/77; H04N 9/8205; G06V 20/52; G06V 40/172
USPC .......................................................... 705/333
See application file for complete search history.

(56) References Cited

U.S. PATENT DOCUMENTS

| | | | |
|---|---|---|---|
| 7,031,930 B2 | 4/2006 | Freeman et al. |
| 7,330,821 B2 | 2/2008 | Wares |
| 7,508,973 B2 | 3/2009 | Okabe et al. |
| 7,546,576 B2 | 6/2009 | Egli |
| 7,898,403 B2 | 3/2011 | Ritter et al. |
| 8,004,397 B2 | 8/2011 | Forrest et al. |
| 8,103,596 B1 | 1/2012 | McFarlin et al. |
| 8,321,302 B2 | 11/2012 | Bauer et al. |
| 8,428,904 B2 | 4/2013 | Vock et al. |
| 8,521,620 B2 | 8/2013 | Livingston et al. |
| 9,135,787 B1 | 9/2015 | Russell et al. |
| 9,727,923 B2 | 8/2017 | Teh et al. |
| 10,121,112 B1 | 11/2018 | Vasquez, Jr. et al. |
| 10,338,913 B2 * | 7/2019 | Franchitti ........... G06F 16/9538 |
| 2006/0137015 A1 | 6/2006 | Fahrny et al. |
| 2007/0220342 A1 | 9/2007 | Vieira et al. |
| 2010/0058364 A1 | 3/2010 | Sherrill et al. |
| 2011/0060659 A1 | 3/2011 | King et al. |
| 2017/0031676 A1 * | 2/2017 | Cecchetti ................ G06F 21/64 |
| 2017/0286572 A1 | 10/2017 | Hershey et al. |
| 2018/0210436 A1 | 7/2018 | Burd et al. |
| 2019/0251575 A1 | 8/2019 | Berti et al. |
| 2019/0287181 A1 | 9/2019 | Lekas |
| 2019/0317935 A1 | 10/2019 | Berti et al. |
| 2019/0333169 A1 | 10/2019 | Povar et al. |
| 2019/0377904 A1 | 12/2019 | Sinha et al. |
| 2020/0034766 A1 | 1/2020 | Borges |

OTHER PUBLICATIONS

Penzes, Balint, "Blockchain Technology in the Construction Industry: Digital Transformation for High Productivity", Dec. 2018; Ice: Institution of Civil Engineers, 52 pages. (Year: 2018).

Miskins, Carlos, "Digitizing the Construction Sector Using Digital Twin Technology Simulations", Dec. 2018, https://www.challenge.org/insights/digital-twin-in-construction/, 8 Pages.

Verma, Urvashi, "What Are Digital Twins in Smart Buildings?", Oct. 31, 2018, https://inbuildingtech.com/bms/digital-twin-commercial-office-building/, 9 Pages.

Ghanem, Amine et al., "A Case Study for Improving Construction Project Management", 51st ASC Annual International Conference Proceedings, 9 pages (Year: 2015).

Barista, David, "'BIM for all' platform pays off for contractor", https://www.bdcnetwork.com/bim-all-platform-pays-contractor, Aug. 13, 2020; 12 pages.

AZ Big Media, "Technology Shakes Up How Projects Planned, Scheduled and Built," https://azbigmedia.com/business/special-seriers/technology-shakes-projects-planned-scheduled-and-built, Aug. 13, 2020, 13 pages.

* cited by examiner

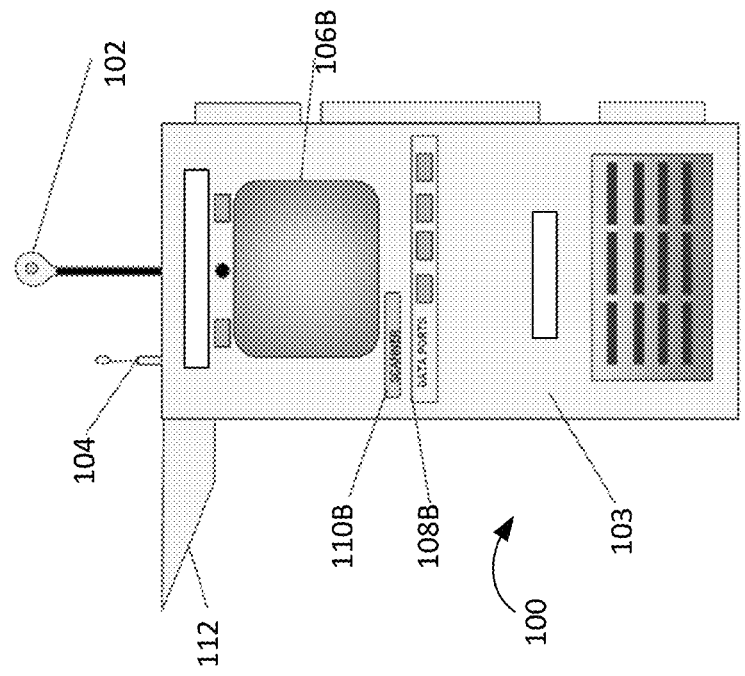
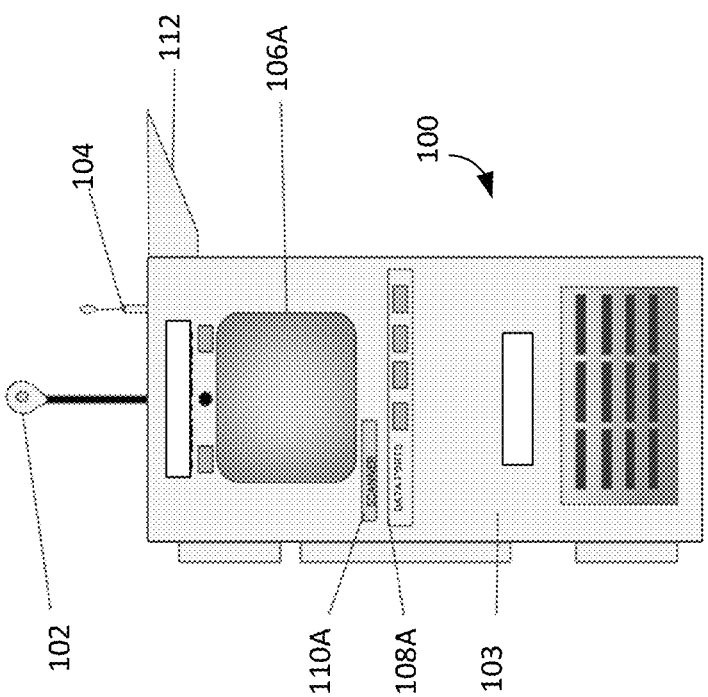
Fig. 1A
Fig. 1B

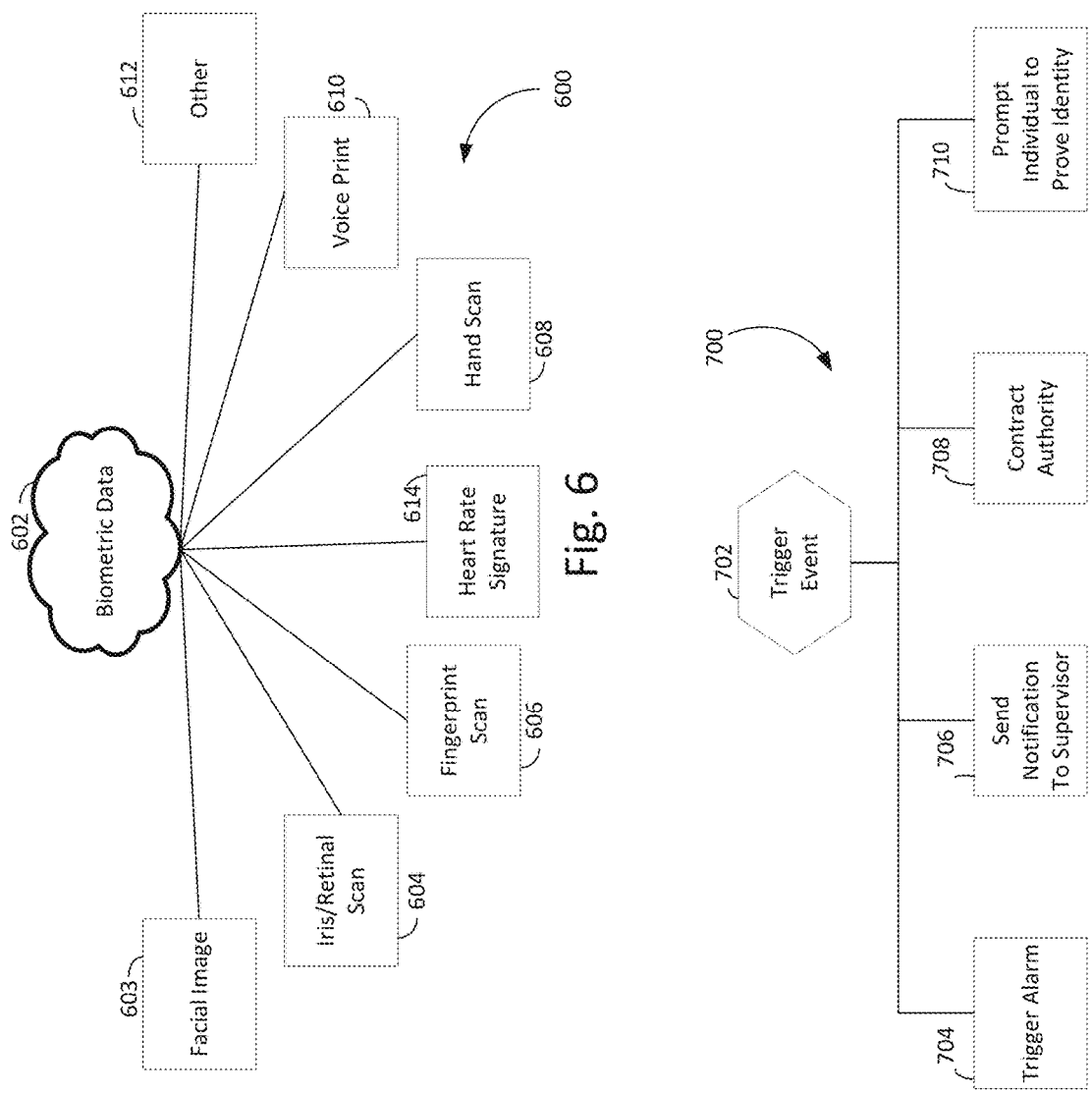

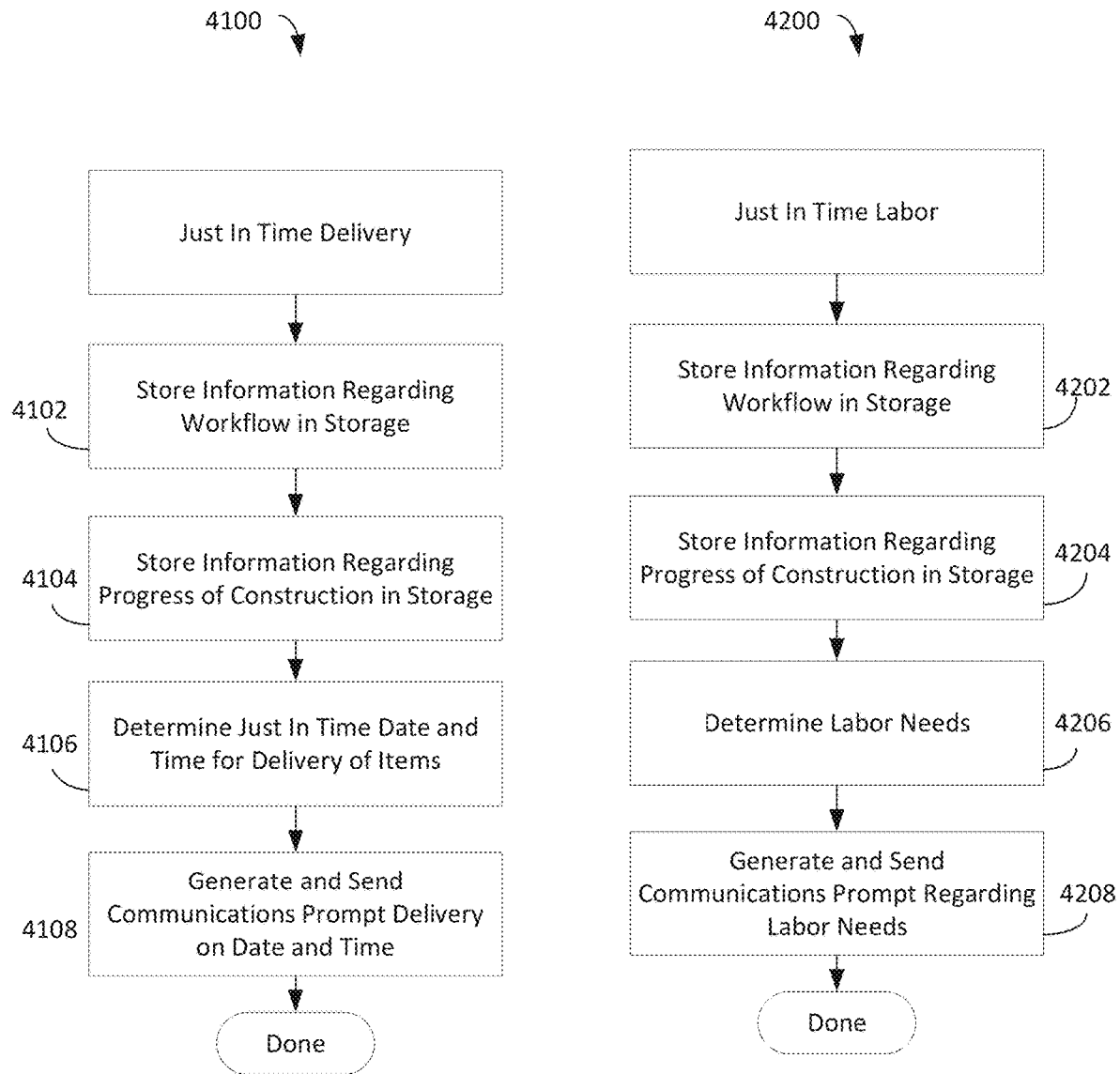

SYSTEM FOR VERIFICATION AND MANAGEMENT OF PAIRED ASSETS

RELATED APPLICATIONS

This application is a continuation in part of U.S. application Ser. No. 16/997,840 filed Aug. 19, 2020, which is a continuation in part of U.S. patent application Ser. No. 16/994,585 filed Aug. 15, 2020 entitled "System For Management Of Verification Of Project Commencement and Completion", which in turn is a continuation in part of U.S. patent application Ser. No. 16/991,916 entitled "System For Management Of Warranty Information For Projects And Materials", filed on Aug. 12, 2020 which in turn is a continuation in part of U.S. patent application Ser. No. 16/876,080 entitled "Digital Asset System For Management Of Projects And Materials", filed May 17, 2020 which in turn is a continuation in part of U.S. patent application Ser. No. 16/810,782, entitled "System For Management And Verification of Code Compliance", filed on Mar. 5, 2020 which in turn is a continuation in part of U.S. patent application Ser. No. 16/410,634, entitled "Use of A Persistent Storage Reference Construction Metadata and to Use Smart Contracts for a Project or process", filed on Jul. 12, 2019, U.S. patent application Ser. No. 16/510,642 entitled "Use of a Blockchain-Based Distributed Ledger and Smart Contracts for a Project or process", filed on Jul. 12, 2019 both of which are continuations of U.S. patent application Ser. No. 16/452,076, entitled "Site Super System For Project locations", filed Jun. 25, 2019 which all are incorporated reference.

BACKGROUND

1) Field of The System

A system for pairing physical assets and virtual representation to verifiably link the physical asset with its virtual representation to create a undichotomized pair providing truth over trust.

2) Background

In the modern economy, there is a continuing trend for digitization. This trend includes attempts to create digital assets that attempt to represent physical assets. Through digitization, an asset can be converted into a digital representation such a digital file stored on a database. For example, a bank balance can be the digital representation of the fiat currency that is in the possession of the bank account holder. The challenge is when the asset is not fungible, such as currency, but are not easily substituted. For example, during the manufacturing of a vehicle, components for that vehicle are specific to that make, model and year and are not readily substituted between vehicles of different makes, models, and years. This can be illustrated when replacement parts are needed for the vehicle and the make, model, and year, are need for determining the proper replacement and in some cases the vehicle identification number (VIN) number itself is needed because the replacement part is unique to the that vehicle. An additional problem is created when a first replacement is placed on a vehicle and a second part that cooperates with the first part needs to be replaced. The second replacement part, while compatible with the original part, may not be compatible with the first replacement part. Currently, there is no digital system that allows for the tracking of physical assets and the processes that use the physical asset (e.g., installation) using a virtual representation of the physical asset.

In the financial industry, digitization began with electronic information representing the dollar value of an account. While the value of the account was not tied to a physical dollar, it did represent the number of dollars in the account. As the financial industry progressed, the electronic current itself became the asset as discussed in U.S. Pat. No. 9,135,787, this patent discloses a Bitcoin kiosk/ATM that facilitates the buying or selling of Bitcoin. For example, Bitcoin can be traded so that Bitcoin is in and of itself the commodity and does not necessarily represent a fiat currency.

This type of digitization where the digital information represents the asset that is to be distinguished with electronic scanning of physical assets. For example, digital information representing US currency is quite different than physically scanning US currency. Despite the illegality of this example, the digital scan of US currency and the US currency itself are not equivalent. The US currency can be spent without reference or modification of the digital scan and the digital scan can be manipulated without reference or modifications to the US currency. The physical and the digital are not verifiably paired. This distinction makes the digitization of physical assets challenging as the digital asset and the virtual representation are not functional equivalents and therefore are not verifiably paired. While it is a fairly simple task to put a digital item on digital persistent storage, such as blockchain, it is difficult, if not impossible, to put a physical item on digital media.

In the current systems, especially with digital currencies, there is a significant risk of scams, frauds, and irregularities with the assets. Potential risks in this area include Ponzi schemes, fake initial coin offering and fraudulent exchanges. It would be advantageous to have a system that can reduce or eliminate the risks associated with cryptocurrency as well as digital representation of physical assets.

A significant disadvantage with current systems is the potential for rehypothecation. First, hypothecation means pleasing an asset as collateral for a debt so that in the event of a default, the asset can be seized (e.g., foreclosure or repossession) to satisfy the default at least partially on the debt. Rehypothecation is when the creditor uses the collateral from a first loan (e.g., original loan) and uses it as collateral for a second loan. Rehypothecation increases uncertainty and adds risk in that actual ownership, lien, or collateral can become uncertain.

For many industries, there should be a systematic and logical workflow that increases the success of any project, manufacturing, construction, providing of services, and the like. For example, when constructing a residential home, the foundation is provided prior to the roof installation. The design record can include make, model, serial number, or other identification of for every component in the task, project, or process. The design record may include workers qualified to perform and complete the work, who should inspect the work and how the project should be insured and funded.

This process can require that the designer specify materials, suppliers that supply the materials, that workers have a specific set of credentials, licenses or experience, and inspectors verify the delivery and performance of tasks during the project. When designing a project such as manufacturing, repairs, construction, maintenance, testing, and the like, designers can include a material list (e.g. bill of materials, parts list, packing list) representing the specified materials to be used for the project. For the project to be successful, the specified materials should be delivered to the project site and verified as correct. The workers should be properly trained and equipped according to the materials and associated tasks. Third-party inspections should be performed for each step in the process to verify compliance with regulations, specifications, instructions and the like.

In current workflow and material tracking processes, one disadvantage is the lack of accountability, verification and reliability of information related to the materials used, tasks performed and workers. The inability to verify correct materials, installation, workers, coworkers' experience and credentials and other factors can result in loss, mistakes, injury, increased insurance claims and increased premiums. This weakness in the current process and system negatively impact the process, risks, and costs in general. While there have been some attempts to add item information to a physical material, such as U.S. Pat. No. 8,321,302, these attempts have focused on tracking inventory levels and do not include verifiably pairing a physical material with a virtual representation that can be tracked throughout a process. Further, these prior attempts focus on a single location and do not consider the fact that the design, material, and project can initially be at separate locations. This disadvantage can be seen in U.S. Pat. No. 8,521,620 which specifically states that if a RFID tag is lost or damaged, the system allows a user to enter an item number or style and tags of similar items are displayed, a new tag is generated and associated with the item having the lost or damaged tag. Once the RFID tag is lost or damaged, the physical asset is no longer paired. While this system specifically allows for the replacement of RFID tags on the same item, it lacks the ability to verifiably pair the new tag with the physical asset.

The disadvantages of current systems are caused in part due to the lack of pairing the physical asset with the virtual representation to determine that the materials requested, and the materials delivered and used are properly paired. Attempts to provide for inspections that the proper materials designated at the design were actually delivered and used or installed at a target location. United States Patent Application Publication 2019/0287181 discloses a virtual home inspection but specifically states that the inspector does not have to be tied to the physical location where the home is to be inspected. Without the ability to verify that the materials inspected are physically located at the project locations, a virtual inspection has all the disadvantages of mistakes, inaccuracies, and even dishonestly with designated materials not arriving and being used or installed at the home.

There is also a need to verify that the workers preforming tasks associated with the materials are properly licensed, experienced, and authorized to perform these tasks. Laws and regulations require that many tasks performed by workers must be performed by a properly licensed worker. Licensing is intended to ensure that only competent and ethical individuals practice in an occupation and include professions such as land surveyors, cosmetologists, nurses, building contractors, engineers, and electricians. Failure to use licensed workers can lead to poor performance, low quality, fines, legal liability and even criminal liability. There have been attempts to manage worker licensing such as shown in U.S. Pat. No. 8,103,596 but such attempts fail to determine if the task actually being performed by the worker is one that the worker is licensed to perform. These prior attempts focus on maintaining licensing requirements, but do not verify that the worker is actually licensed to perform that task.

There is also a need to verify that the tasks being performed by the worker using verified materials is in compliance with the applicable specifications. Specifications in some processes can include the specification of a manufacturer or project site, the performance criteria of the materials, worker experience requirements and the quality of the systems and products, which standards are applicable and how they should be executed, who should execute them and even the specific model of a product to use. Specifications can include materials selected at the design phase as well as handling and installation specifications associated with materials from the supplier. It would be advantageous to have a system that verified proper materials, authorized workers are used and proper installation procedures under the proper environmental conditions are performed and pairing these items and tasks with a virtual representation. It would be advantageous to have a system that reduced or eliminate the risk of a substitute, lesser quality or other non-designated or approved material being used. It would be advantageous for a system that prevented or reduced the risk of unlicensed or unauthorized workers, failures to comply with material specifications and failure to follow installation or user instructions. It would be advantageous to have a system that provides for third party or automated independent verification to reduce false or misleading information, incorrect signoffs on a project, incorrect inspections and improper material and tasks in general.

The use of inspectors can assist with reducing the risk of improper or unauthorized workers, materials, tasks, process, and specifications. One disadvantage of an inspection is that it occurs at a point in time and cannot verify proper workers, materials, tasks and use and installation specifications. For example, in the construction of vehicles, electronics, resident and commercial buildings and other articles, wiring, to be properly inspected, needs to be reviewed before it is obscured. For example, during the residential construction project, if the interior walls are installed, the material and installation behind the walls cannot be inspected. There have been attempts to provide for automated inspection such as U.S. Pat. No. 7,508,973 which discloses method of inspecting detects includes assigning a plurality of sets of image acquisition conditions, executing inspection using each of the sets of conditions, classifying all detected defects into real defects and false defects by use of an automatic defect classification function, and selecting, from the plurality of sets of conditions, a set of conditions ideal for detection. However, this attempt does not allow the inspector to verify that the material used and processed complies with the design and specification using a paired virtual representation.

Another disadvantage with the current system is that the data resulting from the materials, workers, tasks, and the like are not easily accessible by all stakeholders. For example, inspections can be a physical form or captured with a proprietary inspection system, Inspection Support Network (r). The data is stored and maintained by the system provider so that data security is dependent upon the accuracy of the input and the system provider itself. It would be advantageous to have a permanent verified record of a design, materials, delivery, workers, tasks, installation, and inspections paired with physical materials and activities that can be referenced by others before, during and after commencement of a project or process.

There have been some attempts to improve tracking of articles such as shown in U.S. Pat. No. 7,898,403 that are directed to a method and system for detecting construction equipment process failures. A database is populated from information from a third-party source and a process failure report is provided for processes that are outside a norm assigned to the construction equipment asset. U.S. Pat. No. 7,031,930 is directed to a method and system for managing complex projects or processes by monitoring subcontractors in real time, against a system after commencement of the project. U.S. Pat. No. 8,004,397 is directed to a mountable reporting source comprising a controller coupled with an interrogating component configured for automatically receiving an identifier which is unique to an asset having a position determining component. Again, this is directed to the construction process itself, not management and verification of code compliance. U.S. Pat. No. 8,428,904 discloses product integrity tracking system, shipping label and associated method. This patent is directed to label body for attaching to a product to be shipped or to packaging containing the product. It does not disclose a verifiable pairing between the physical asset and the virtual representation during the project's lifetime.

Further, prior systems do not account for delivery of materials in undesirable weather conditions. Materials that are exposed to undesirable weather can damage or destroy the material making it unfit for use. It would be advantageous for a system to determine the environment where materials are delivered and installed to prevent damage to the material and therefore the project. For example, when moisture gets trapped behind the building material stucco, the moisture can produce "stucco tears," which result in discoloration of the stucco beneath windows or cause the formation of mold and mildew, which can escalate into an infestation of black mold. Manufacturers have certain requirements for stucco and its installation and can require certain humidity ranges and temperature ranges. If metal, especially carbon steel, is exposed to moisture, chloride, and other environmental materials, the steel can corrode such as when metal like steel, copper, magnesium, aluminum is exposed to free flowing air and moisture.

It would be an advantage to have a system that can pair physical assets with virtual representation so that compliance with the design, process or procedure, and specifications are verified and stored as a persistent record.

It would be advantageous to have a system that provides for multi-party verification of the pairing of a physical asset with a virtual representation for tracking of the physical asset and the associated project.

It would be advantageous to have a system that provides for a verified trustworthy association between physical material and virtual representations.

SUMMARY OF THE SYSTEM

In accordance with an exemplary embodiment, a computerized system for verifiably pairing a physical asset with a digital representation of providing and can include a computer system disposed at a location and in communications with a persistent storage; a set of non-transitory computer readable instructions included in the computer system adapted for: retrieving, from the persistent storage, a design record created by a designer and having a material list including a material, retrieving, from the persistent storage, a supplier record created by a supplier according to the design record and according to a first verification representing receipt of the material by the supplier paired with a first virtual representation stored on the persistent storage, retrieving, from the persistent storage, a shipping record created by a shipper according to the supplier record created by a supplier and according to a second verification representing that the material is provided to the shipper and paired with a second virtual representation stored on the persistent storage, and creating a material receipt record including a third verification representing that the material is received at the location and is the same material that was designated in the design, provided by the supplier, received by the shipper, and delivered to the location.

The computerized system can include a location marker associated with the location; and can be uniquely paired with the location using the location marker. The system can include a sensor in communications with the computer system wherein the first verification utilizes the sensor and location marker. The supplier record can be created according to a physical verification of a first tag affixed to the material and the location marker. The second verification can be a verification that a second tag is affixed to the material. The second verification can include verification that a second tag is affixed to the material using a sensor in communications with the computer system. The supplier record can be created according to a physical verification of a first tag affixed to the material. The supplier record can include metadata taken from the group consisting of date, time, location, worker, environmental condition, and any combination thereof.

The shipping record can be created according to a physical verification performed by an individual that material is consistent with the second virtual representation.

The location can be the location associated with an entity taken from the group consisting of an assembler, a retailer, a wholesaler, an installer, a builder, a manufacturer, a service provider, a customer, and any combination thereof.

The distribution record representing that the material received at the location is the same material that was designated in the designer, provided by the supplier, retrieved from the supplier by the shipper, delivered to the location by the shipper and delivered to a distributor. A customer record can represent that the material received at the location is the same material that was designated in the designer, provided by the supplier, retrieve from the supplier by the shipper, delivered to the distributor by the shipper and delivered to a customer.

The set of non-transitory computer readable instructions can include instructions for creating a repair request, storing the repair request on the persistent storage, and creating a repair record according to a replacement part and associating the replacement part with a replacement virtual representation and storing the repair record on the persistent storage.

The location can be a first location. the shipping record can be a first shipping record, the shipper is a first shipper; and the set of non-transitory computer readable instructions include instructions for creating a second shipping record requesting shipping of the assemble to a second location wherein the second shipping record includes a fourth verification. The system or a portion can be contained in a kiosk that can be affixed to the location.

The metadata can be taken from the group consisting of date, time, location, supplier, environmental condition, and any combination thereof.

BRIEF DESCRIPTION OF THE DRAWINGS

FIGS. 1A-1F shows various side views of aspects of the system.

FIG. 6 shows various types of biometric data that may be gathered.

FIG. 7 shows types of events that may be triggered.

FIGS. 13-16B shows flowchart having steps that may be performed.

FIGS. 34-42 shows flowcharts of steps performed by the system.

DETAILED DESCRIPTION

Figure 1D:
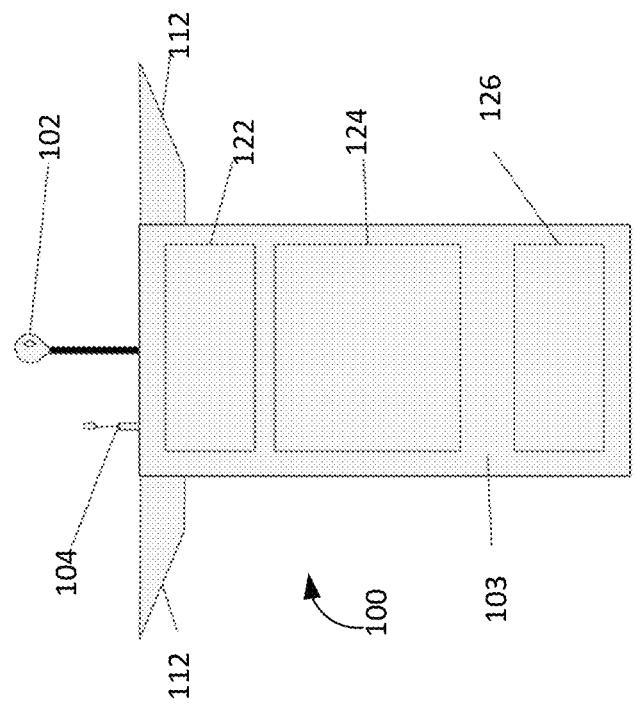

The present system provides for real time verified pairing of a physical item with a virtual representation. The server can include a set of server computer readable instructions configured to receive a design that can include a material requirement record from a design computing device in communications with the server. This material requirements record can include such fields as make, model, quantity, warrant inflation, hazardous information, safety data, the class, type or other identification of the material, one or more vendors, the cost, installation instructions, material specifications, assembly, other materials that can be included and other information. The material requirements record may contain a complete itemization of materials needed for a task, project, process or assembly. The material requirements record may be updated as actual materials arrive to the site and have serial numbers, bar codes, QR codes, RFID values, beacons, lots, sizes, or other components or material identification added or associated with the material requirement record.

For example, the material can be a vehicle part that can include information about the part as well as information as the vehicle that the part is designed to fit. The vehicle can be the assembly having its own location marker. The design can include design requirements such as regulatory requirements associated with the material and the assembly. The designer can create one or more material requirement records representing one or more materials to be used for a process or task that can involve the material and the assembly. Design and its associated records can be stored on a persistent storage platform that can be accessed by multiple parties. The persistent storage can be disposed at the location of the process, task or assembly or can be remote from such location.

The system can also provide the design, including the material requirement record to a supply computer device informing a third-party supplier, distributor or reseller to deliver the materials to the project location. The supplier can review the design and determine if the materials specified are available, in stock, consistent with each other and the assembly or otherwise determine information concerning the ability to provide the specified materials. The supplier can receive the design directly from the system or can retrieve the design information from the persistent storage. The supply company can send proposed modifications to the design computer system which can be accepted or rejected by the designer and the design information modified accordingly. Using information from a supplier, the material requirement record can include a virtual representation of the material associated with the physical material. In one embodiment, the materials are specified by class, type, product code, product number of other identifying information and virtual representation so that the material requirement record includes the material paired with the virtual representation which is verified by the designer. This verification is independent of the other verifications described herein.

Design information can include a building information model for a construction project, a listing of repair parts for a vehicle repair service, a listing of material for a manufacturing project and other applications where components are selected, ordered, shipped, and used to create an assembly. Once the design information is finalized, the supplier selects the items for transport and creates a supply record representing the material to be provided to a project location. The supply record can include the material information and the virtual representation. The supply company can inspect the material to ensure that the material is properly associated with the virtual representation to create a verified pairing of the material with the virtual representation. The supplier verification can be independent of other verifications as described herein. The suppler record, that can include the verified paired information, can be stored on the persistent storage.

The project location can be a manufacturing place, construction site, business providing services (e.g., vehicle repair service) or other location where the materials will be used to create, maintain, or repair an assembly. When the material is selected for transport by the supplier, a shipping company can be sent a shipping order representing the materials to be transported. The shipping order can include a listing of the materials and the verifiably paired virtual information. The shipping company can be provided shipping information from the designer, supplier or other company that can facilitate the transaction (e.g. broker, distributer, reseller). The shipping order can be provided directly to the shipping company or can be retrieved from the persistent storage. Once the shipping company receives the shipping order, it can travel to the material location and determine if the list of materials in the shipping order match the physical materials at the material location. A shipping pickup record can be created representing that the shipping company received the materials and that the material picked matches the shipping order. This verification is independent of the other verifications described herein.

Once that material is delivered to the project locations, the shipping company can unload the material and verify that the material that was unloaded was the same material included in the shipping order. The shipping company can create a shipping delivery record representing what materials were delivered and that the materials match the shipping order. The shipping record can include the environmental conditions when the materials were delivered, delivery notes and the like. The shipping delivery record can be stored on the persistent storage. The assemblies can be an individual or organization that preformed process or tasks associated with the assembly. The assembler can review the materials delivered and verify that the delivered materials match the design information, material requirement record, supply record, shipping order, shipping pickup record, shipping delivery record of any combination.

Once the materials are received by the assembler, the system can notify workers or supervisors that the materials are ready for use. The worker can be verified by the system and a worker verification record which is created and stored on the persistent storage. The system can utilize biometrics or other systems as described herein for verification of actual workers on the project location to correspond with licenses, work certifications, experience, and authorizations as well as for verified payroll and insurance coverage. The system can identify workers and other individuals entering or leaving the project location and store this information on the persistent storage. The verification can be through biometric identification devices such as a camera or other image capture device, facial recognition, voice recognition, retinal scans, fingerprint scanners, hand scanners, and other biometric devices. In one embodiment, the computing logic may allow authorized individuals to manually enter the presence of another authorized individual, including on the controller at the project location or through a remote device that can be determined to be at the project location, within a boundary associated with the project location, in proximity to the system. In one embodiment, individuals may be verified and paired with a virtual representation using two-factor authentication.

The worker can be provided with material installation information and specifications or other design requirements that can be represented by a task record. The task record can be stored on the persistent storage. Once installed the system can verify that the materials were installed according to the task record, create a task verification record and store the task verification record on the persistent storage. The task verification record represents that a task associated with the material was properly completed. The task record can represent that the task was performed by proper worker, with the proper materials, in compliance with a regulatory code, in compliance with specifications, passed one or more inspections.

Prior to, during and after a task is completed, an inspection can be performed that can include a pre-task inspection, task inspection, post task inspection and any combination. A pre-task inspection, task inspection, and post task inspection record can be created so that the three records can be stored on the persistent storage. The task record can include information that the inspection resulted in passing, passing with deficiencies, and failing. In the event that the inspection fails, the assemblies can be given the opportunity to remedy the failure and the inspection process can be performed again. The assembler can also determine if, while the task passed the inspection, the deficiencies should be remedied.

The system can be uniquely associated with the assembly location. A location marker can be affixed to the project location and uniquely identify the project location. The location marker can be read by the system so that the system can determine its location. Third parties can read the location marker to determine the location. For example, the shipping company can arrive at the project location, read the location marker, and associate the location marker with the delivery of materials. In one embodiment, the assembler can receive a shipping identifier associated with the delivery, such as a truck, trailer, pallet, or other container so that the materials are known to be received at the project location. Other parties can also access the location marker to verify that the third party is at the project location.

The system can be contained in a housing such as a kiosk and can be physically associated with the project location. The project location can be defined by a boundary representing the perimeter of the physical location. The system can include a sensor and reader which can be selected from the group consisting of: radio frequency identification (RFID) detector, ultra-high frequency (UHF) detector, a bar code scanner, a QR code scanner, near frequency communication (NFC) device; Bluetooth beacons, an optical character recognition (OCR) device and any combination thereof. An environmental sensor, such as a weather sensor or weather station, can be in communications with the or included in the housing and configured to record the weather and other environmental conditions at the project location and at different times during the project.

The system may record the date and time of events such as the arrival and departure of materials, individuals, workers, supplies, third parties, inspections, and the like to and from the project location, the date and time associated with environmental conditions including weather. The environmental conditions can be used to modify the schedule for workers so that workers are not working during inclement weather, tasks are not preformed outside specified environmental conditions, and materials are delivered and installed during specified environmental conditions. Additionally, the system may prevent tasks from being performed if the tasks would violate manufacturer, supplier, integrator, customer, or other guidelines, specifications or instructions for use or installation or materials of the assembly. Recording environmental information, including weather, at the project location allows for autonomous confirmation of environmental conditions that do not rely solely on third party sources or sources that are general or distant from the project location.

The system may also determine if an unidentified individual attempts to enter the project location, the system may take the appropriate responses, such as sending notifications, triggering alarms, and/or contacting law enforcement authorities or security. The decision as to the appropriate response may be determined by, the date, the time, current weather conditions, authorizations, project or process status, or related factors.

The system may also control access to tools, equipment, materials, and areas of the project location. As to tools, equipment and materials, the system may confirm the identity of an individual and grant access to certain tools and equipment using smart locks and/or other technology. The system may limit the dates and duration of access to the tools/equipment such that the tools/equipment must be returned within the specified date/time window. An onsite scanner or reader may be used to identify tools, equipment, materials, and areas of the project location such as by using barcode, RFID, beacons or other identifying information to track these items, associate them with a worker or area of the project location.

The smart locks may also be used to limit access to certain portions of the project or project location. An individual's right to a specific asset (e.g., tool, material, location, etc.) of the project location may be dictated by permissions that are stored through each party involved in the construction process. This may eliminate keyed entry during the process and provide further verifications of individual or group access.

The individuals on the project location may be prompted to wear certain wearables that provide useful information to the system. For instance, individuals may be prompted to wear location tracking devices, such as GPS devices, Bluetooth, radio frequency identification (RFID) devices, ultra-high frequency (UHF) and/or beacon-based devices. The use of the wearables helps to perform geofencing within the project location. The location tracking provided by the wearable helps the system to monitor the location of individuals on the project location on an ongoing basis. The permissions may define what portions of the project location an individual may access. Ongoing monitoring may indicate that an individual is attempting to enter a location where the individual is not permitted. This may trigger a response as described herein. A signal may be sent to the vest or wearable to trigger a visual or audio cue that the individual is not in a permitted area. In addition, individuals may be requested to wear wearables that track biometric information, such as heart rate, body temperature, respiration rate and blood pressure. This information may be tracked and stored on an ongoing basis. When the biometric data gathered from these wearables are outside an acceptable range, potentially indicating physical danger or injury, appropriate response actions may be taken, such as notifying the individual, notifying a supervisor, and/or contacting medical personnel. Collected data may be used to verify a multitude of factors such as reported accidents, incidents of theft, hours worked, and the like. In the event that an accident occurs, the system can record information about the accident such as the worker involved, the equipment being used, physical location, other worker(s) in the area, video capture from cameras in the area, materials involved, and/or tools and equipment involved and then it can record the information for reporting and future study.

The system may track the movement of materials, tools, and equipment at the project location or to and from the project location. Scanning technology such as RFID readers, UHF readers and/or the like may be utilized to assist the location tracking for tools, equipment, materials and even workers. The tracking of materials helps reduce the risk of loss, theft, mis-delivery, and the like. For example, the tracking solution may indicate instances of possible theft, such as when the materials are leaving the project location when the removal of the materials is not proper.

The system may allow for the establishment of one or more geofenced zone that can be associated with delivery areas, worker entrance exit areas, task areas, storage areas, assembly areas, distribution areas and any combination thereof. These areas could be monitored and established with access allowances or restrictions to control movement of material, individuals and equipment to assist with the prevention of loss, mistakes, inefficiencies, and damage. The system can assist with verification that materials stored-on locations are consistent with specifications associated with the materials.

The system may control access to power by individuals at the project location. The housing may provide several power outlets or control power outlets to grant access to power as needed or warranted. Different levels of voltage may be provided as required and the system can determine, track and record power usage. The system can also restrict power usage during predetermined events including warranty confirmatory, safety situations, specifications, environmental conditions, and any combination thereof. Access to power can be controlled by the system or the power can include an intermediate power controller that can be controlled by the system.

The system, including a controller, may also interface with individuals to allow for the entry of notes and related details of a material, task, inspection, environmental condition worker, other task, process of individual or any combination thereof. For example, the system may allow an inspector to capture images of notes, forms, documents, labels, and the like using various readers, sensors, and input devices.

Exemplary embodiments may reference a record of a project or process on persistent storage. The process of maintaining the record for the project or process may begin at the design phase such as with a Building Information Model used in the construction industry. The design can contain 2D, 3D and 4D plans for the design.

The exemplary embodiments may receive or determine a task, project, or process schedule that contains project or process details and sequencing, including the specification of dependencies.

Smart contracts may be provided that use the persistent storage for each event of the project or process schedule and can execute upon satisfaction of terms of the event. For example, when material article is delivered from a shipper to a supplier and a verification of the material with is virtual representation occurs, this event can trigger a smart contact that instates payment to the shipper.

Upon completion of the assembly, an assembly record can be created and stored that includes the actual "as built" information including the materials used, material information from design to completion, each task preformed each worker and what task was performed and when, environmental conditions, inspection information insurance, funding, financial transactions, and verifications for each step.

FIGS. 1A-1D illustrate an example of a system 100 in a housing that can be uniquely associated with a project location in an exemplary embodiment. The housing can be a housing that can be affixed to the project location. In FIGS. 1A-1D, the system is implemented as a housing having a controller. The housing 103 may be located at a project location and include a controller in communications with a computer readable medium. One suitable approach is to pour a concrete slab and then position a housing on the concrete slab in a secured manner. The housing can be physically associated with the project location, virtually associated with the project location or both. A location marker can be affixed to the concrete slab or otherwise affixed at the project location. The housing can be removeable attached to the project location so that it is stationary during a first project or process but can be moved to a second project or process at a different physical location once the first project or process is completed.

The housing 103 can be physically associated with the project location, virtually associated with the project location or both. A unique location marker can be disposed at the project location to uniquely identify the project location. For examples, a transmitter such as a RFID can be associated with the project location by embedding it is a permanent fixture such as a concrete slab, foundation, structure, and the like. The system can read the information from the location marker and associate its actual location with the project location. The location marker can include an alpha, numeric or graphical information such as a number, letters, barcodes, QR code, physical or geographic coordinates (e.g., GPS coordinates), passive transmitter, active transmitter and the like. Each system can have a unique identifier and each project location can have a unique identifier.

FIG. 1A shows a first side of the system 100. The system 100 can include a camera 102 for obtaining images of materials, equipment, individuals or other items entering or leaving the project location as well as images of individuals along a perimeter. The camera 102 may capture biometric images upon which biometric recognition may be performed. Multiple cameras may be placed on or around the housing. The cameras may have biometric recognition and motion detection capabilities. System 100 may include an addition to the camera 102 or instead of the camera 102, biometric-based identification devices that may be used to confirm the identity of individuals entering, leaving or on the perimeter of the project location. The system 100 may include an antenna 104 for communicating with a network including a wireless network, Wi-Fi network, Bluetooth, quantum networks, cellular network (e.g., 4G or 5G network) and any combination. The system 100 may include a housing 103 made of suitable weather resistant material, appropriately sealed to protect the internal hardware. The system 100 may include a display 106A, such as a touchscreen display, upon which information may be displayed and entered. The display 106A may include an integrated camera that may be used to capture images and that may be used in performing facial recognition of individuals. The display may also include or operatively associate with one or more integrated speakers for providing audio output, a microphone for receiving audio information to facilitate two-way communications to a remote location. The system 100 may include a scanner 110A for scanning items, such as deliveries, as will be explained in more detail below. The scanner 110a may be, for example, a QR scanner, an Optical Character Recognition (OCR) or a bar code scanner 110A in some instances. The side of the system 100 shown in FIG. 1A can be used for deliveries and inspections. A delivery person may scan delivered materials, equipment or other items via the scanner 110A and may interface with the system using the touch screen display 106A. An inspector may scan or take images of inspection documents via the scanner 110A or camera and may interface with the system using the touch screen display 106A. In some embodiments, there may be fewer sides in which to interact with the system for all authorized personnel. An overhang 112 may be provided to assist in decreasing glare and protecting some of the items on the housing from the weather.

FIG. 1B depicts a side of the system 100. This side can include a touch screen display 106B as well as a scanner 110B. Display 106B may include or be operatively associated with an integrated camera for capturing images, speakers for providing audio output and a microphone to facilitate two-way communications with a remote location. Still further, this side of the system 100 may include data ports 108B. The system 100 may be accessed to gain access to equipment, tools and to sign in or sign out when leaving or entering the project location, as will be described below.

Figure 1C:
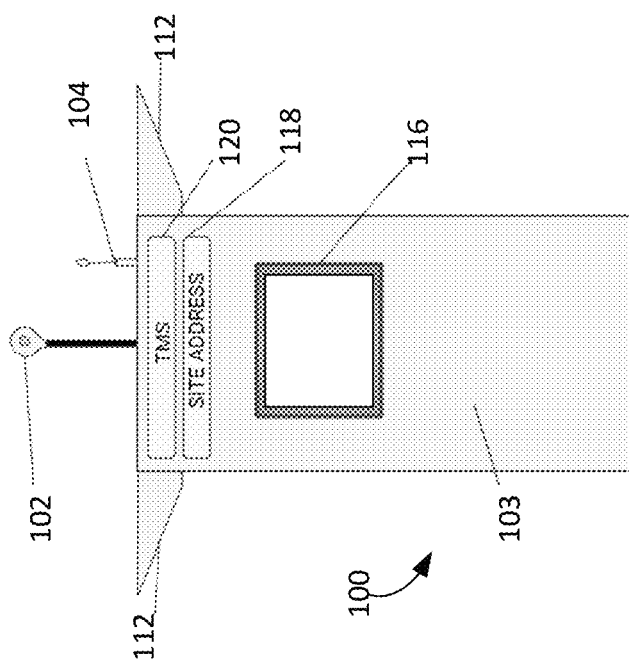

FIG. 1C shows a third side of the system 100. This side has a location 116 in which information such as permits, specifications, instructions, tax information, plans, and the like and may be displayed. In some embodiments, the information displayed may assume electronic form so that a video display is provided in the area 116 of the housing 103. A tax map submap (TMS) number 120 for the project location may be displayed on the housing 103. Other location identifying information can be displayed such as location number, store number, assembly number, area within the project location and the like. In addition, the site address 118 may be displayed on the system 100. The site address may refer to both the mailing address for the project location and/or other physically identifying information associated with the location.

FIG. 1D shows a side of the system 100. An access panel 122 may be provided to access a breaker box for the system 100. An additional access panel 124 may also be provided to access internal components of the system 100. Still further, access panel 126 may be provided to gain access to power source for providing power at the project location. The access panel 126 may be under programmatic control in some instances to regulate access to the power source. If access is granted, the panel is unlocked, whereas if access is denied, the access panel 126 is locked. In some embodiments, access to the power supply may be controlled by controlling the flow of power to the power source under programmatic control from the controller. These control mechanisms may be used separately or in conjunction.

Figure 1F:
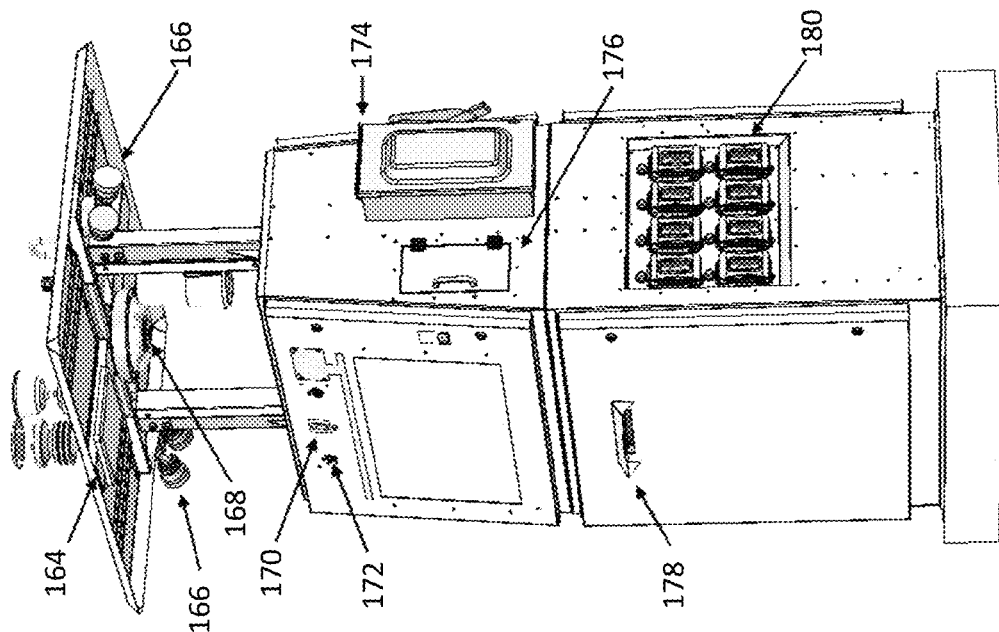
Figure 1E:
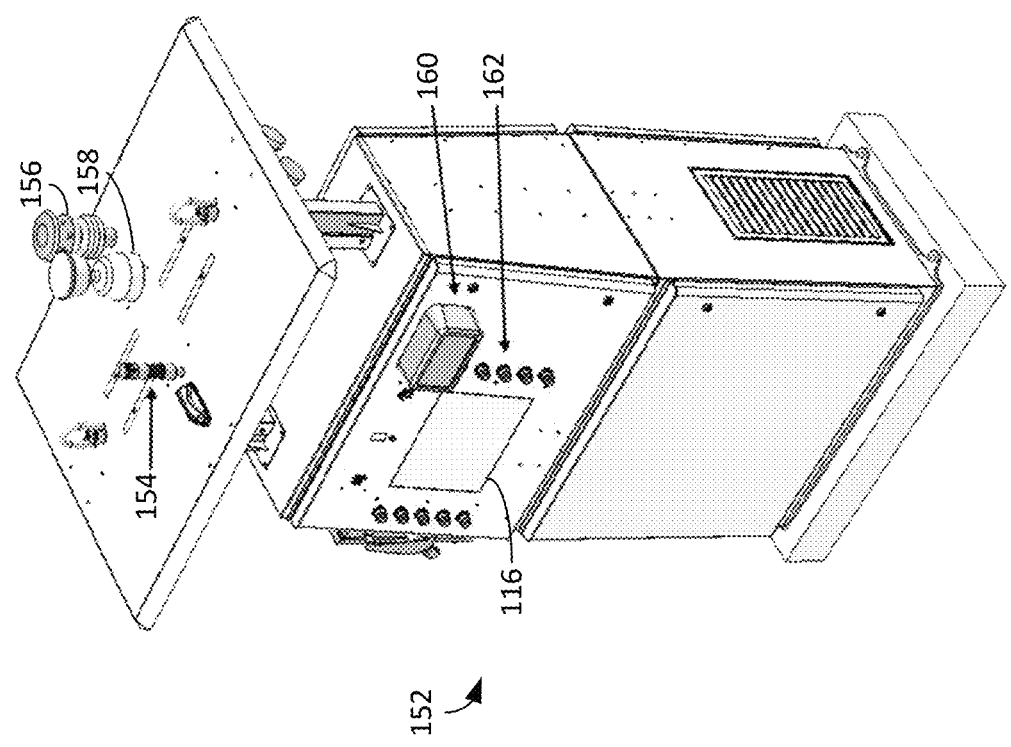

Referring to FIGS. 1E and 1F, the housing 152 can include a worker side that is configured to be used by a worker at the project location. The housing can include an alarm indicator 154 that can be actuated as described herein. The housing can include a weather station 156 that can include an integrated or separate fluid (e.g., rain) collector 158. Biometric reader 160 can include an iris scanner, fingerprint scanner, palm print scanner, facial scanner or some combination. Display 116 can be proximity to input assemblies such as buttons 162. The housing can include a field receiver 164, lights 166 and camera 168. One or more cameras can provide a 360° field of view and include a wireless connection for transmitting images to a remote computer device. The images can also be used for input to the system including input allowing the system to identify delivered materials. The system can include one or more second cameras 170 such as webcams disposed at various locations around the system for capturing images. The lights can include motion activation and photoelectric activation. Speakers 172 can be included to provide audio information to a user, worker, inspector, or other party using or near the system. The audio information can include instructions, alarms, and the like. Power junction 174 can include a shut off switch that can be used in emergency and non-emergency situations. The system can include a secondary power source, such as a battery, so that when the main power is shut off, an alarm can sound, notification send to a remote computer device of other indication that the system or power source has been powered down. The system can include a hand scanner (not shown) that can be protected by a hand scanner access door 176. A document scanner 178 can be included in the system for receiving physical documents, converting the physical document into a digital representation, and storing the digital representation on the computer readable medium or the persistent storage. The system or housing can include electrical outlets 180 for providing power to various tools and equipment at the project location including recharging batteries. The system can include a wired connection to remote computer devices of a transceiver to provide a wireless connection to remote computer devices.

Figure 1G:
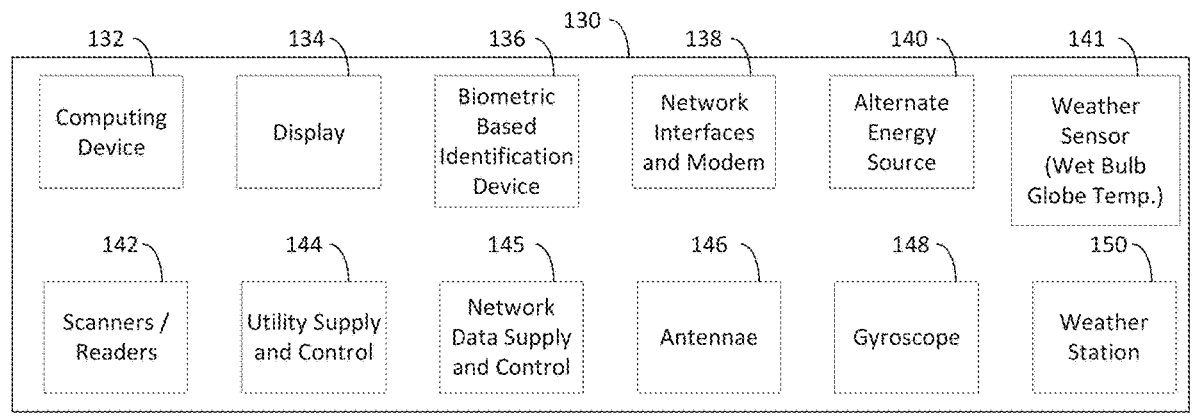
FIG. 1G is a block diagram of components of aspects of the system.

FIG. 1G depicts components that may be included in the system of exemplary embodiments even when not included in a housing. The system may include a computing device 132. The computing device 132 may take many different forms indicating a desktop computing device, a laptop computing device, a mobile computing device, an embedded system, a smartphone, special computer device, custom computer device, or the like. A display 134 may be integrated with the computing device 132 or as a separate device, such as a liquid crystal display (LCD) device, a light emitting diode (LED) display device or other types of display devices on which computer information may be displayed. One or more biometric-based identification devices 136 may be provided. As will be explained in more detail below, multiple biometric-based identification devices may be used. Network interfaces and a modem 138 may be provided. The network interfaces may interface the computing device 132 with a local area network or a wide area network wherein the networks may be wired or wireless. A modem may be provided to communicate telephonically or over cable lines with remote computing devices.

The system 130 may be implemented in a distributed fashion and may include an alternative energy source 140. For example, solar panels, wind turbine(s), a battery or the like may be used. In one embodiment, the alternative energy source may be physically affixed to the housing or in communications with the system or controller. For example, solar panels or a cable to a wind power source could be configured to provide power to the system and/or can be affixed to the system or housing. Alternatively, a power line leading to the alternative energy source may be connected to the housing and system to provide power to the system, housing and associated components such as external power supplies.

The system 130 may include various scanners and readers 142, such as those described above relative to housing. The system 130 may include a utility supply and control 144 and a mechanism for turning the utilities, such as power, gas and/or water, on and off under a programmatic control. The system 130 may include an internet data supply control 145 and a mechanism for turning the access to this service on and off under a programmatic control. Programmatic control may be provided to grant or deny access to such resources. The system 130 may include an antenna 146 for wireless communications signals to receive and transmit. The system 130 may include a gyroscope 148 to monitor any moving of the system. The gyroscope 148 may indicate motion indicative of whether someone is trying to move or tilt the housing or other component of the system. Logic may be provided to send a notification in such an event where the gyroscope indicates substantial enough movement. The system 130 may include a weather station 150 to measure current weather conditions, such as temperature, air movement, humidity, precipitation, barometric pressure, direct sunlight, and the like. Input from the weather station 150 may be used to inform decision making by the system in some instances. Alternatively, the weather may be collected via software, such as from a weather service or other weather source. Similarly, the system 130 may include a weather sensor 141. The sensor can be a wet bulb globe temperature adapted to measure, among other things, heat stress in direct sunlight, which accounts for temperature, humidity, air movement (direction and speed), sun angle and cloud cover (solar radiation).

Figure 2A:
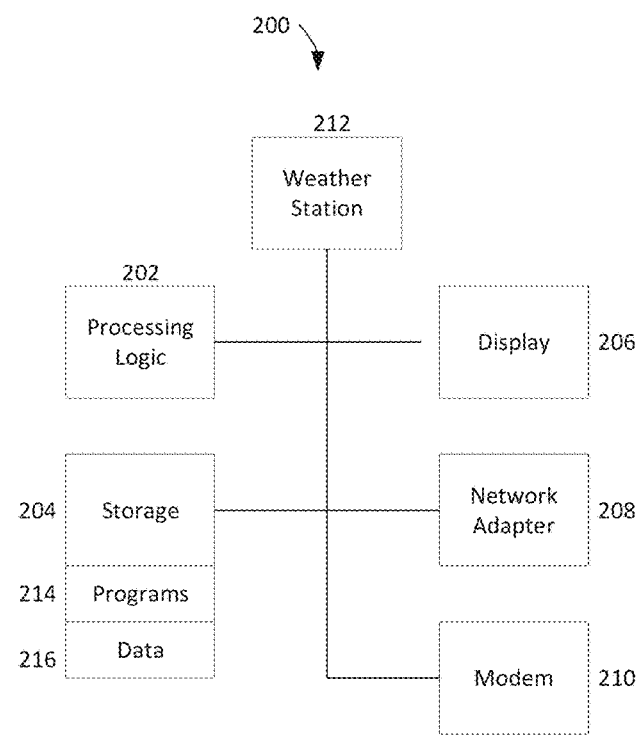
FIG. 2A is a block diagram of aspects of the system.

FIG. 2A shows an example of a computing device 200 for the system. The computing system may include processing logic 202, such as microprocessors, controllers, field programmable gate arrays (FPGA), application specific integrated circuits (ASICs) electronic circuitry, and other types of logic. The processing logic 202 performs the operations of the computing device 132. A storage device 204 may also be provided. The computer readable medium and/or data storage device 204 may take various forms, including magnetic storage, optical storage, etc. Storage capability 204 may include computer-readable media, including removable computer readable media, such as disks, thumb drives and the like, or disk drives, solid state memory, random access memory (RAM), read only memory (ROM) and other types of storage. The computing device may include a display 206, such as an LCD display, an LED display, or other types of display devices on which video information may be displayed. The computing device 200 may include a network adapter 208 for interfacing with networks and a modem 210 for communicating wirelessly, over telephone lines or cable lines with remote devices. The processing logic 202 may use information stored in the storage device 204. In particular, the processing logic 202 may execute programs 214 stored in the storage and may access and store data 216 relative to the storage device 204. The computational functionality of the system described herein may be realized by the processing logic 202 executing the programs 214.

Figure 2B:
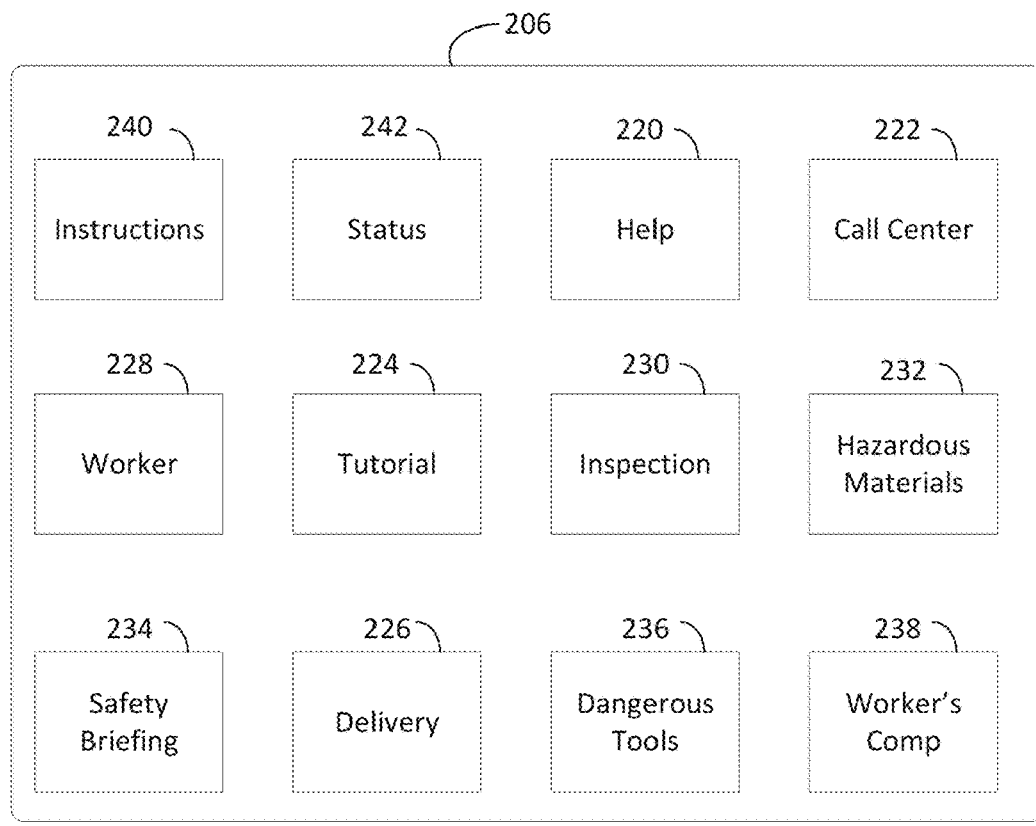
FIG. 2B shows aspects of a user interface.

FIG. 2B shows an example of a user interface on display 206, such as found in the housing 100. The user interface may include activatable elements. A user may depress these activatable elements or select these activatable elements using an input device, such as a mouse, keyboard, touchscreen, or the like, to activate the components. The display 206 may include a help element 220 that may be activated to obtain help information regarding use of the housing. It may also contain real time project or process plans. It may also include "how to" assistance including videos related to the various projects, stages, processes, and tasks performed at the project location. The user interface on the display 206 may also include a call center activatable element 222. Selection of the call center activatable element 222 may cause a call to be initiated with a call center so that the individual using the system 100 may have a telephone and or video conference with personnel at the call center. The user interface on display 206 may also include a tutorial activatable element 224. Selection of the tutorial activatable element 224 causes a tutorial to be displayed to teach the individual about operation of the housing.

A list of hazardous materials at the project location may be activated by activating element 232. This list is updated as hazardous materials are delivered, removed, or consumed. Access to hazardous materials may also be controlled via the system 130. The display may show instructions 240 for completing certain tasks or other information. A status of tasks and materials can be displayed at 242. For example, a worker can view the display and receive status information about materials such as anticipated delivery, route information, or tasks as well as the status of tasks including performance steps, start times, competition times and the like. A hazardous material record can be created and recorded on the persistent storage that includes a verifiable pairing to the hazardous material.

Figure 2C:
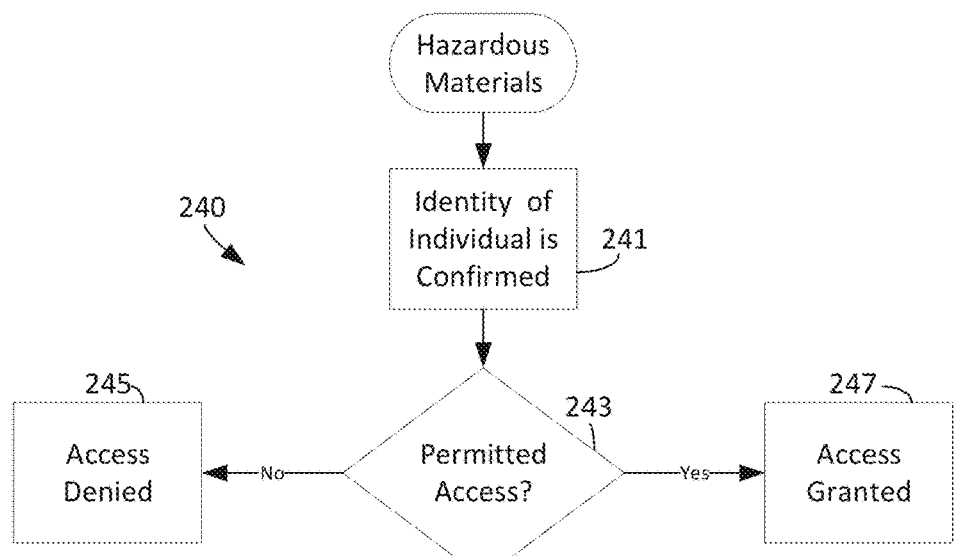
FIG. 2C shows a flowchart of aspects of the system.

FIG. 2C shows a flowchart 240 of steps that may be taken to control access to hazardous materials at the project location. First, the identity of the worker is confirmed 241, such as described above using biometric identity verification. The worker's information is accessed to determine if the individual is to be granted access to the hazardous materials 243. If the permissions indicate that access is to be granted, access is granted 247. In contrast if the permissions indicate that access is not to be granted, then access is denied 245. Permission information can be included in the worker information record. Permission information can be retrieved from the persistent storage or the system.

The user interface on display 206 (FIG. 2B) may also include a safety briefing activatable element 234. Activation of this element 234 results in a safety briefing being displayed on the display 206. The user interface on display 206 may include a dangerous tool activatable element 236. Activation of this element 236 causes the display of a list of dangerous tools on the project location. An individual must have the proper authorization or certification to use such dangerous tools. The authorization or certification may be stored with the permissions.

The system 130 may include software which allows each tool to be coded or assigned to authorized personnel. Each tool can have a verifiably paired virtual representation associating the specific tool with the virtual representation. This can be verified by the system through recognition of the tool from a reader or sensor. The tool supplier record can be created by the tool supplier and include a virtual representation associated with the tool and store the virtual representation paired with the tool on the persistent storage. When the tool arrives at the project locations, the system can retrieve the tool supplier record and determine of the tool requested if the actual tool that arrived. A tool verification record can be created and stored on the persistent storage representing that the tool delivered and received matches the tool supplier record.

Figure 2D:
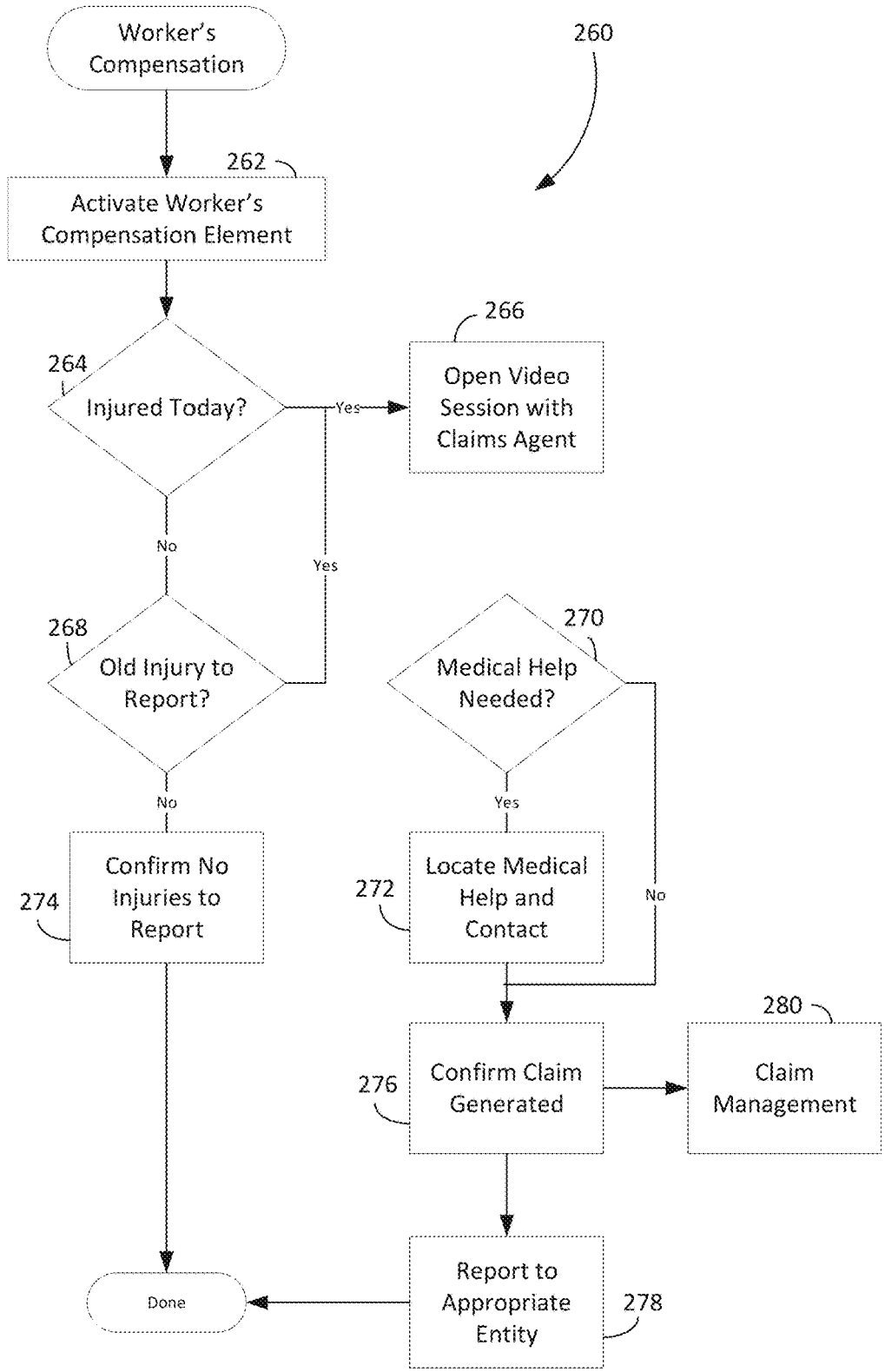
FIG. 2D shows a flowchart of aspects of the system.

The system 130 can also allow or prevent access to the project location. When a worker arrives at the project locations, the selection of the worker's compensation activation element 238 may be required at the beginning and end of each workday or when an injury occurs to track the worker. FIG. 2D provides a flowchart 260 of steps taken when the element 238 (FIG. 2B) is activated at 262. All workers may be required to enter this information each day. If the worker indicates that the worker has been injured 264, a video session with a claim agent can be initiated at 266. The claim agent may gather information to initiate any claim processing. The claim agent may determine if medical assistance is warranted 270. If medical help is warranted, the location of appropriate medical help can be identified based on a location of the project location (e.g. based on proximity and type of injury) and contact is made with the medical assistance (e.g., calling of an ambulance, hospital or urgent care facility) 272. The facilities may be chosen to be "in network" for the worker's compensation carrier. A confirmation of the claims may be generated 276 and sent to claims management 280. In addition, a report may be sent to the appropriate entity or authority at 278. The steps 266, 270 and 272 may also be performed in the instance in which the individual has an older injury to report 268. Where there is no injury to the individual, the lack of injury is reported 274.

Shipping or delivery company personnel may activate the delivery activatable element 226 (FIG. 2B). This causes the delivery functionality to be displayed where delivery notes may be added and where information may be gathered from the delivery person regarding a particular delivery.

A worker activatable element 228 may be selected by workers. Selection of this activatable element 228 causes the activation of the worker functionality whereby the worker may sign in, request tools, equipment, power or materials, leave notes or the like.

An inspector activatable element 230, may be activated to cause the inspector functionality to be activated. The inspector functionality may enable an inspector to add inspection notes, provide electronic inspection certificates and the like. The system can provide reports that can be automatically generated from the existing data described herein as well as notes manually added during the construction process. The reports can be generated at predetermined times such as daily or upon completion of specific tasks.

Figure 3A:
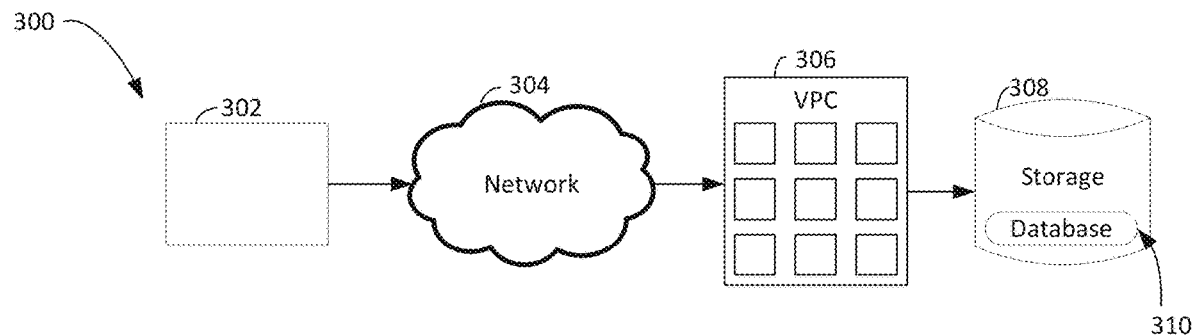
FIG. 3A shows an example of a communications environment.

As shown in FIG. 3A, the exemplary embodiments may be implemented in a decentralized computing environment 300, that may include distributed systems and cloud computing. FIG. 3A shows one or more systems 302 that may be in communication with a remote cluster 306 via a network 304. The cluster 306 may store information received from the system 302 and provide added computational functionality. The network may be a wired network or a wireless network or a combination thereof. The network 304 may be a secure internet connection extending between the system 302 and the cluster 306, such as a virtual private cloud (VPC). The server may be a computing device and can be in communications with the site computer device. The cluster 306 may include access to storage 308. The storage 308 may include a database 310 in which information regarding a project location is stored in a consistent manner.

Figure 3B:
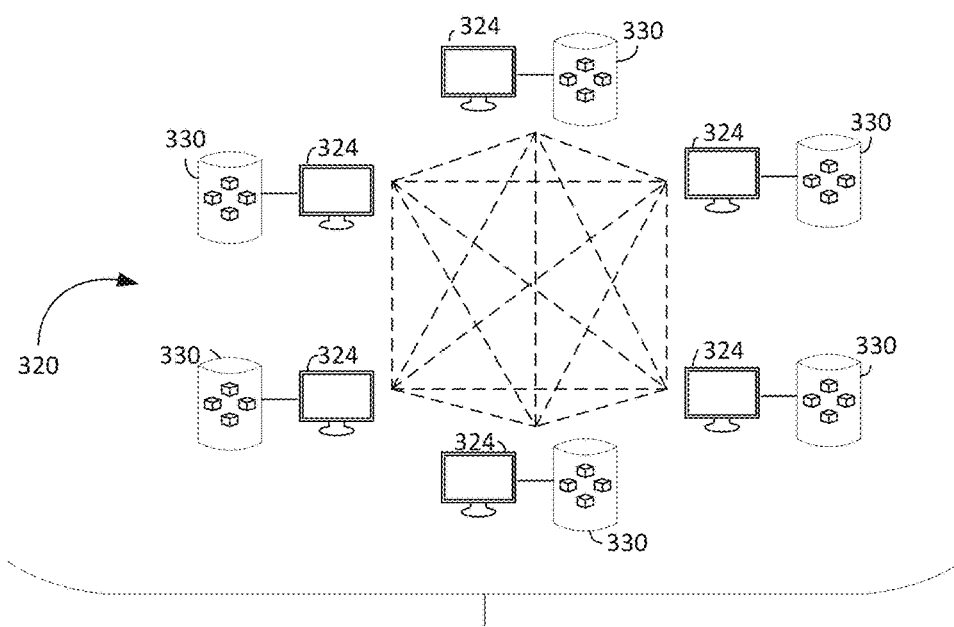
FIG. 3B shows an example of a persistent storage.

FIG. 3B shows diagram 320 of an example of a peer-based network where a persistent storage 330 is broadcast and shared among the nodes 324. This network may be resident in the VPC cluster 306 (FIG. 3A) or in the network 304 for example. The nodes 334 may represent computing resources, such as server computer systems or other computing systems, residents at the parties identified in FIG. 27, for example. Each node that has access to a copy of the persistent storage 330.

Figure 3C:
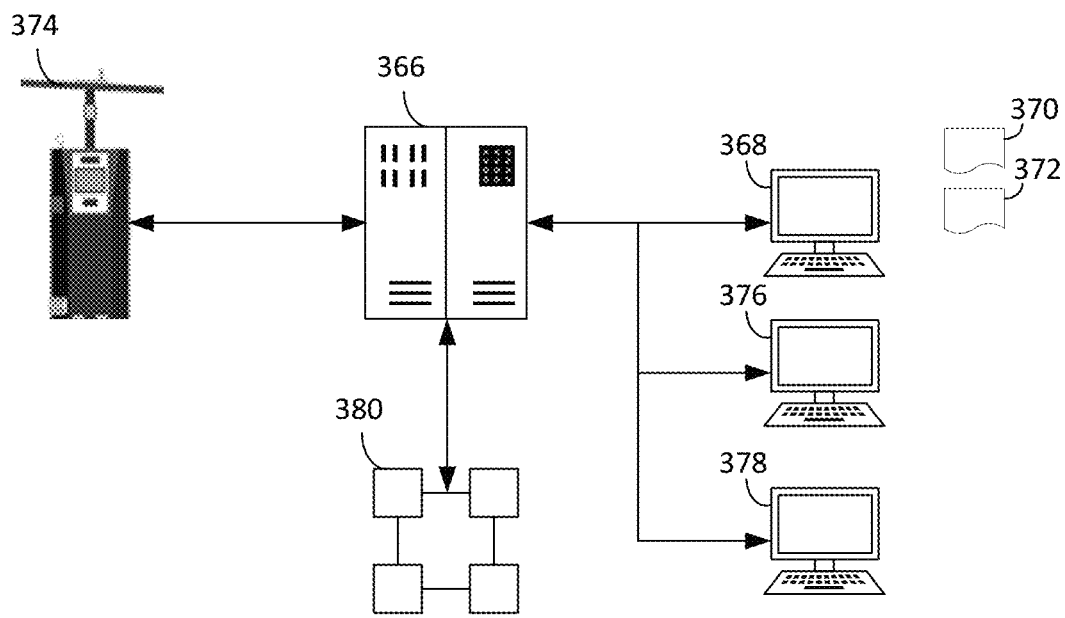
FIG. 3C shows a schematic of the aspects of the system.
Figure 3D:
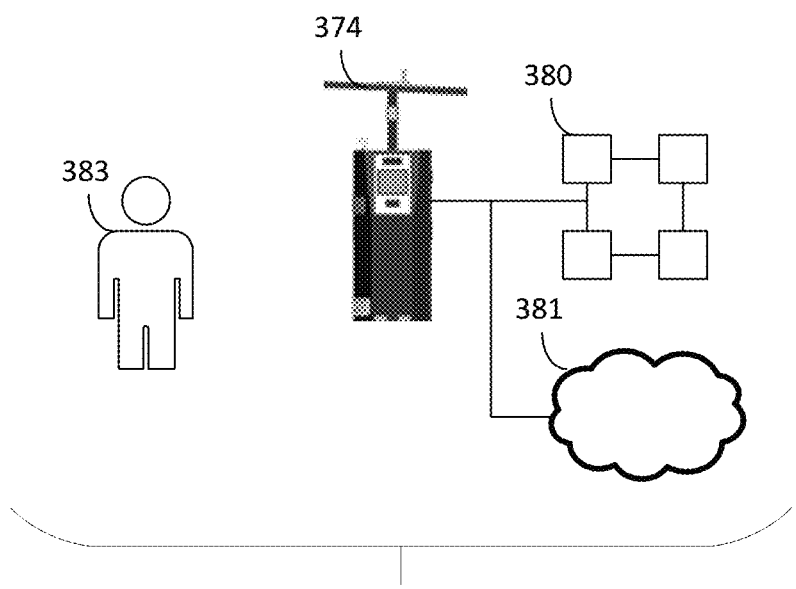
FIG. 3D shows a schematic of the aspects of the system.

Referring to FIG. 3C the server 366 can be in communications with design computing device 368 that can be used to transmit design information 370 and material requirement record 372 to the server and housing or project location computer device 374. The information from a designer, supply company or other third party can also be stored on the persistent storage and retrieved by the system. The housing can be configured for receiving a material requirement record from the designer representing physical materials needed for the project or process, creating an actual material requirement record for the project or process representing the actual materials delivered to the project location by a supply company, creating a final material record according to a difference between the material requirement record and the actual material record, receiving material installation information from the supply company representing the installation criteria for the actual materials delivered to the project location, receiving installation verification information representing the actual material was installed by an authorized installer 383 (FIG. 3D) and under a set of compliant environmental conditions, including weather conditions, receiving warranty criteria from the supply company representing the warranty requirements associated with the actual materials installed, determining if the warrant criteria are met, creating a certificate of warranty according to the final material requirement record and installation verification information, and storing the certificate of warranty on the persistent storage.

Conditions associated with a project, project location, location marker, delivery, pick-up, worker, process, or task can include physical location (e.g., GPS coordinates), weather conditions, impacted workers, impacted materials, impacted equipment, date and time, duration, pre- and post-events (e.g., chronologically relevant action(s)), managers and supervisors on site and/or responsible. An insurance event can be an event, act or omission that affects the risk associated with insurance coverage. An insurance event can include an injury, loss, potential for an injury or loss, failure to supervise, misreporting of materials, workers, and the like that could cause an insurer to pay a claim or create the potential for an insurer to pay a claim.

Processes, projects, and task specifications, which may be needed for compliance with warranty, insurance, design, specifications, inspection, and other requirements, can be received at 376 and regulatory code can be received from a regulatory computer device 378 either directly or from the persistent storage. The regulatory requirements can include approved materials that are approved by regulatory entities, such as governments, or designers, such as architects. Regulatory requirements can include product safety codes, building codes, fire codes, labor standards, building permit requirements, building and labor licenses, and the like. The regulatory requirements can include processes and procedures for handling, use, installation and assembly. For example, during building construction, opening for windows and doors on second floors or higher should have safety railing installed.

The various computer devices, including the server and site computer device (e.g. system, controller, and any combination), can be in communications with persistent storage 380. The persistent storage can include a distributed ledger, immutable database, block-chain structure, and the like. The communications between the various computer device, including the server and the site computer device and persistent storage can be a global communications network, wide area network, or local area network, delivered to a computer readable medium from one device to another (e.g., USB drive, CD, DVD) and can be wired or wireless.

Figure 4:
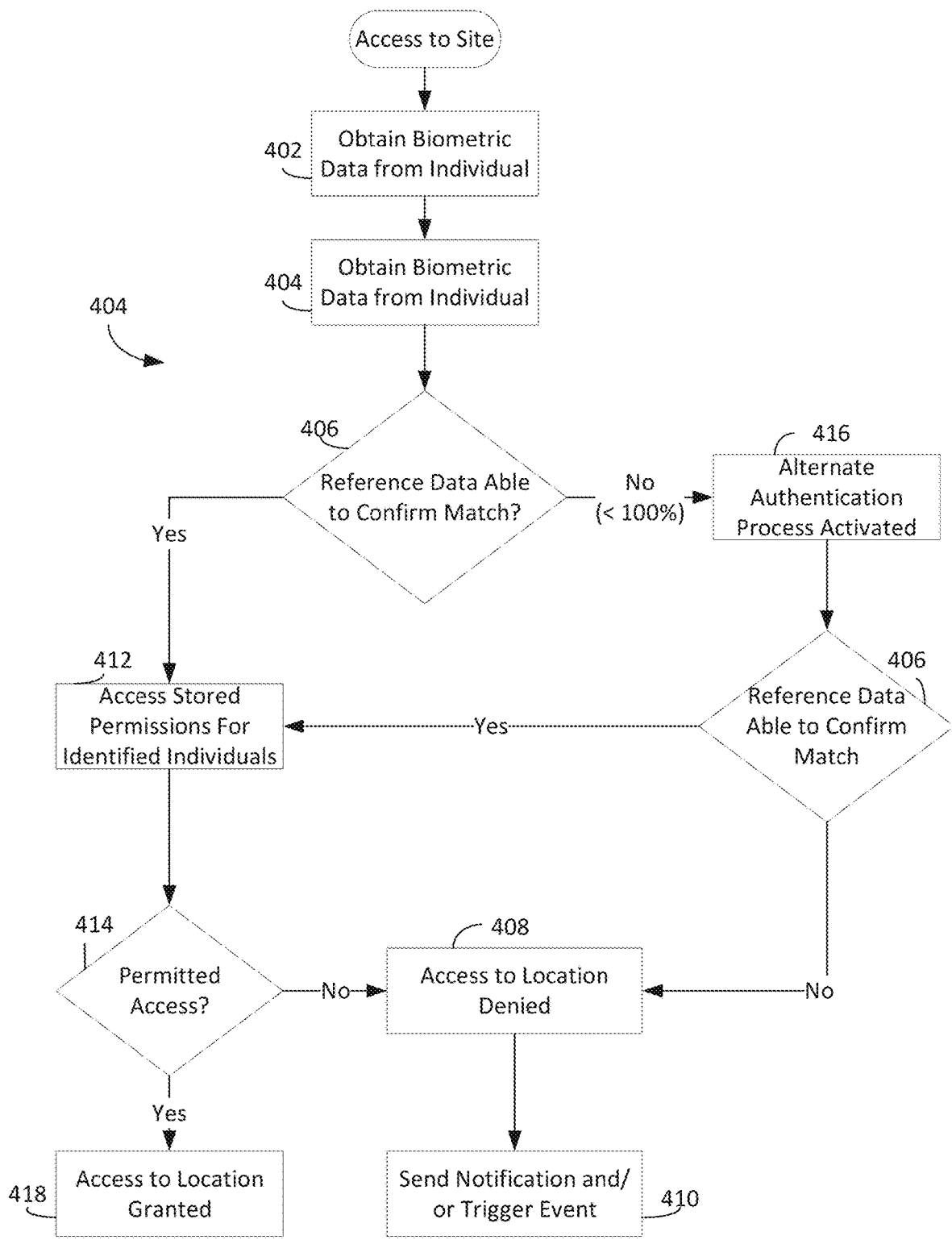
FIG. 4 shows a flowchart illustrating aspects of the system.

FIG. 4 shows a flowchart 400 identifying steps that may be performed in exemplary embodiments regarding this functionality of the system. Initially, biometric data is obtained from a worker or other individual that is seeking access to the project location 402. In some exemplary embodiments, a camera 102 may capture an image of an individual and facial recognition may be performed. The biometric data in this case is the facial image of the individual. In other exemplary embodiments, the biometric data may be, for example, fingerprint data, hand scan data, voice print data, retinal scan data or the like, gathered by appropriate biometric-based identification devices. The obtained biometric data is stored, and then previously stored data is accessed from storage to compare biometric data for known individuals and to attempt to identify the individual 404. A comparison may be made between the gathered biometric data and the known biometric data to determine if there is sufficient closeness for there to be a match. Information regarding the identity of the individuals for which the biometric data is stored is also stored in the storage device. A determination is then made whether there is a match or not 406.

If there is not a match 406, a manual process may be executed, or an alternative authentication process may be deployed 416. If this alternative authentication fails to produce a match 406, access to the project location may be denied 408. In addition, a notification may be sent to a responsible party and/or an event may be triggered, such as contacting security or law enforcement officials 410. If the alternative authentication process produces a match, the process proceeds to 412.

The system may store permissions for each individual accessing the project location. These permissions may identify the dates and times where the individual is given access to the project location. In addition, the permissions may specify what tools, equipment, or materials the individual can access. The permissions may specify whether the individual can use a power supply and may specify what portions of the project location the individual is permitted to access. These permissions may be accessed to determine the permissions for the identified individual 412. If the permissions indicate that access is permitted 414, the individual may be granted access to the project location 418.

Figure 5:
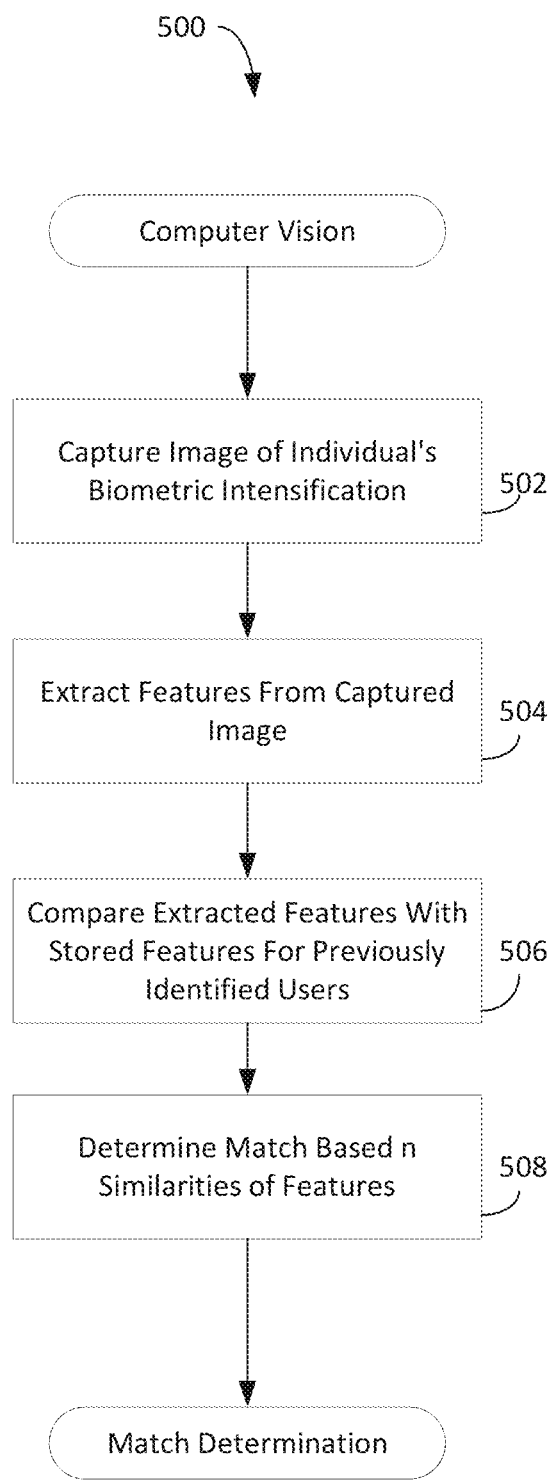
FIG. 5 shows a flowchart illustrating aspects of the system.

FIG. 5 shows steps that are performed in a case of computer vision for 402, 404 and 406 of FIG. 4. The flowchart 500 begins with 502 in which an image of an individual is captured for biometric recognition. This may be captured by a number of different types of image capture devices, including an intermittent video camera, still camera, iris scanner, facial scanner, fingerprint scanner, or other type of capture device. In the case where an image of the face of an individual is captured, identifying features may be extracted from the captured image 504. In other words, unique facial features that help to identify an individual are extracted from the image. The image may be filtered and/or normalized. The features are then compared with the stored features for identified individuals 506, determination is made whether there is enough similarity for there to be a match.

FIG. 6 shows a diagram 600 that illustrates various types of biometric data 602 that may be obtained by biometric-based identification devices at the project location to attempt to identify individuals. Biometric data may include facial recognition 603, an iris/retinal scan 604, a fingerprint scan 608, a hand scan 608, a voice print 610 or heart rate signature 614. It should be noted that other types 612 of biometric data may also be used in exemplary embodiments to help identify individuals uniquely. Also, an individual may be required to provide multiple types of biometric data in some instances.

When individuals attempt to access the project location and are not granted access, certain events may be triggered (see 410 in FIG. 4). FIG. 7 shows a diagram 700 that provides an example of different types of triggered events 702. One type of triggered event is an alarm 704. This alarm may include visual alerts, audio alerts and any combination thereof. The alarm may be a silent alarm to individuals. Another event that may be triggered is to send notifications to a supervisor for the project location 706. The supervisor may, for example, receive an email, a text, a phone call or another notification that someone is trying to access the site that is not permitted. A triggered event 702 may also include the contacting of law enforcement or a member of a security service indicating that an unauthorized party has tried to access the project location. Lastly, a triggered event 702 may include prompting the individual to produce proper identifying information to an official at the site or to a scanning device at the housing 100.

Figures 8, 9:
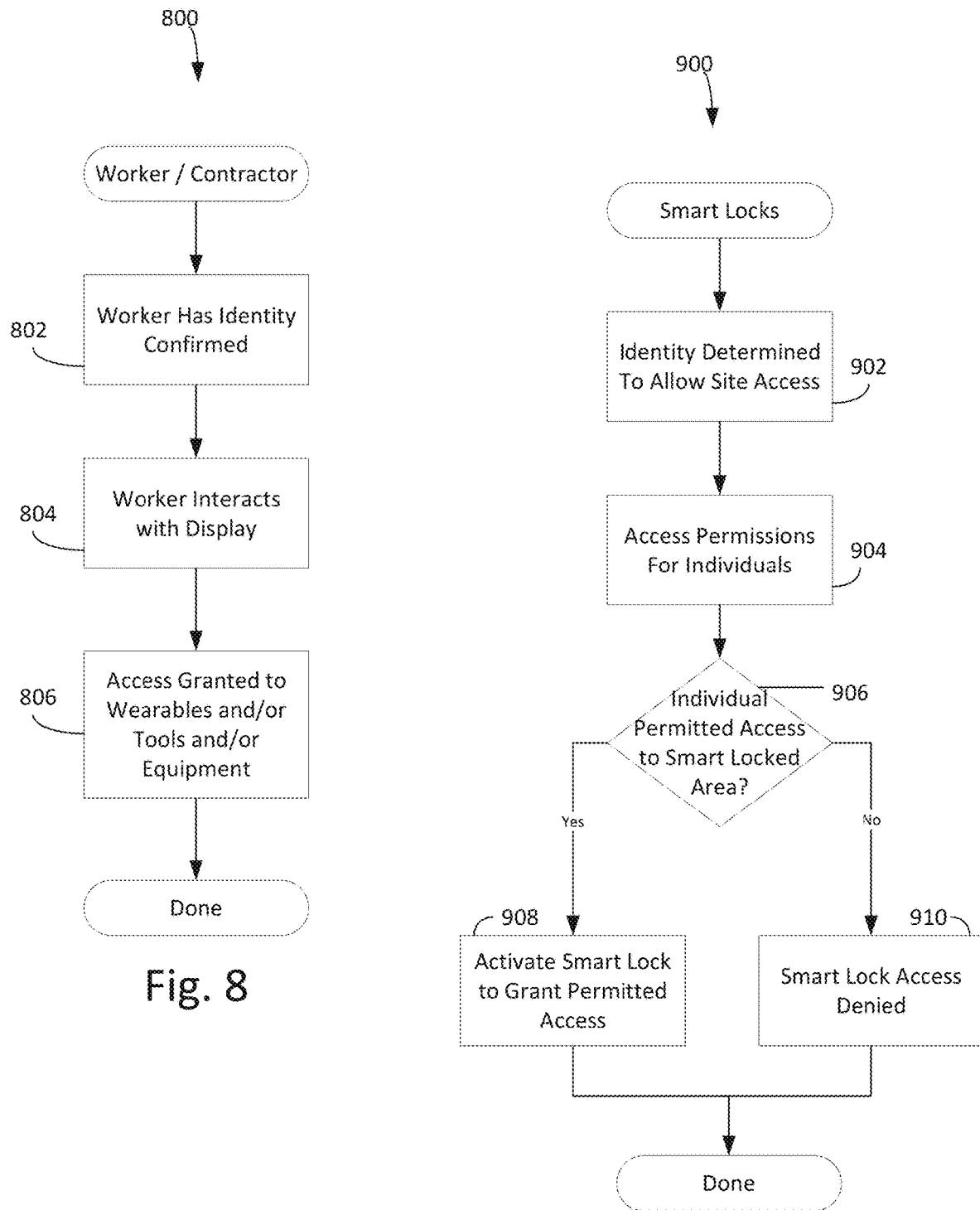
FIG. 8 shows a flowchart illustrating aspects of the system.
FIG. 9 shows a flowchart illustrating aspects of the system.

FIG. 8 shows a flowchart of the steps that may be performed to ensure that a worker gains access to the appropriate items once they have been granted access to the project location. As shown in the flowchart 800 of FIG. 8, initially the worker has their identity confirmed, as has been discussed above 802. The system may offer an alternative touchscreen option to place a call to the appropriate party should the software fail to verify and otherwise authorized the worker. The worker may be prompted to interact with the display, such as the touchscreen 106B (FIG. 1) to register and to indicate whether they seek certain items. For example, with the user interface of FIG. 2B, the worker may activate the worker activatable element 228. Access is then granted to wearables and/or tools and/or equipment 806. The wearables, the tools and/or equipment may be stored in sheds or in other secured locations under the control of smart locks that may be controlled by the computing system of the system.

FIG. 9 provides a flowchart 900 of the steps that may be performed relative to smart locks at the project location. The individual, such as a worker, has his/her identity determined and has access to the project location 902. The system may offer an alternative touchscreen option to place a call to the appropriate party should the software fail to verify an otherwise authorized individual. The permissions stored for the individual are accessed 904. A determination is made whether the individual is granted access to a smart locked area 906. If the individual has permission to access the area 908, the smart locks may be de-activated to unlock the area, such as where wearables, tools or equipment are located. Before the individual can use the tools/equipment, the individual may first be required to wear some of the wearables and to scan the tools or equipment to indicate that they will be using the tools or equipment. If the individual lacks the proper permissions to access the area, then access to the area is denied 910, such as by keeping the smart locks locked. In one embodiment, the tools and equipment used can be determined so that the proper tools are used for installation of materials if required for warranty requirement compliance.

Figures 10, 11:
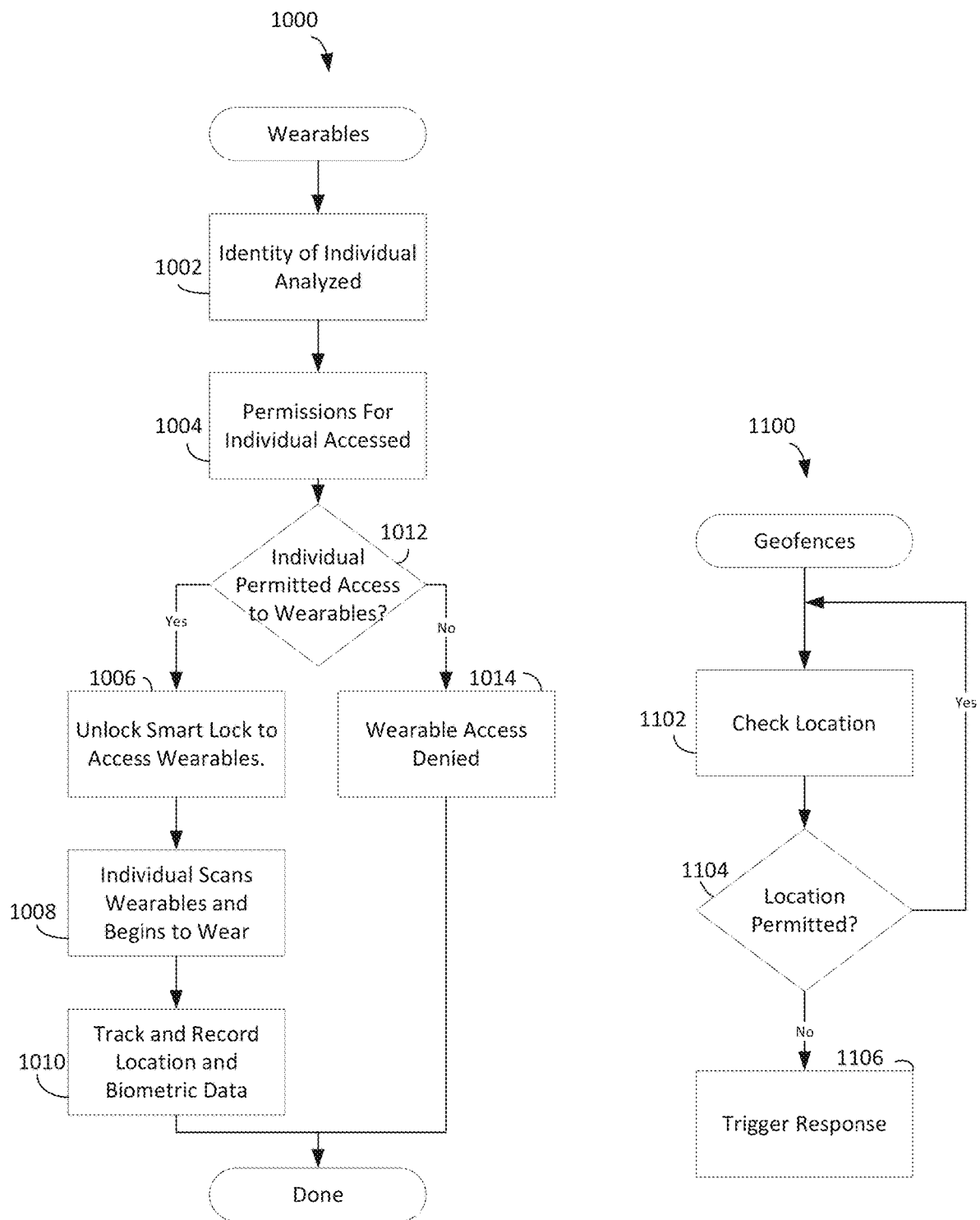
FIG. 10 shows a flowchart illustrating aspects of the system.
FIG. 11 shows a flowchart illustrating aspects of the system.

FIG. 10 contains a flowchart 1000 illustrating the steps that may be performed to obtain the wearables. For some individuals, a wearable can be provided to the individual prior to interaction with the system and used to register with the system. This individual can receive the wearable and upon approaching a housing, be registered with the system when the individual reaches a certain proximity to the system.

The wearables may include safety gear, such as hard hats, gloves, goggles, vests, and the like, as well as wearables for tracking and obtaining biometric data. The identity of the individual is confirmed 1002, and the permissions for the individual are accessed 1004 and a determination is made based on the permissions if the individual should be granted access to the wearables 1012. The system may offer an alternative touchscreen option to place a call to the appropriate party should the software fail to verify an otherwise authorized individual. If it is determined that the individual should be granted access, the smart lock for the storage location of the wearables is unlocked 1006. The individual may then be prompted to scan information regarding the wearables so as to register the wearables and associate the wearables with the individual 1008. In one embodiment, the system may use one or more images of an individual to determine if the individual has the necessary safety equipment. For example, an image of the individual taken by the housing can be used to determine if the individual is wearing a hardhat and generate a warning if no hardhat is present can be generated and transmitted appropriately.

The system may require that an individual wear certain safety equipment in the form of wearables. The system may record what wearable the individual scans. The system tracks and records the location and biometric data gathered by the wearables 1010. The wearables may include smart vests, bracelets, badges, sensors, and the like that provide location information and biometric data, such as heart rate, body temperature, blood pressure, breathing rate, gyroscopic informatic and/or other information. These wearables assist the system in tracking the location of individuals of the project location. These wearables also help to track the biometric data of individuals. The biometric data may be helpful in identifying that an individual is experiencing an accident, a health event or is idle. The biometric data is stored so that a record of the biometric data can be kept. If in 1005, it is determined based on the permissions that the individual should not be granted access, then access to the wearables is denied 1014.

The use of the wearable to track location helps to facilitate use and installation of material to determine warranty requirement compliance. The wearable information can be combined with geofencing in an exemplary embodiment. The geofencing enables the system to track and limit access to locations of individuals at the project location. The project location may be partitioned into areas where different permission rights are given for the various areas. For example, a mechanic can be given access to the repair section of a project location and denied access to the paint area. A worker can be given access to the point-of-sale portion of a project location and denied access to the loading docks.

As shown in FIG. 11, a flowchart 1100 shows some of the steps performed automatically and can be performed without notification to an individual. The process begins with the checking of the location 1102 of an individual. A determination is made in 1104 whether the individual is permitted to be at that location. If the individual is not permitted to be at that location, a response is triggered 1106.

Figure 12A:
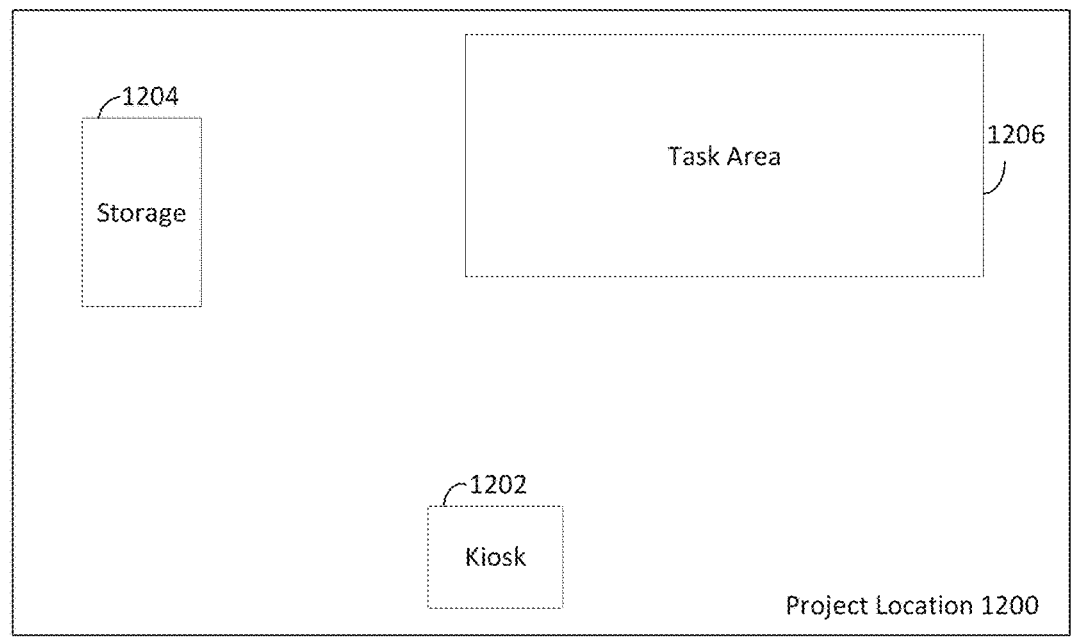
FIG. 12A shows a plan view of a project location.

To help illustrate an example of geofencing, FIG. 12A shows an illustrative project location 1200. The project location 1200 may include a housing 1202 for the system as well as storage location 1204 that can be a building, trailer, shed or the like. The storage location 1204 may hold tools, equipment, wearables and/or materials. The project location 1200 may also include a task location 1206. The task location may be where tasks are performed using materials to produce a good or offer a service.

Figure 12B:
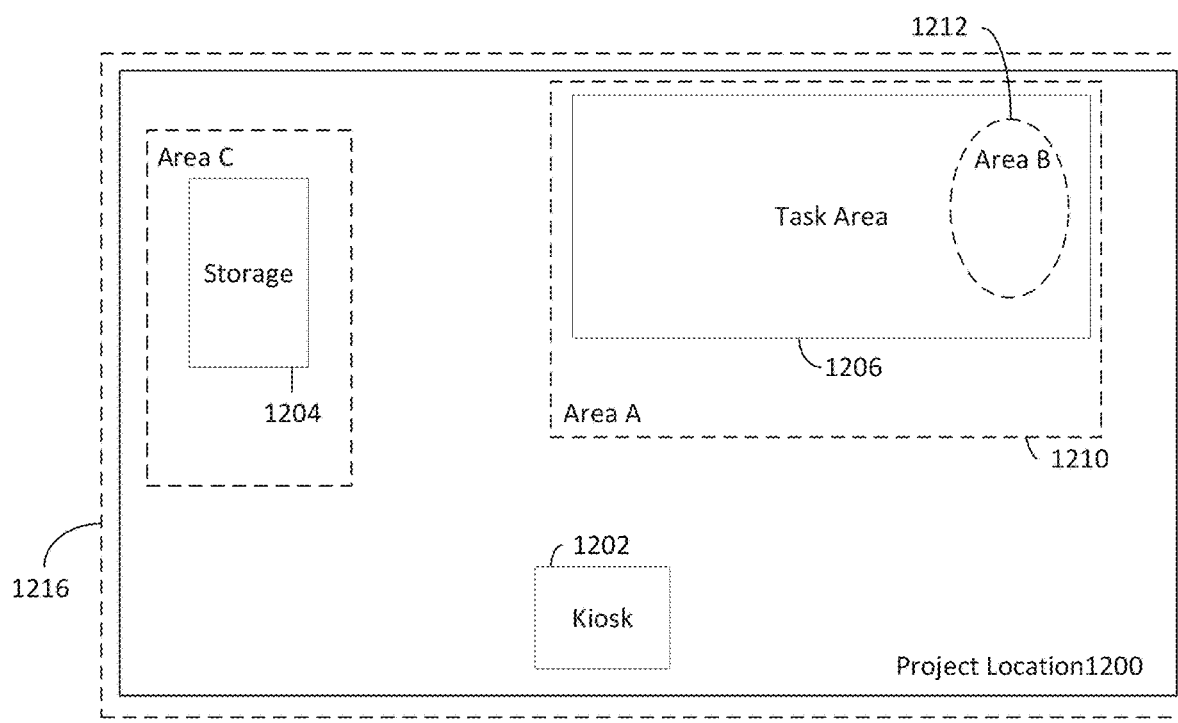
FIG. 12B shows geofencing areas at a project location.
Figure 13:
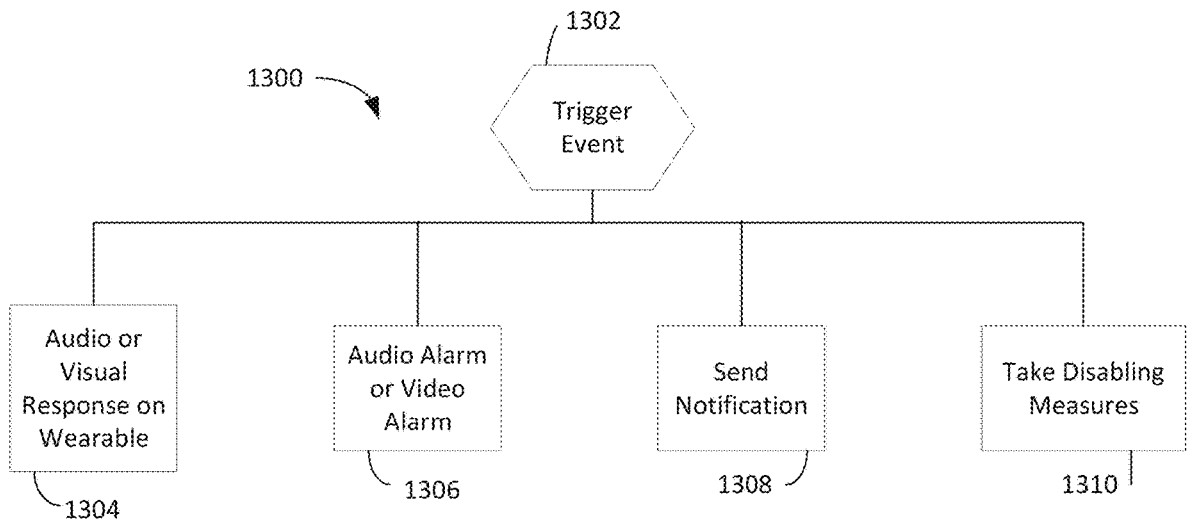
Figure 14:
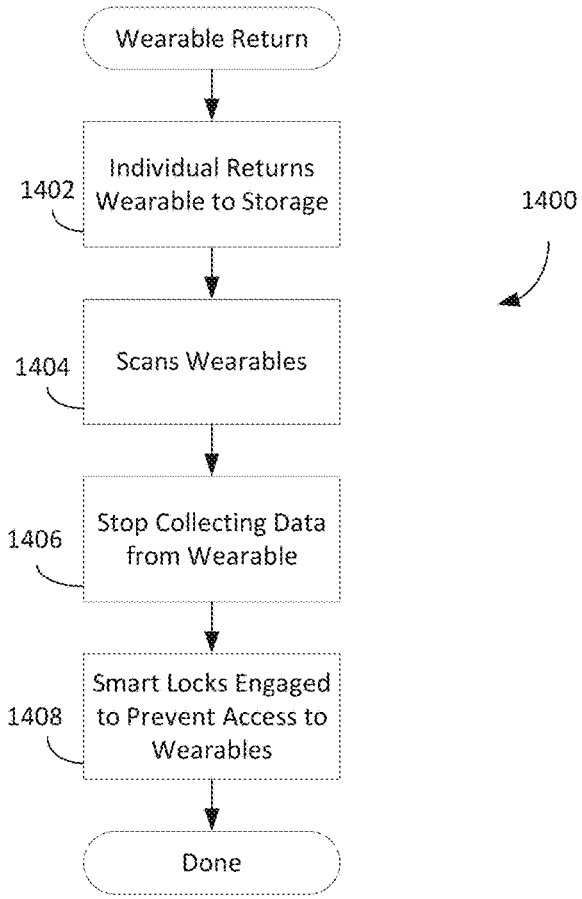
Figures 15, 16A:
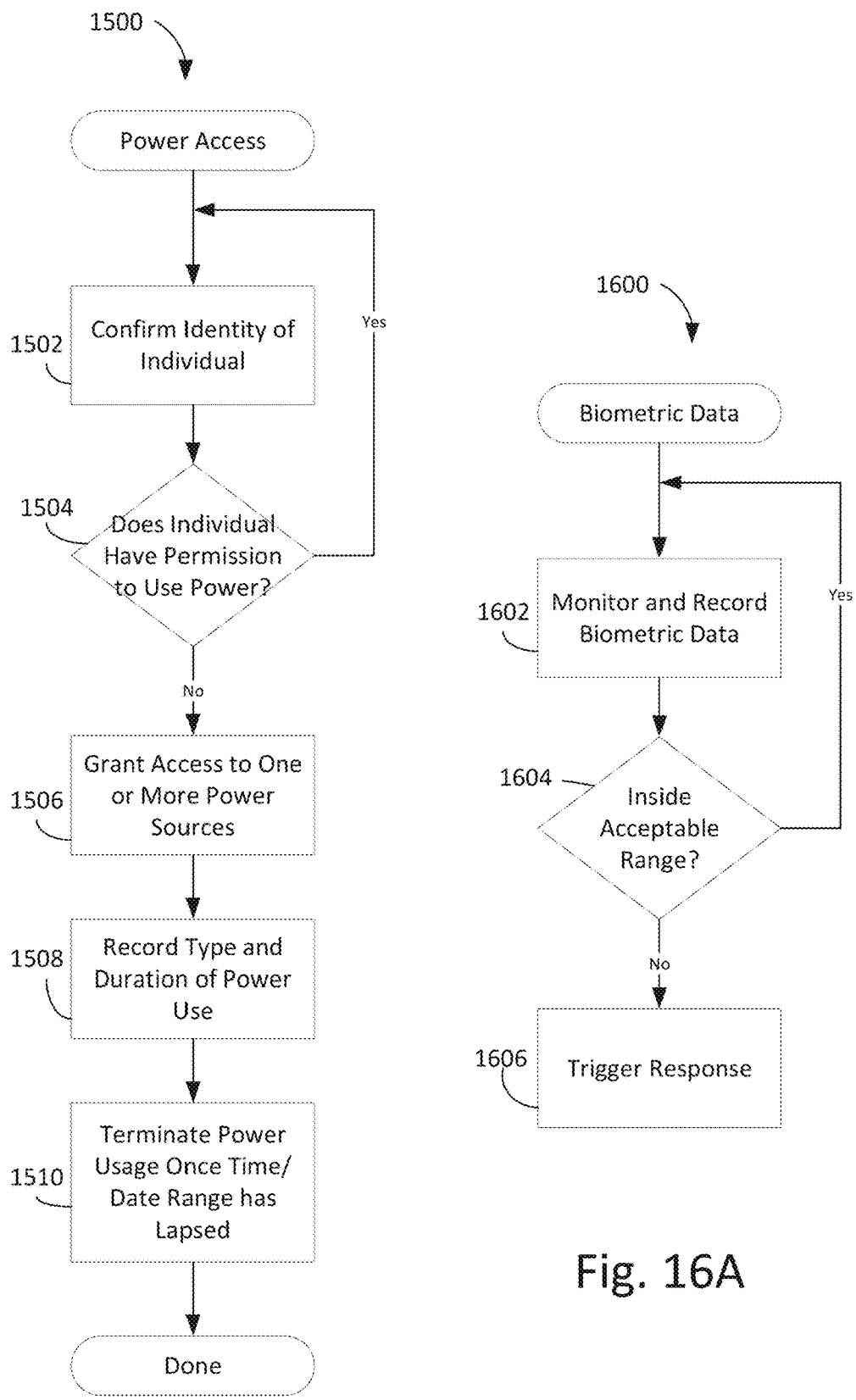
Figure 16B:
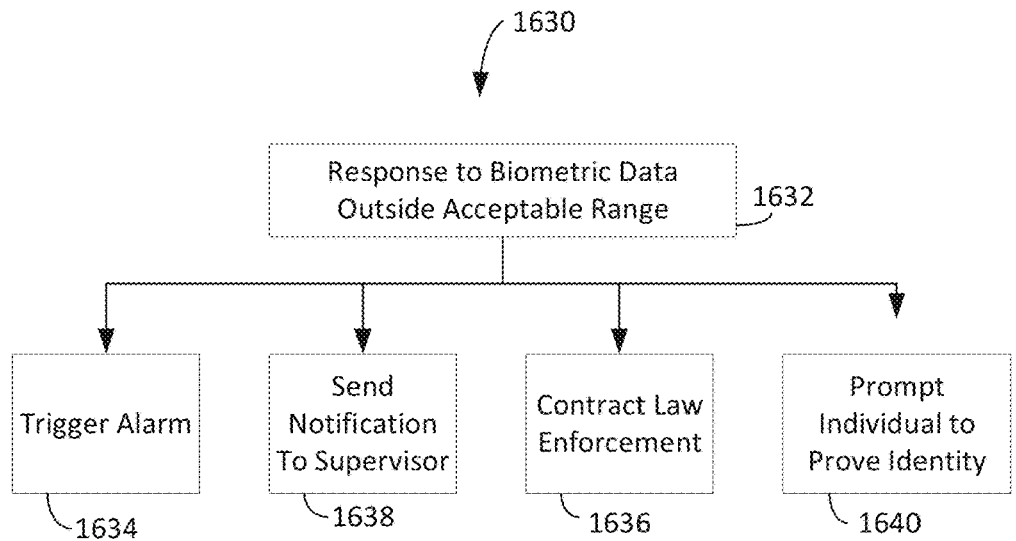

FIG. 12B shows an example of different areas that may be established for geofencing at the project location 1200. Area A shown a boundary 1210 may include the entirety of the project that is under construction 1206. Area B 1212 may be a portion of the project, such as the kitchen. Area C 1214 may be the shed and area D 1216 may be the entire project location. Individuals may have access to none of these areas or to a subset of these areas, including all areas.

When a worker enters an unauthorized area, an audio or video response can occur on the wearable. For example, a smart vest may include lights that may flash or may be continuously illuminated in response to a party being outside the permitted areas on the project location. Another option is for an audio alarm or a video alarm to be triggered at the project location rather than on a wearable. A further option is to send a notification, such as a phone call, a text message, an email message, or other notification to a supervisor on or off the project location. Yet another option is to take disabling measures relative to the individual. The disabling measures could entail triggering locks or disabling equipment by shutting off power or the like. The geofencing can also be used to determine where the material will be delivered, stored, and installed. The geofencing, along with date and time information, can assist with the determination whether the material was handled or installed by a licensed, experienced, approved, authorized, or otherwise preferred worker.

Referring to FIGS. 13-16B, flowcharts of the system including trigger events for alarms, wearables, power access, and biometric data and usage is shown.

Figure 17:
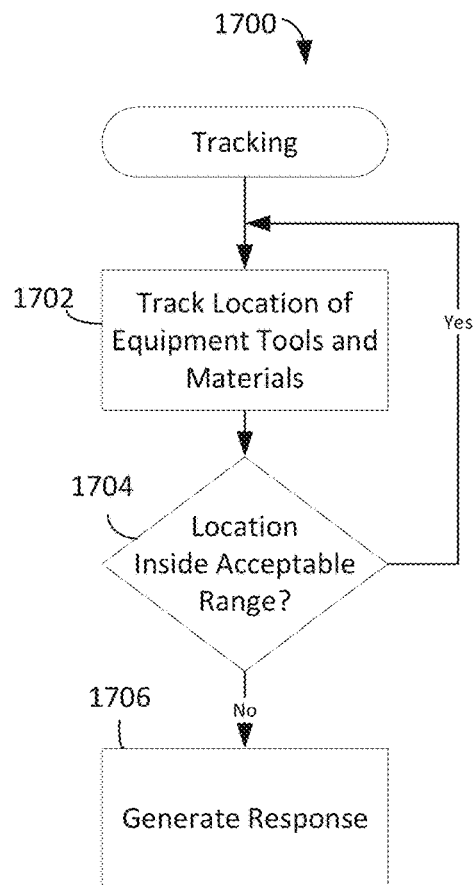
FIG. 17 shows a flowchart illustrating steps that may be performed.

Referring to FIG. 17, the system may track the location of equipment, tools, or materials at the project location 1702. The system can check whether the location of the equipment, tools or materials is acceptable or not 1704. For example, suppose that lumber has been delivered to the project location and the location of the lumber indicates that the lumber is removed from the project location. This would be problematic and would warrant a response. If the location is not acceptable as checked in 1704, a response is generated in 1706.

Figure 18:
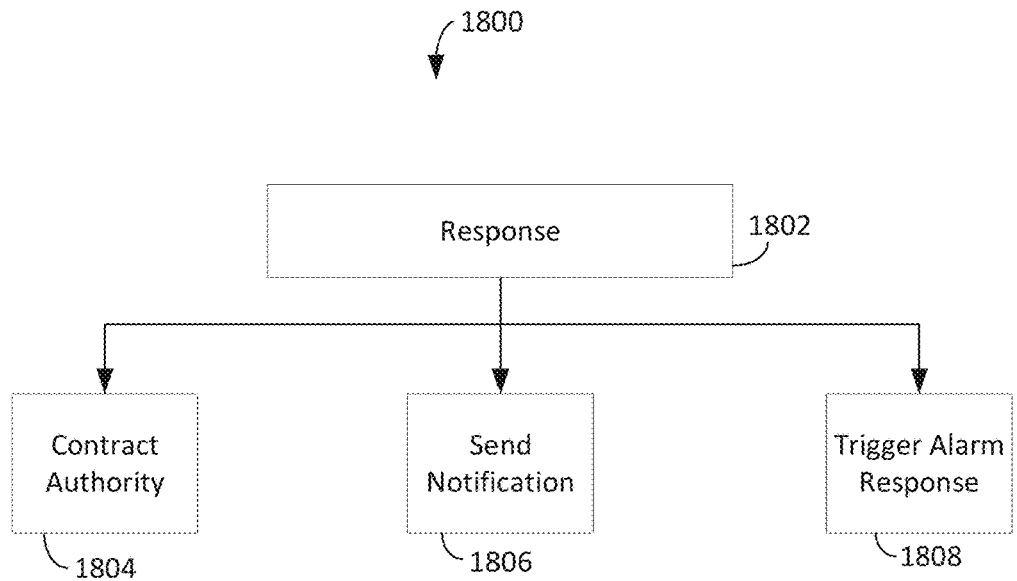
FIG. 18 shows possible responses accomplished by the system.

FIG. 18 shows a diagram 1800 illustrating different types of responses 1802 that may be generated in response to the equipment, tools or material in an unacceptable location. One type of response is to contact law enforcement or security 1804. In many cases the location of the tools, equipment and materials may indicate that a theft is underway. Another type of response is to send a notification to a supervisor or to other appropriate parties at the project location 1806. A final type of response is to trigger an alarm response 1808, such as the sounding of an audio alarm or a video alarm.

Figure 19:
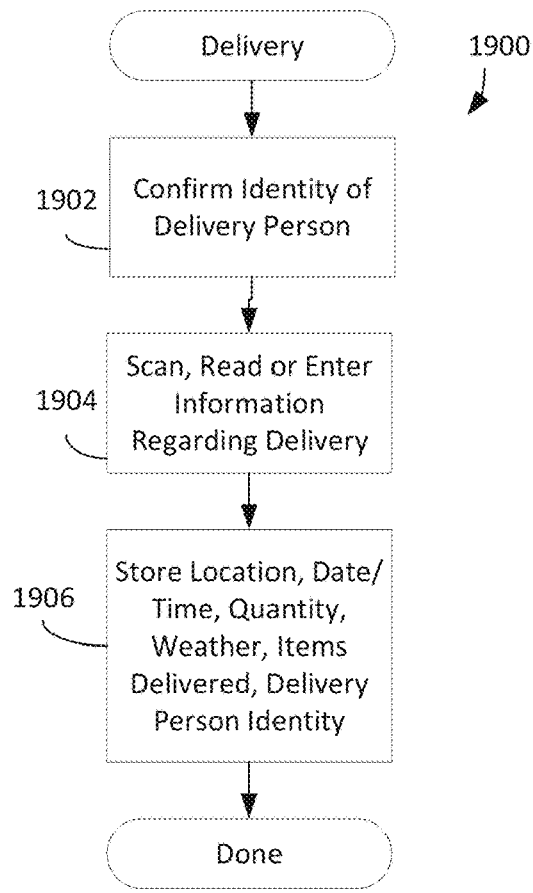
FIG. 19 shows a flowchart illustrating steps that may be performed.

The system helps manage deliveries to the site. FIG. 19 depicts a flowchart 1900 showing steps that may be performed in this regard regarding deliveries. Initially, the identity of the delivery person is confirmed to indicate that the delivery person is the appropriate party and is permitted access to the project location 1902. For example, a serial number or other identification indicator may be scanned or read off the delivered items. In addition, information may be entered by the delivery person using the housing, such as by entering information via screen 106A (FIG. 1A) 1904. The location of delivery, the date of delivery, the time of the delivery, the quantity of the delivery, the identity of the delivery person and the weather may be recorded as part of the information that is kept regarding the delivery. This information can be used to track and confirm deliveries as well as to understand the conditions when the delivery was made.

Figure 20:
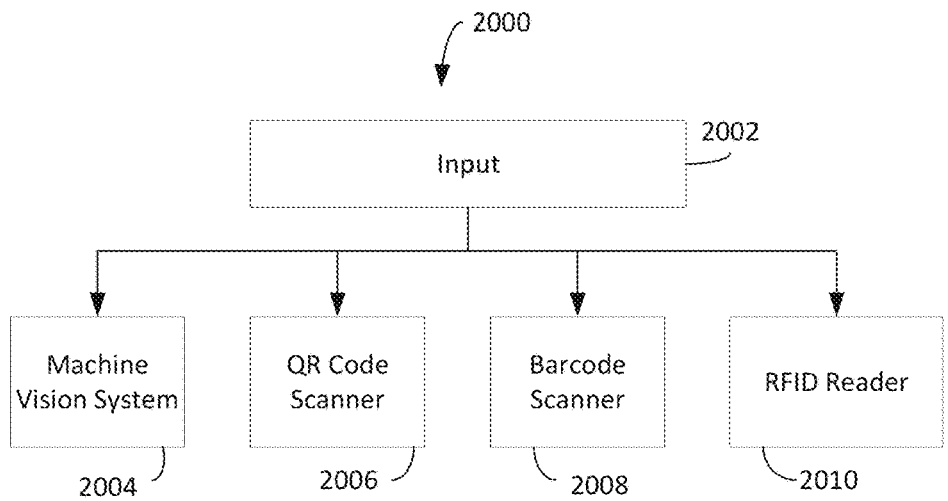
FIG. 20 shows different types of input technology.

The deliveries may utilize various scanning and reader technology. In FIG. 1A, a scanner 110A may be provided. Diagram 2000 in FIG. 20 illustrates different types of inputs 2002 that may be used for assisting gathering information regarding deliveries. A machine vision system 2004 may be provided. The machine vision system 2004 may capture an image of the delivered items and process the image to determine the nature of the items that were delivered as well as the quantity of items. Moreover, the machine vision system may capture an archival image that may be indicative of the state of the items when they were delivered. A QR code scanner 2006 may be used where QR codes are on a delivered items or documentation. Similarly, a bar code scanner 2008 may be used where bar codes are on the items or on documentation delivered with the items. Still further, an RFID reader 2010 may be provided to gather information regarding the delivered items.

Figure 21:
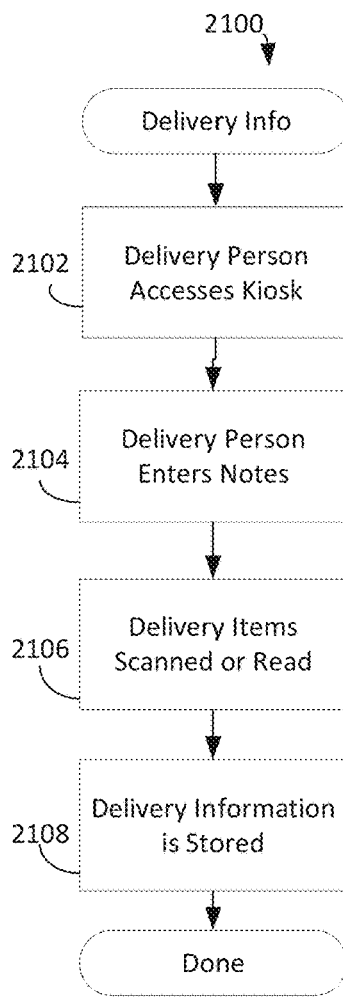
FIGS. 21-26 shows flowcharts of steps that may be performed.

The delivery person may interface with housing via display 106A and 1900 to provide delivery information. Flowchart 2100 of FIG. 21 illustrates some of the steps that may be performed in such an instance. Initially, the delivery person may access the housing 2102. The delivery person may enter a note(s) regarding the delivery, such as what was delivered and the state of the items that were delivered 2104. This information may be entered, such as through the display 106A (FIG. 1A) which can be a touchscreen. The delivered items are imaged, scanned or read 2106. As was mentioned above, a number of different types of input technology may be used on the delivered items. Therefore, delivery information is then stored in records that may be accessed subsequently 2108.

Figures 22, 23:
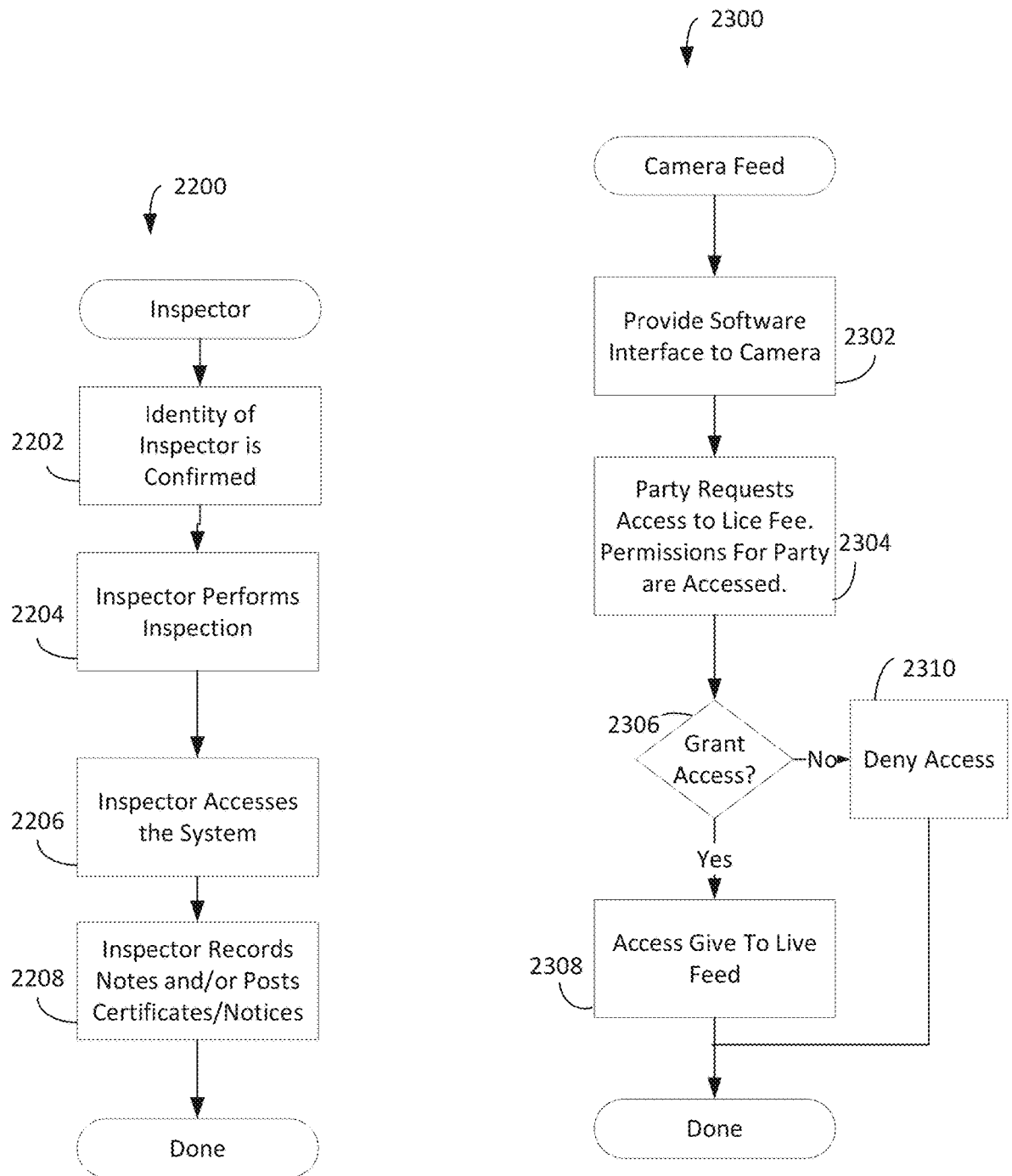

The inspector may interface with the system. FIG. 22 includes a flowchart 2200 illustrating steps that may be performed in such an interaction. Initially, the identity of the inspector may be confirmed using the biometric data 2202 or manually using the touchscreen on the system. The inspector then performs the inspection of the appropriate portion of the project location 2204. The inspector then accesses the system, such as through the system at 2006. The inspector then may record notes and/or post certificates or notices at the system 2208. Additionally, the inspector may use technology available via the system such as OCR scanner or the like to capture appropriate information the inspector may have written during fulfillment of the reason for being on the site.

The system may include a still camera(s) or a video camera(s) that can be included in the system. FIG. 23 provides a flowchart 2300 relating to such access. A software interface to the camera may be provided to enable authorized external parties to gain access to the camera 2302. A party requests access to the camera via the interface over the network 2304. For example, a bank official may wish to view the project location before authorizing release of funds or before granting a loan. A determination is made whether the party is permitted access by accessing permissions 2306. The system gathers a great deal of information over the course of time. At least a portion of this information is persistently stored to compile a record of activities at the project location. This record can be useful to prove activities after the fact. The activities that are recorded may drive workflow and scheduling at the project location to improve efficiency. If the party is permitted access, access is given to the party so that they may receive a captured image or video data 2308. Otherwise, access to the camera by the party is denied 2310.

Figures 24, 25:
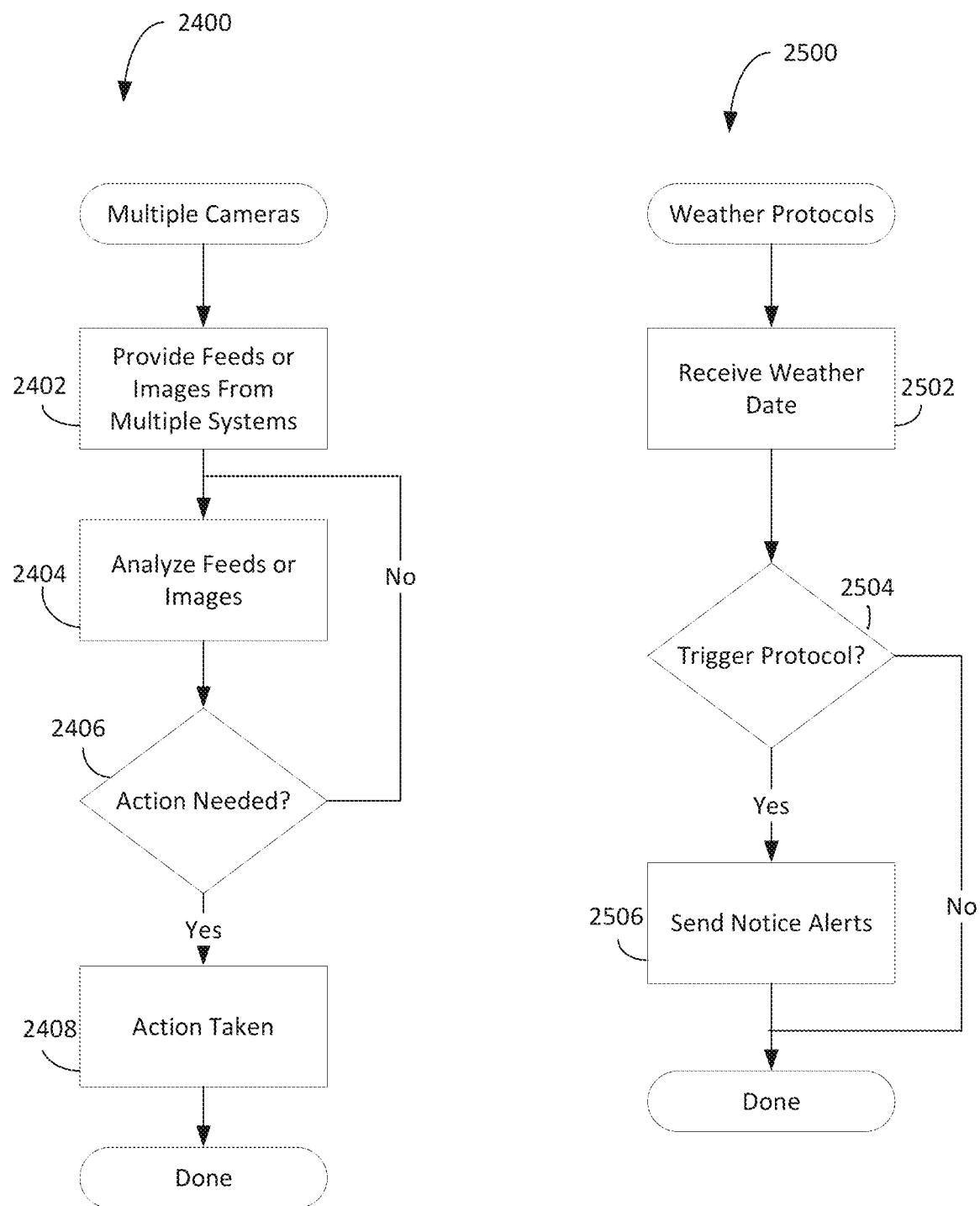

Systems at adjacent locations may be used in conjunction with each other. FIG. 24 shows a flowchart 2400 of steps that may be performed when image capture devices, such as still cameras or video cameras, from multiple adjacently situated systems are used in conjunction in one example application. Video feeds or still images may be obtained from the image capture devices from multiple systems 2402. The video feeds or images may then be processed, such as by the cluster described above, using software such as motion detection software, thermal image analysis or other image analysis software to identify activity that may warrant a response 2404. For example, the analysis may identify a large living object moving near the periphery of multiple project locations. The system may then, based on the analysis, determine if action needs to be taken 2406. If an action is needed, then the action is taken 2408. If not, the capture of the images or videos may continue. Examples of actions include sounding an alarm, contacting law enforcement, contacting a security team or the like.

The environmental conditions, including weather conditions, may trigger different protocols that are performed by the system. For example, inclement weather, very cold weather or very hot weather may trigger protocols to ensure worker safety and productivity as well as the protection of structures, materials, and equipment at the project location.

FIG. 25 shows a flowchart 2500 of steps that relate to such protocols. Initially, the system receives environmental data 2502. A check is made whether the weather data values trigger any protocols 2504. If a protocol is triggered, notices and alerts may be sent as part of the protocol to the appropriate parties 2506. For example, if the temperature is over 90° F., a party may be sent a notice to take a break every hour and to hydrate. Related notices may be sent to supervisors. Such notices can be generated according to the product or material specifications in the material requirement record, when materials are confirming or nonconforming, environmental conditions and other events. For example, if it is too cold, workers may be prompted to wear gloves and hats and to spend time in a heated space every hour. In still another example, if severe weather is approaching, workers may be prompted to secure the project location and seek a safe location. In a final example, workers may be prompted not to take actions, such as pouring concrete, applying paint, or applying stucco, in certain weather conditions.

Figure 26:
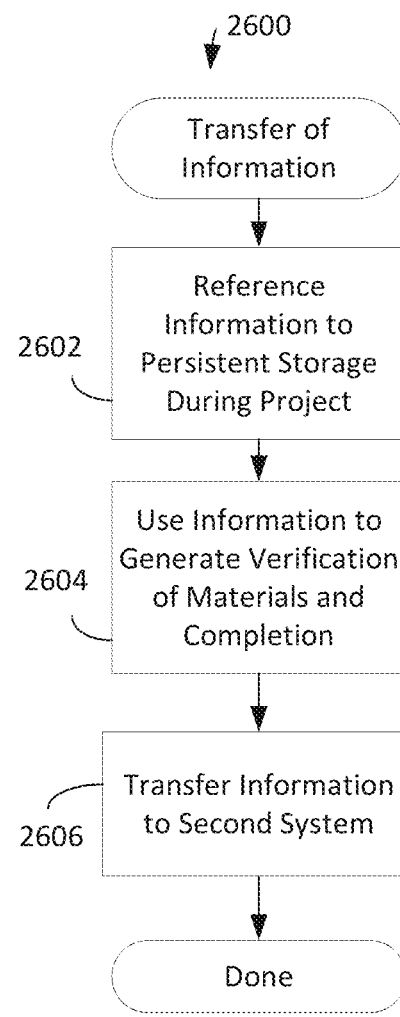

As has been mentioned above, a great deal of information may be collected and stored during the project, process of task for reference during or after the project, process or task is completed. FIG. 26 shows a flowchart of steps 2600 that may be performed in exemplary embodiments in relation to the information. The information obtained during the project from many different sources may be stored on or referenced from persistent storage 2602. The information may be stored on an ongoing fashion, in databases as described below, and may be referenced in an immutable persistent fashion on the storage. This information may help resolve disputes between parties involved on the project or process. For example, suppose the assembler asserts that the wrong items were delivered. Since there is a complete record references on the persistent storage of all deliveries, these records may be accessed to resolve the dispute. Insurance providers may access injury records referenced on the persistent storage to settle or confirm claims. Disputes regarding pay among workers may be resolved by checking the recorded hours on site to determine the appropriate pay for the workers. Inspection records may be accessed to confirm that proper inspections were carried out and passed.

When the project or process is complete, information referenced on the persistent storage may be extracted and encapsulated into a certification of materials and completion 2604. The certificate of completion can be created based upon the housing receiving a set of completion criteria from the regulatory entity and a financial entity, determining whether the set of compliance criteria has been met according to the certificate of regulatory compliance, the certificate of materials the certificate of inspection, a payment information representing that payments have been satisfied, and occupancy requirements have been met. The certificate of completion can be stored on the persistent storage.

The record may hold information such as the design, materials requirements, actual material delivered, worker sequence information, installation instructions, warranties for items in the completed project or process, confirmation of conditions and qualifications at the time of installation for warranty, punch list completion information, lender information, information regarding workers, insurance policy information, inspection history information, ownership history, history of localized events; like weather and records of trespassing (such as images), and bills of lading for items delivered during the project.

The advantages of this system can be shown by way of example. Suppose that an oven in a home fails three months after an owner occupies the premises. Since the persistent storage has information concerning the manufacturer, design, supply, delivery, installation and inspection of the oven, complete warranty information is available, the owner, supplier or repair entity can reference the persistent storage to have the oven repaired or replaced. In another example, suppose that gutters on the home leak six months after an owner occupies the premises. The owner can reference the persistent storage, assembler or manufacturer warranty and repair or replace the gutters. The assembler might also have a remedy against the installation worker, based on evidence that materials were not installed properly, the manufacturer guidelines were not followed, conditions precedent were not met or other errors or omissions. Further, the shipping delivery record may indicate that the materials delivered were different from those specified in the material requirements record.

The information referenced in the persistent storage may also be accessed from a computing device of an owner, end user, customer, integrated and the like at 2606. The computing device may be, for example, part of a home maintenance system that manages and controls home systems, such as heating, air conditioning, lighting, an alarm system, or the like. The computing device may be part of a smart home controller and may interface with appliances and other items that are interconnected via a home control network. The computing device may include a document management system for securely storing the transferred information. The computing device may be a facilities management system, or operations system associated with the project location.

In exemplary embodiments, information may be gathered from and sent to multiple parties including a managing company responsible for the management and oversight of the project or process, a design company responsible for developing a design for the home and developing the material requirement record for the project or process, a supply company which analyzes the design and materials for the project or process, and the individuals or entities responsible for performing and completing the project or process.

Figure 27A:
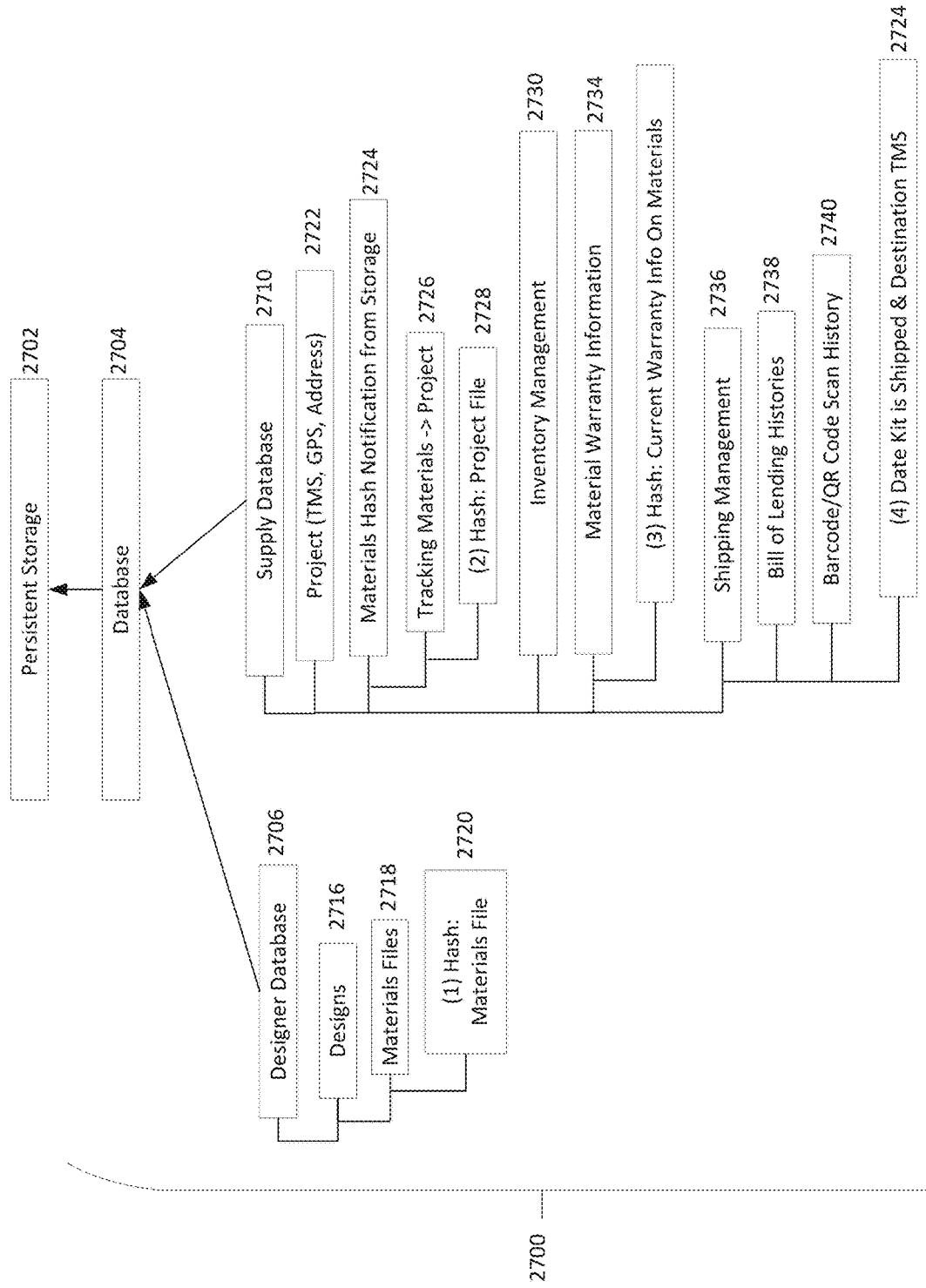
FIGS. 27A-27B shows databases that provide reference information.
Figure 27B:
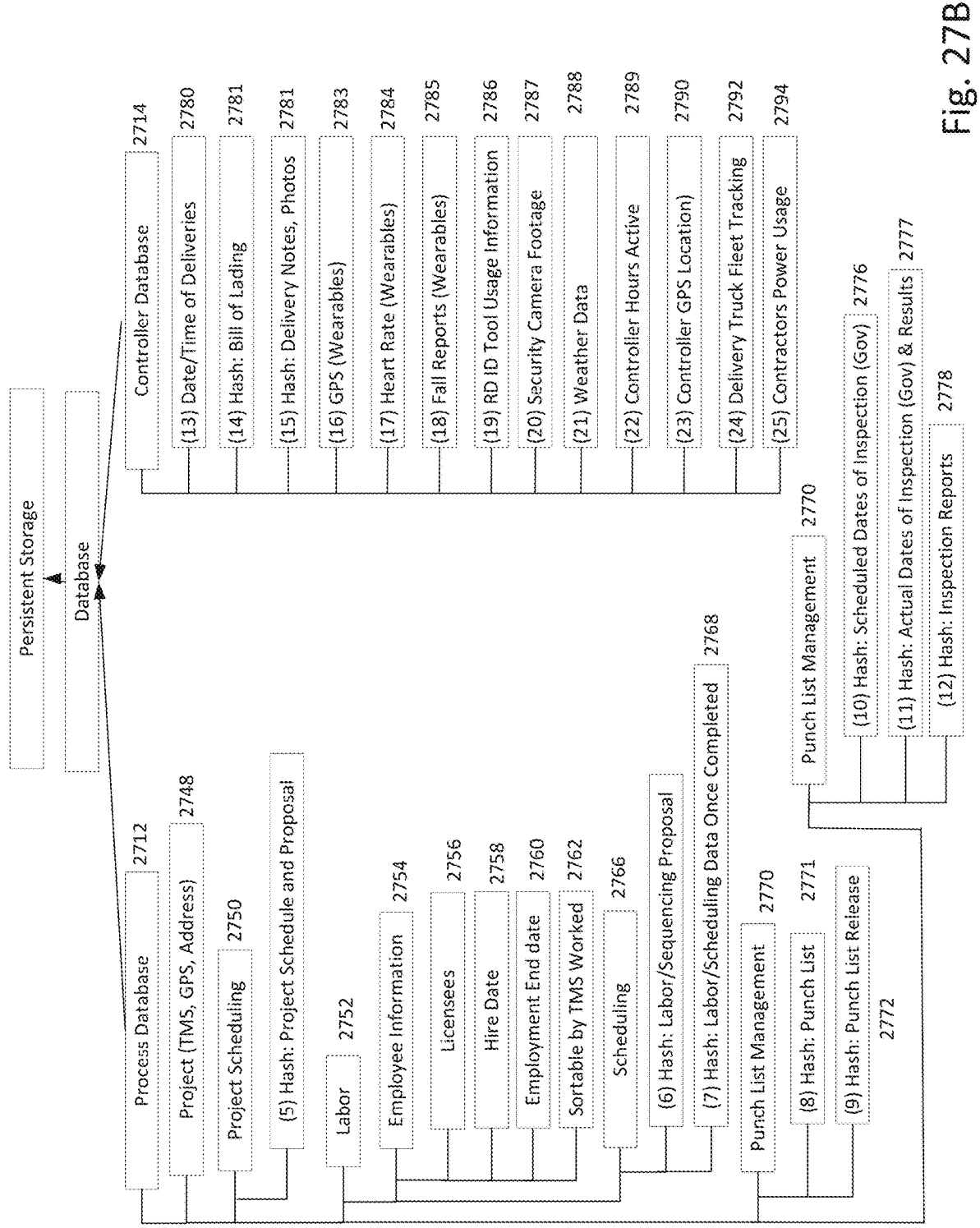

FIGS. 27A and 27B show a diagram 2700 depicting possible information from multiple data sources (e.g., databases), some of which may be referenced on the persistent storage 2702. The workflow may be that the data is first stored in a management company database 2704 and then referenced on the persistent storage 2702. The design company database 2706 may hold information that is passed on to the management company database 2704 and ultimately referenced on the persistent storage 2702. The design company database 2706 may hold designs 2716. The designs 2716 may include design and material files as has been discussed above. A hash value resulting from passing the material requirement record file 2720 for the project or process through a secure hash algorithm may also be stored on the design company database 2706. The material requirement record file may be hashed using any number of different types of known secure hash algorithms as mentioned above. The hash value of the material requirement record file may be transferred to the management company database 2704 and then for reference on the persistent storage 2702.

FIGS. 27A and 27B also show a supply company database 2710. The supply company database 2710 may hold project information 2722, such as tax map submap (TMS) numbers, GPS data and addresses for project or process properties. The supply company database 2710 may store a material requirement record hash notification 2724 from the persistent storage 2702, indicating that the hash value for the material requirement record has been referenced on the persistent storage 2702. Information 2726 tracking the material requirement record may be stored in the supply company database. As was discussed above, the supply company may analyze and process the design to develop the material requirement record for the project or process. A hash value 2728 resulting from passing the design file through a secure hash function is stored in the supply company database 2710, transferred to the management company database 2704 and referenced on the persistent storage 2702.

The supply company database 2710 may also store inventory management information 2730, such as quantity and the particulars of material inventory and material warranty information for such materials 2732. The warranty information for materials used in the project may be hashed 2734 and the resulting hash value may be stored in storage in the supply company database 2710. The hashed value 2734 may be passed to the management company database 2704 and then referenced on the persistent storage 2702. The supply company database 2710 may also store shipping management information 2736. This may include bill of lading histories 2738 and barcode, RFID values, UHF values and/or QR code scan histories 2740. The material list (such as a bills of lading) for an assembly project and the barcode/QR scan codes for delivered items for the projects may be hashed 2742 and the resulting hash value(s) passed to the management company database 2704 for reference on the persistent storage 2702. Further, confirmation of what was specified by designers was delivered to the project location and installed according to the manufacturer's specifications so that a project or process can be placed under warranty.

An assembler database 2712 may store project information 2746, such as TMS #'s, GPS data and addresses for projects. The assembler database may also hold scheduling information 2748 for the project. This may include detail regarding workflow and timing. A hash value of the project schedule 2750 may be stored on the assembler database 2712, passed to the management company database 2704 and referenced on the persistent storage 2702. The assembler database 2712 may store worker information 2752. The worker information 2752 may include employee information 2754 for workers involved in projects. This employee information 2754 may include information regarding licenses for workers 2756, hire dates for workers 2758, employment end dates for workers 2760 and other information, such as names, photos, etc. The worker or laborer information can include information that the worker or laborer is in compliance with applicable laws (including federal and state), in compliance with contractual obligations, properly licensed, of legal status, of sufficient experience, within application restrictions such as a limit on hours worked during a 24 hour period, authorized for the project location and any combination. The worker or laborer information may be sortable by keys such as TMS # to identify workers for a project. The assembler database 2712 may also store scheduling information 2764 for workers. This information may be used to develop a worker/sequencing proposal that is hashed 2766 and the resulting hash value stored in the assembler database 2712. The hash value 2766 may be passed to the management company database 2704 and referenced on the persistent storage 2702. Worker sequencing data once the labor is completed 2768 may be hashed and the resulting hash value stored in the assembler database 2712 for a project. This hash value 2768 may be passed to the management company database 2704 and referenced on the persistent storage 2702.

Punch list management information 2770 may also be stored in the assembler database 2712. The punch list management information 2770 may include a hash of the punch list for a project 2771 and a hash of punch list releases for a project 2772. These hash values 2771 and 2772 may be passed to the management company database 2704 and referenced on the persistent storage 2702. The punch list information can be used for a determination of warranty requirement compliance.

Inspection management information 2774 may be stored in the assembler database 2712. Hashes of scheduled dates of inspections 2776, dates of actual inspections and results 2777 and failed inspection reports 2778 for a project may be stored in the assembler database. The hash values 2776, 2777 and 2778 may be passed to the management company database 2704 and referenced on the persistent storage 2702.

Hash values gathered and stored in the site supervisor database 2714 may be passed to the management company database 2704 and referenced on the persistent storage 2702. This may include hash values of information regarding dates and times of deliveries for a project 2780, delivery details for the project 2781 and delivery notes and delivery photos for the project 2782. The hash values may include hash values resulting from passing GPS information for wearables used in the project 2783, heart rate information gathered by wearables for the project 2784, failure reports from the wearables for the project 2785 through hash functions. Additionally, hash values resulting from passing RFID tool usage information for the project 2786, security camera footage gathered by the site supervisor for the project 2787, weather data recorded by the site supervisor for the project 2788, hours information for when the site supervisor was active for the project through hash algorithms may be stored in the site supervisor database 2714, passed to the management company database 2704 and referenced on the persistent storage 2702. The values may also result from passing GPS location information for the system 2790, tracking information for delivery trucks 2792 and worker power usage information 2794 through a hash function. Hash values 2790, 2792 and 2794 may be passed to the management company database 2704 and referenced on the persistent storage 2702.

Figure 28:
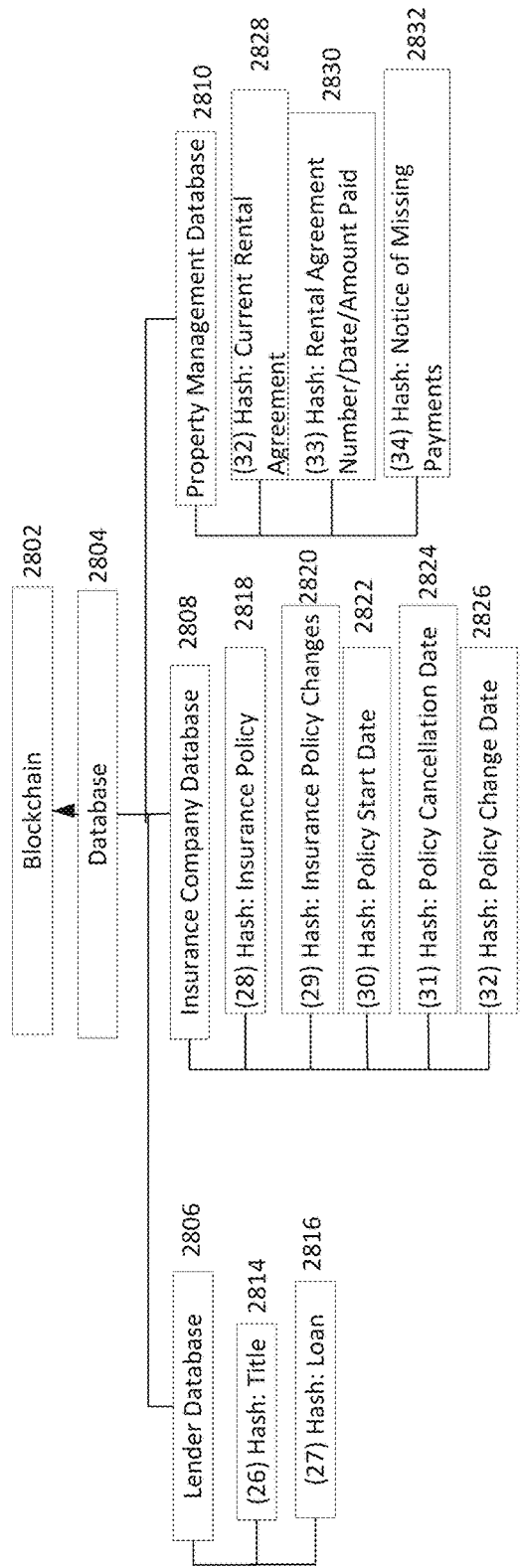
FIGS. 28-29 shows informational flow of the system.

Information referenced on the persistent storage may originate from third parties. FIG. 28 shows a diagram 2800 of additional sources of information from other stakeholders. For example, information may originate from a lender database 2806. For example, hashed versions of a deed for a building 2814 and the mortgage 2816 on the project location property may be stored in the lender database 2806, transferred to the management company database 2804 and referenced on the persistent storage 2802.

Information may originate from an insurance company database 2808. A hash of an insurance policy for the project 2818, a hash of any insurance policy changes for the project 2820, a hash of policy start date 2822, a hash of policy cancellation date 2824 and a hash of policy change dates 2826 may be stored in the insurance company database 2808. The resulting hash values 2818, 2820, 2822, 2824 and 2826 may be transferred to the management company database 2804 and referenced on the persistent storage 2802.

Information may also originate from a property management database 2810. Hashes of a current rental agreement 2828, rental agreement particulars 2830 (such as agreement number, dates and amount paid) and notice(s) of missed payments 2832 may be stored therein. Information can include utility consumption and expenses such as insurance, taxes, maintenance, and the like.

The hash values 2828, 2830 and 2832 may be added to the management company database 2804 and ultimately referenced on the persistent storage 2802.

Figure 29:
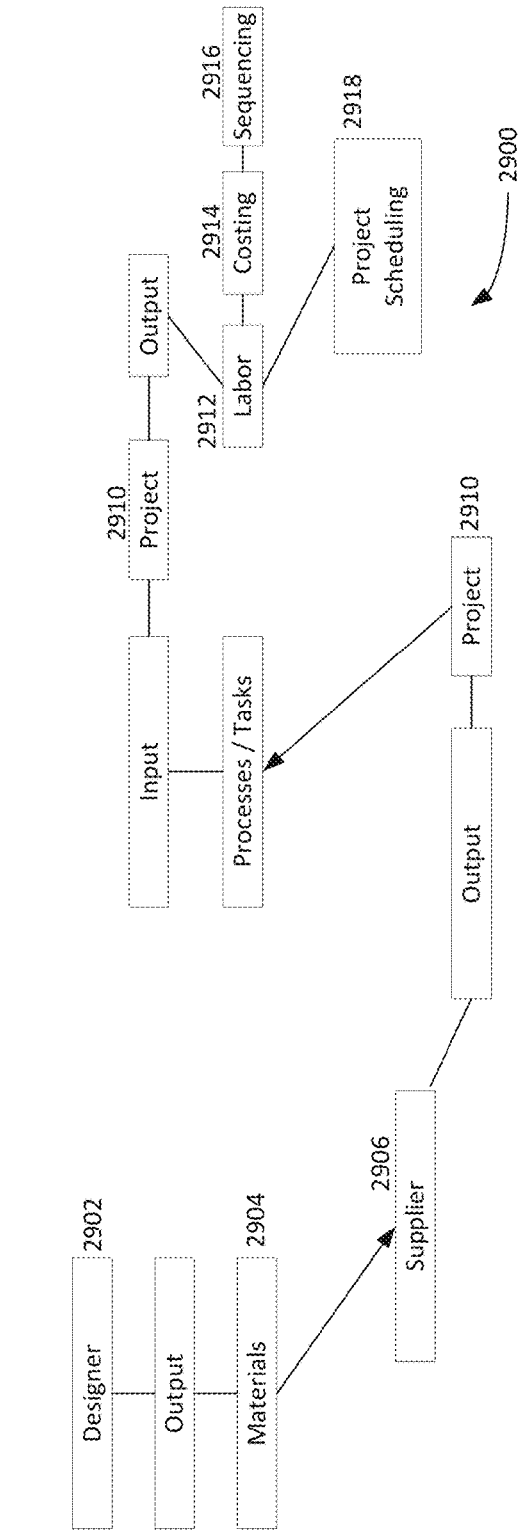

FIG. 29 shows a diagram 2900 that captures information flow among the design company 2902, the supply company 2906 and the assembler 2912. As was mentioned above, the design company 2902 generates a design 2904 for the project or process that is passed to the supply company 2906. The supply company 2906 uses information in the design 2904 to generate the material requirement record 2910. The design 2910 is then shared with the assembler 2912. The assembler 2912 develops a project schedule 2918. The project schedule 2918 specifies labor needs 2912 for the project, the costs for the labor 2914 and the sequencing of labor 2918 over the project.

Figures 30, 31:
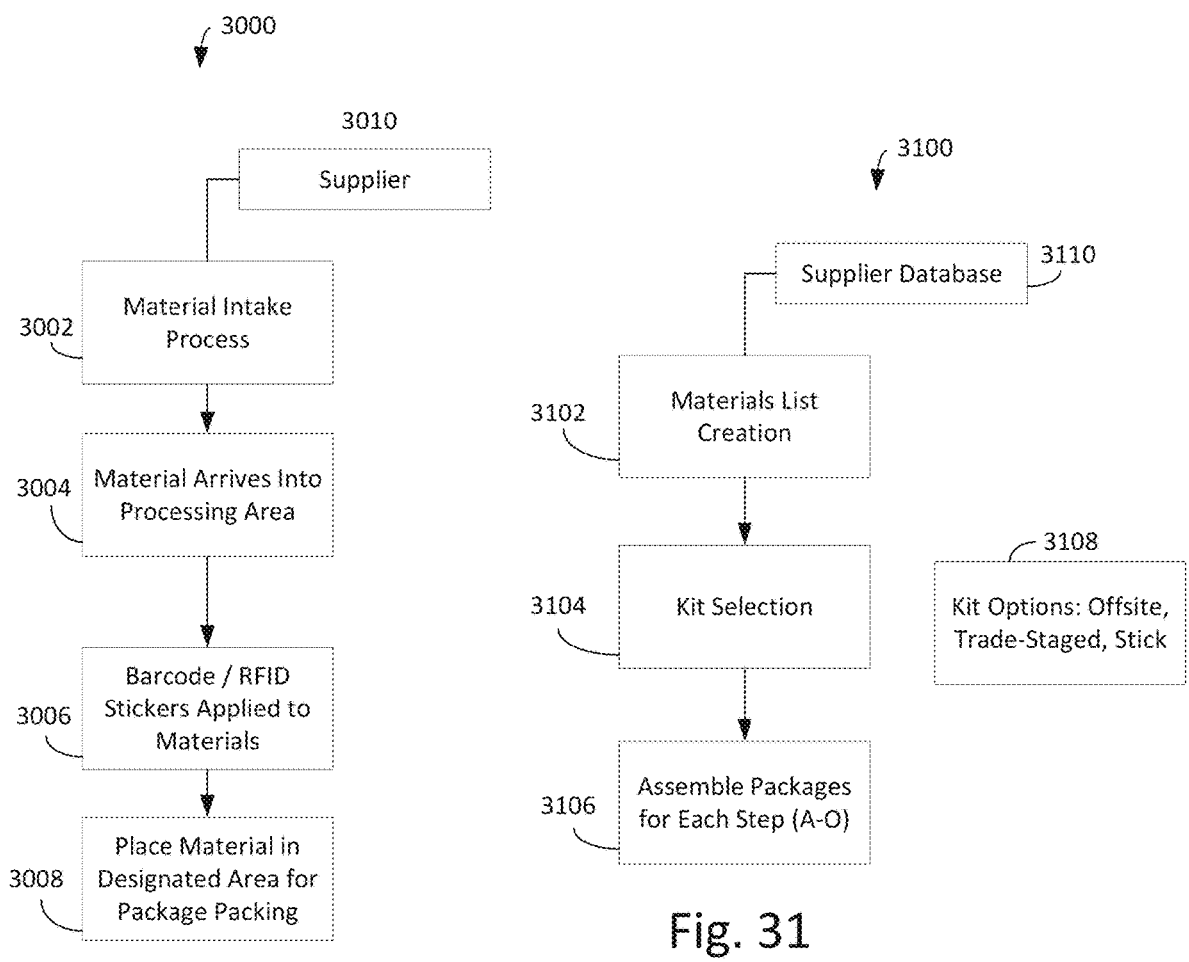
FIGS. 30-31 shows flowcharts of operations performed by system.

The supply company 3010 is responsible for the intake of materials specified in the material requirement record that are needed for the project or process. FIG. 30 shows a diagram 3000 of steps taken in the material intake process 3002. Materials arrive 2914 at a processing area of the supply company 3010 from the manufacturers and/or distributors. Items such as barcode stickers, QR code stickers, Bluetooth beacons, UHF stickers and/or RFID stickers are applied to the materials 3006 so that the materials may be identified and tracked. The materials with the stickers applied are placed in a designated area for packing 3008. The materials may then be packaged for shipment to the project location.

As shown in the diagram of FIG. 31, the materials may be organized into kits for activities at the project location. The material requirements record 3104 is created 3102 and processed to develop the set or group of materials that will be sent to the project location. Different strategies 3108 may deployed to develop the set of materials. For example, the materials in the set may be staged based on the trade involved (e.g., electrical, plumbing, carpentry) so that each trade has its own set for the stage of construction. Thus, sets are selected 3104, and packages are developed for each step or stage of the project or process 3106.

Figure 32:
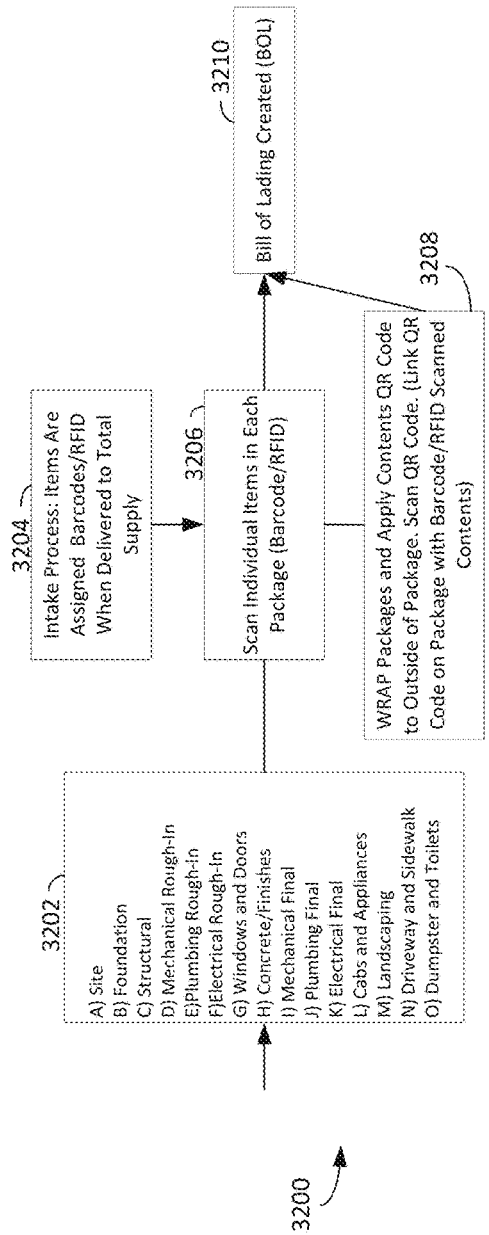
FIGS. 32-33 shows examples smart contracts.

FIG. 32 shows a diagram 3200 depicting additional detail of activity performed by the supply company. The project or process schedule 3202 is organized into stages, such as site preparation, foundation, etc. as shown in FIG. 32. Items may be affixed, such as barcodes, QR codes, RFID identification, Bluetooth beacons and/or UHF identification when the items arrive at the supply company 3204. As was mentioned above, stickers may be affixed to the items to associate the codes with the items. The items in each package may be scanned to record what items are included in the packages 3206. The packages may be wrapped as needed and a QR code sticker may be affixed to the outside of each package 3208. The QR code for each package is scanned 3212. The process may then generate a material list for each delivery 3210.

Figure 33:
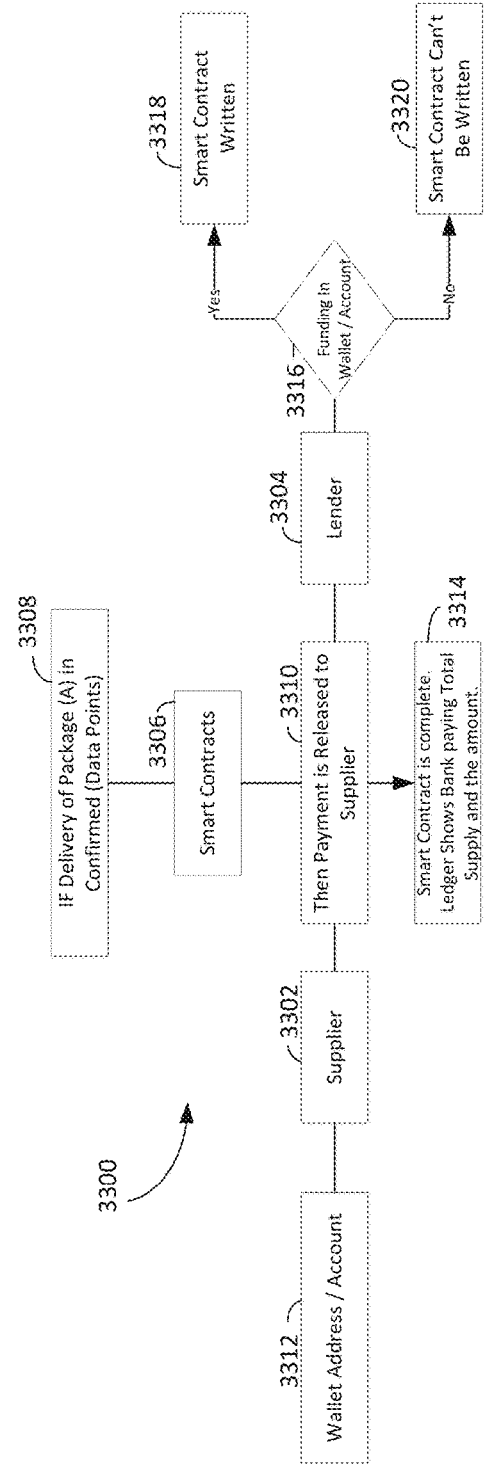

FIG. 33 shows a diagram 3300 of a first example of interactions relating to a smart contract for the project or process. Suppose that the supply company 3302 makes a delivery to the project location. Further suppose that the delivery is confirmed 3308 by information such as that gathered by the system as discussed above. The lender 3304 then releases payment 3310 to the supply company 3302. Payments can be made through third party funding, factoring, credit lines, loans, or other financial option to assist with financing and cash flow management.

The payment may be made electronically, such as through crypto currencies, like Bitcoin or Ether, or via a stable coin whose value is pinned to an item like a paper currency or the like. A cryptocurrency is a digital currency built with cryptographic protocols that make transactions secure and difficult to forge. Other Suitable forms of electronic payment includes Automated Clearing House (ACH) payment, Electronic Funds Transfer (EFT), card payments, other types of bank transfers or other types of electronic wallet transfer. In the case where crypto-currency is used, the crypto-currency may be delivered to the digital wallet of the supply company at a specified wallet address or account 3312. The ledger may be updated to show that the contract is complete 3314. Payment requires that the lender has sufficient funding in their digital wallet 3316. If not, the smart contract will not be written on the persistent storage 3318. If there is sufficient funding, payment is made, and the contract is written onto the persistence storage as complete at 3320.

Figure 34:
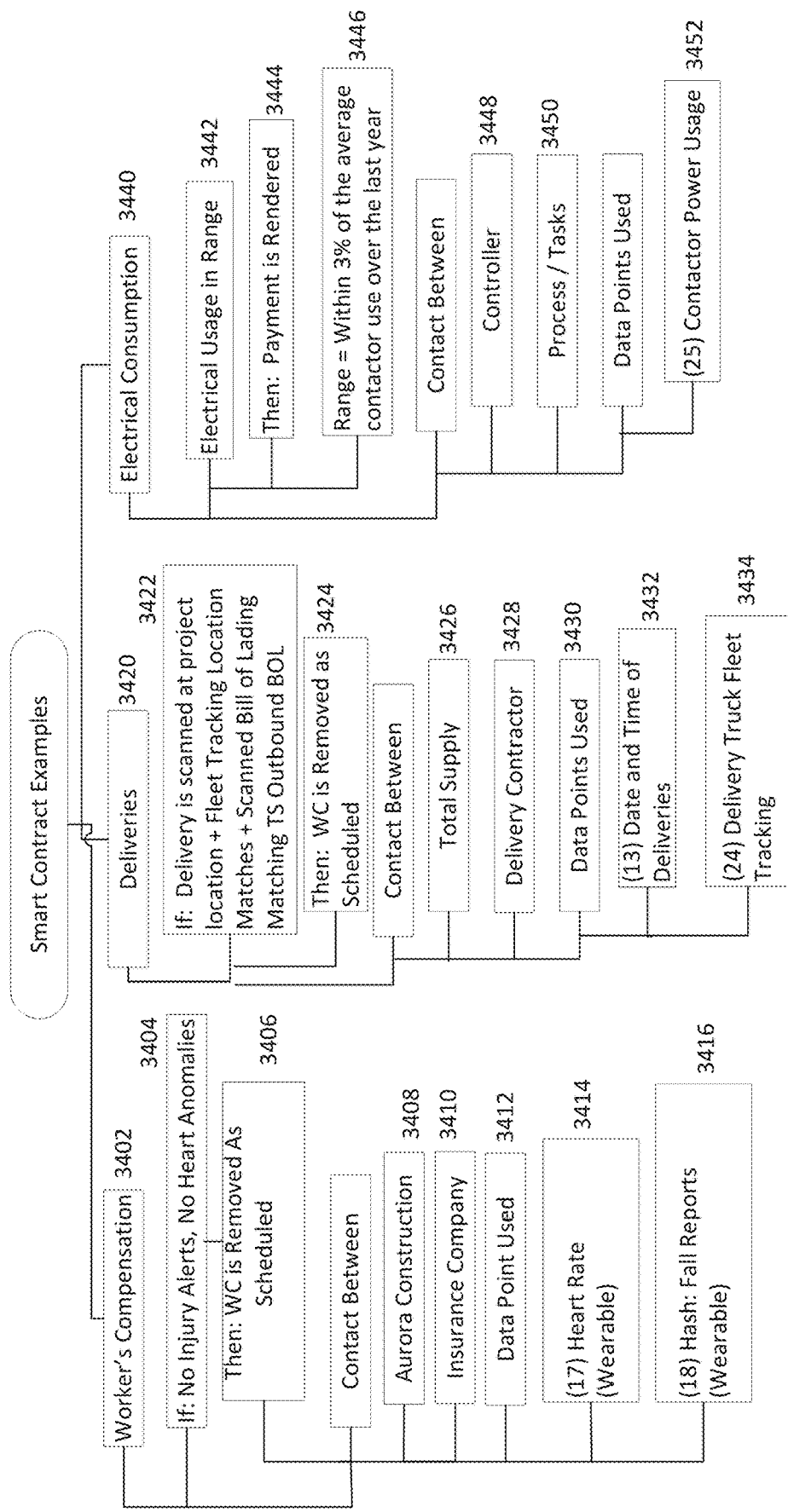

FIG. 34 depicts a diagram 3400 for multiple illustrative smart contracts. In a first illustrative smart contract, the smart contract concerns worker's compensation insurance 3402. The contract removes the insurance for a worker 3406 if there are no injury alerts and no heart rate abnormalities for a given worker 3404. The smart contract can be between entities such as employers (e.g., an assembler) 3408 and an insurance company 3410. The contract looks at the data points 3412 of the heart rate history 3414 gathered by a wearable for the worker and any fall reports 3416 from a wearable for the worker. As mentioned above, the wearables may include a gyroscope or other mechanism that provides data indicative of a fall. This data may be processed to identify data indicative or a fall or other incident where an injury may have occurred.

A second illustrative smart contract shown in FIG. 34 relates to payment for a delivery 3420. If a scan is made at the delivery site, if the fleet location tracking information matches the desired delivery site location and if the scanned material list at the delivery site matches the outbound material list from the supply company 3422, then payment from the supply company 3426 to the delivery worker 3428 is made. Data 3430 used by this illustrative smart contract 3430 includes date and time of deliveries 3432 and delivery truck fleet tracking information 3434.

A third illustrative smart contract shown in FIG. 34 relates to electrical consumption 3440. If the electrical usage by a worker of the assembler is within a range of 3% of the average worker use over the past year 3442 and 3446, then payment is provided 3444 by the assembler 3450 to the system 3448. Power usage data 3452 can be reviewed.

Figures 35, 36:
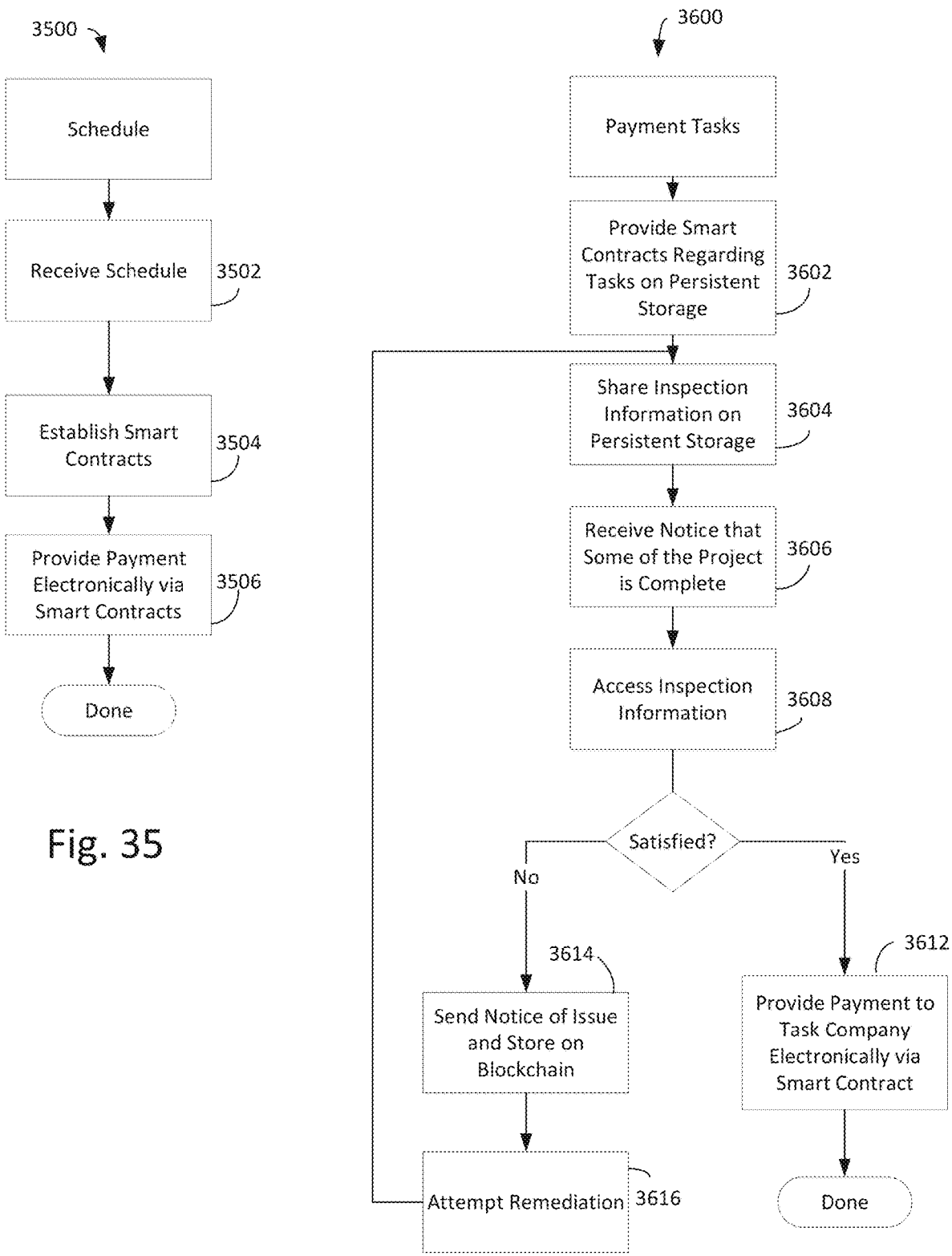

There can be a relationship between the smart contracts and the project schedule. FIG. 35 depicts a flowchart 3500 illustrating steps performed relating to the project schedule and smart contracts. Initially, the project schedule is received 3502. As was discussed above, the assembler forms the project schedule based in part on the design and material requirement record. Based on the project schedule, smart contracts may be constructed that use the persistent storage for contractual arrangements associated with the project or process 3504. The smart contracts are implemented in software and in this case are used to provide electronic payments to parties 3506 for activities relating to the project or process using, for example, electronic payments, crypto currencies, fiat currencies and other forms of payments. The smart contracts may specify the conditions required for payment and may specify the amounts of payment.

FIG. 36 shows a flowchart 3600 depicting steps performed for construction work in the project or process. Initially a smart contract may be initiated that uses the blockchain-based distributed ledger, where the smart contract is for at least a portion of the construction work for the project or process 3602. An inspection of work performed under the contract takes place and information regarding the inspection is passed through a hash function resulting in a hash value. The hash value may be referenced on the blockchain-based persistent storage 3604. The information may include, for example, the name of the inspector, the date of the inspection, an identification of what was inspected, an indication of whether the inspection was passed, any inspection notes from the inspector and an identification of any defects that cause a failed inspection and how to remedy. A notice is received at the system that a portion of the project is complete 3606. The inspection information is assessed 3608. If the inspection information indicates that the inspection was passed 3610, then payment may be provided 3612 to the assembler via smart contract for the portion of the project or process. In contrast, if the inspection was unsuccessful, a notice of the failure and a notice of issues that need to be addressed may be sent, hashed and resulting hash value may be referenced on the blockchain-based persistent storage 3614 for review by the assembler. The assembler may then attempt to remediate the problems 3616 and repeat the above described steps beginning with a new inspection and reference to a hash value for information regarding the new inspection on the persistent storage 3604.

Figures 37, 38:
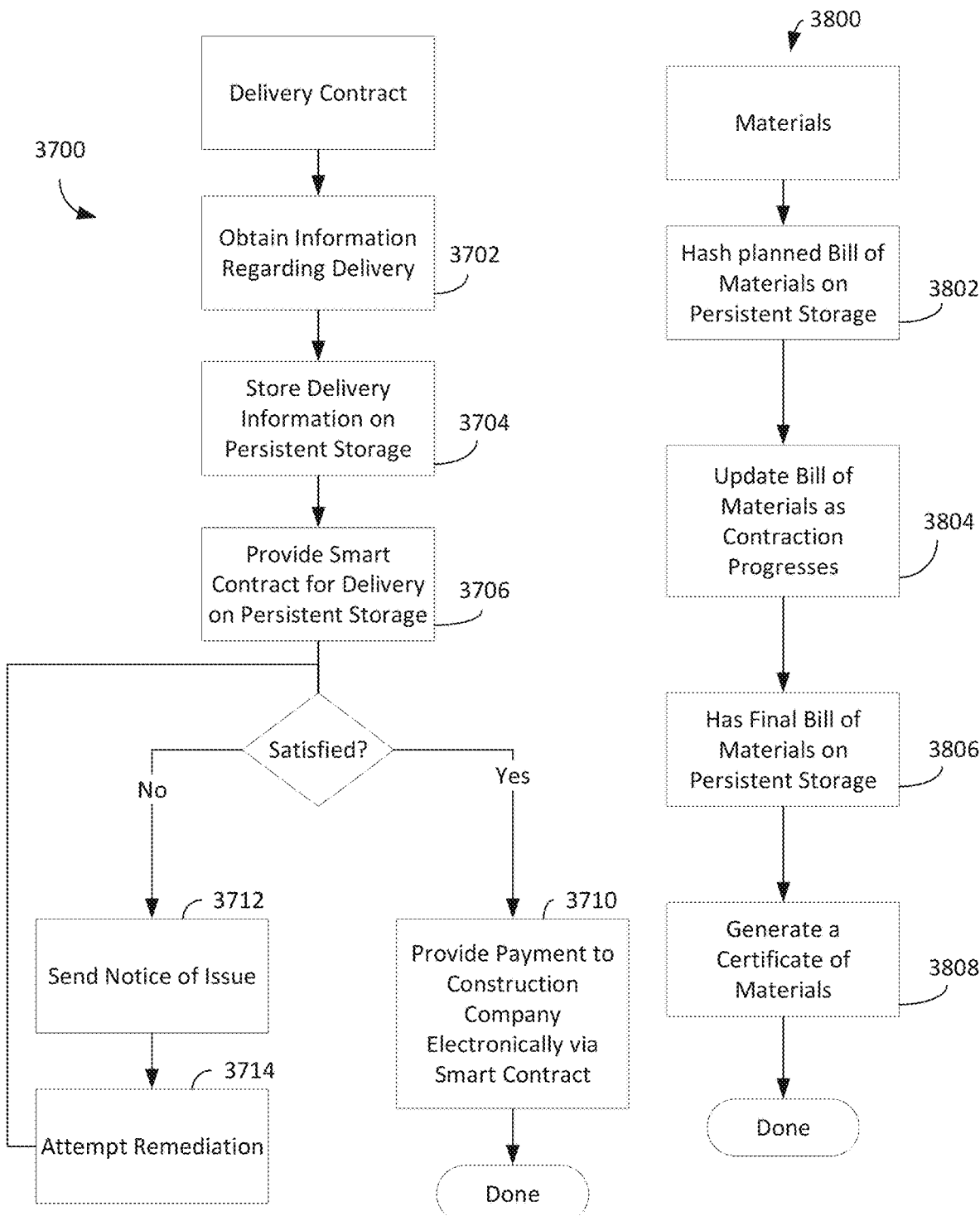

Smart contracts may also play a role with deliveries. FIG. 37 provides a flowchart 3700 concerning steps performed in relation to deliveries relating to such smart contracts. First, delivery and/or materials information is obtained regarding delivery to the project location for the project or process 3702. The information obtained can include if the materials delivered match the material requirement record, manufacturer, and/or supplier which can be confirmed by multiple parties.

The delivery information is hashed, and the resulting hash value is referenced on the blockchain-based persistent storage 3704. A smart contract is provided that uses the persistent storage 3706. A determination is made whether the conditions specified in the smart contract are satisfied 3708. If the conditions are satisfied, electronic payment for the delivery is realized 3710. If the conditions are not satisfied, notice of outstanding issues are sent and the delivery worker may attempt to remedy the issues 3714. The process may then repeat beginning with step 3708 until the conditions are satisfied.

One of the benefits of the approach adopted by the exemplary embodiments described herein is that a complete record of materials used in the home of the project or process is maintained. FIG. 38 shows a flowchart of steps that are performed regarding such materials. Initially, the planned material requirement record generated by the supply company is hashed and the hash value is referenced on the blockchain-based persistent storage 3802 as described above. The material requirement record is updated as the construction progresses until the construction is complete 3804. When construction is complete, the final material requirement record is hashed, and the hash value is referenced on the blockchain-based persistent storage 3806. The information in the final material requirement record is used to generate the certificate of materials provided to the owner of the home resulting from the project or process 3808.

Figures 39, 40:
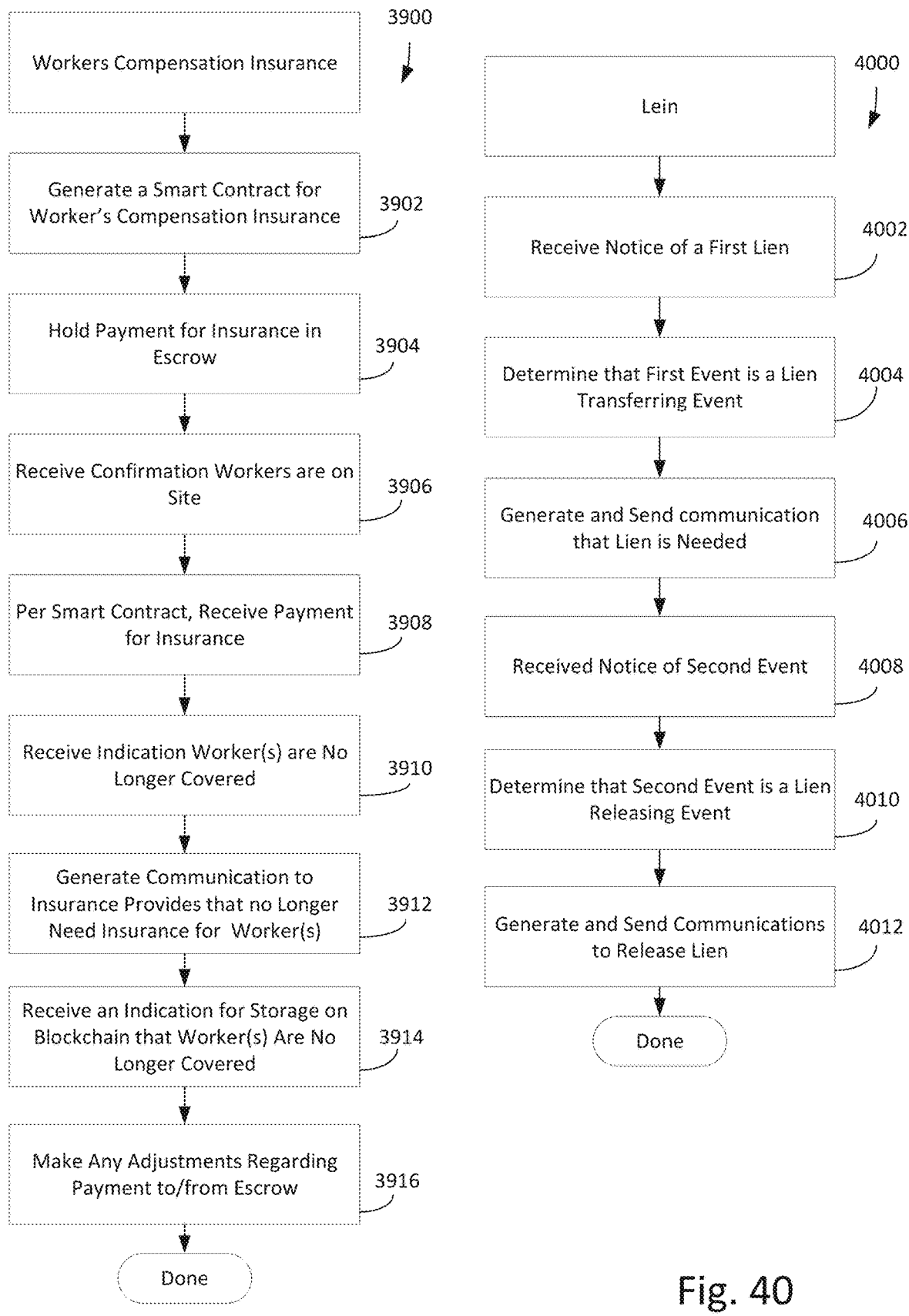

As has been discussed above, worker's compensation insurance may be adjusted as workers are added and removed from the workforce for the project or process with the assistance of smart contracts. FIG. 39 provides a flowchart 3900 of steps performed relative to worker's compensation insurance. A smart contract is provided for worker's compensation insurance 3902 between the insurance provider and the assembler. Payment for the insurance may be held in escrow 3904 and funds may be added/deleted as warranted. When confirmation is received that workers are at the site to work 3906, the insurance is put in place and payment is received 3908 by the insurance provider for the insurance from escrow on behalf of the assembler. When notice is received that a worker or workers is/are no longer to be covered by the insurance 3910, a communication is generated to the insurance provider that no longer need coverage for the worker(s) 3912. An indication is received and hashed to produce a hash value that may be referenced on the blockchain-based persistent storage that the worker is no longer covered by the insurance 3914 and any adjustments in the insurance premiums may be made to the escrow account 3916.

Liens are often used in construction. The exemplary embodiments enable the triggering and releasing of such liens to be automated. FIG. 40 shows a flowchart 4000 of steps that may be performed regarding liens. Initially, notice of a first event is received 4002 at the systems or at a server in a cloud environment. A programmatic determination is made that the event is a lien triggering event 4004. For example, suppose a supply company delivers items to a project location. The supply company may have a lien on the items until payment is received. A communication is generated and sent that a lien is needed 4006. This communication may be sent to the involved parties. In some instances, where the lien is not in place, the communication may be sent to legal counsel or the like to perfect the lien. Notice of a second event may be received 4008. The second event may programmatically be determined to be a lien releasing event 4010. A release can be generated and sent to the proper parties at 4012.

Because of the tracking of assembly progress and the automated scheduling, exemplary embodiments may provide for just in time (JIT) delivery. JIT delivery ensures that items are delivered when needed and are not delivered late causing delays. Moreover, JIT delivery ensures that items are not delivered too early and thus unnecessarily exposed to the elements, be susceptible to theft or occupy needed storage space. FIG. 41 shows a flowchart 4100 of steps performed to realize such JIT delivery scheduling. As has been discussed above, information regarding workflow is stored in storage 4102. The workflow specifies what items are needed and when the items are needed. The exemplary embodiments keep track of how a project is progressing and stores information in storage regarding the progress 4104. Based on this information delivery of items can be scheduled just in time 4106. A communication is generated and sent to prompt the delivery to occur when scheduled 4108.

FIG. 42 shown an exemplary embodiment that support JIT labor where the labor arrives on site when they are needed as shown in a flowchart of steps that may be performed to realize JIT labor. The workflow for the project specifies what quantity of labor is needed and when the labor is needed. The workflow information is stored in storage 4202, as is information regarding the progress of the project 4204. Based on the stored workflow and progress information, labor needs are determined 4206. A communication is generated and sent to prompt the laborers to be scheduled for work on specified dates/times when they are needed 4208.

To pair a material with its virtual representation the system captures events at various points of transition of the material. Pairing the physical material with the virtual representation can include several elements or components. Included in the pairing process can be the physical observation of the physical material and then associate the physical material with a virtual representation so that the physical material is properly associated with the virtual representation. This verification provides trust that the virtual representation is accurately associated with the physical material as a factor rather than simply trusting that the virtual representation is accurate. This system can use manual or automated processes to physically observe the material and associate the material with the virtual representation during various events from raw material to final deliverables. Verification can also use the metadata that is associated with the interaction of physical items by individuals and electronics when the item is created, transported, installed, activated, and destroyed. The metadata that can be captured and placed into immutable storage can provide stakeholders an audit trail of history for their physical asset using a verified paired virtual representation. A similar process as described herein can be used for pairing a biometric identifier with an individual.

For example, when raw material is harvested, a harvesting record can be created that captures the harvesting event and can include metadata concerning the event and verification that the raw material is associated with the harvesting record. For example, a digital image of the raw material can be captured, and the images and its metadata of the image captured can be included in the virtual representation. The capture device and its metadata can also be captured and included in the harvesting record. For example, a sensor having a GPS transponder, camera and transceiver can be used to capture the harvesting event. The metadata of the harvesting event can include date, time, location (e.g., GPS coordinates), harvesting image, harvesting entity, harvesting worker, harvesting equipment and any combination. Once harvested, raw material can be loaded on a transport (e.g., vehicle, plane, ship, and the like). By capturing the harvesting event and verifying that the raw material and the virtual representation are paired, and stored on the persistent storage, the physical material and the virtual representation are paired allowing for reliance upon the digital record to accurately represent the physical material.

By verifiably pairing the physical asset with a virtual presentation, the risk of unintentional or impermissible rehypothecation can be reduced or eliminated. The paired asset can be verified by multiparty chronological metadata streams that can be associated with a physical location. Because verifications using these streams are chronological, altering the information could require alteration of the metadata prior to and after the altered record. Therefore, the altered record would be inconsistent with the associated records potentially both temporally and geographically and an attempt to alter the record would be discovered. The use of a persistent storage further reduces the risk of alterations of records as well as increasing the verification of information. Further, pairing assets associated with the event, involving the asset, interactions with the asset and the associated metadata provide for a substantiated digital asset, reduce, or eliminate risk and improve capital efficiency. Further, the pairing of assets facilitates commerce by allowing electronic transactions with assurances that the virtual representation used in the electronic transaction is paired with the physical asset.

Verification, including verification of an event, can include verifying that the physical material and the virtual representation match and can be accomplished in a variation of methods including interaction with identification elements such as a tag, label, and the like, capturing an image of the material, capturing a video of the material, capturing a tag physically affixed or otherwise associated with the material, human visual inspection, and any combination. Identification of an individual performing or otherwise associated with an event can be captured by identification devices (e.g., cards, tags, RF ID) and biometrics including visual capture (e.g., facial recognition), voice recognition, iris scan, fingerprint, palm print and any combination.

The system can retrieve the harvesting record, receive verification that the raw material delivered to a shipper is the same that was harvested and create a shipping record. A verification that the physical material and the retrieved virtual representation match can be performed using a capture device, worker verification and a combination. The metadata associated with delivering the raw material to the shipper can be captured and included in the shipping record. The shipping record can include information about the shipper and the worker delivering the raw material to the shipper. The shipping record can include information about the destination of the raw material. By capturing the shipping event and verifying that the raw material harvest delivered to the shipper and the virtual representation are paired, and stored on the persistent storage, the physical material and the virtual representation are paired from harvesting the delivery to the shipper allowing for reliance upon the digital record to accurately represent the physical material and its disposition.

The system can retrieve the shipping record, receive verification that the raw material delivered by the shipper to a processor (e.g., manufacturer), is the same that was harvested, shipped, and received. The metadata associated with delivering the raw material to the processor can be captured and included in a delivery record. The delivery record can include information about the shipper, processor, worker and any combination. The delivery record can include information about the processor, location, and other information. By capturing the delivery event and verifying that the raw material harvest delivered to the processor and the virtual representation are paired, and stored on the persistent storage, the physical material and the virtual representation are paired from harvesting the delivery to the processor allowing for reliance upon the digital record to accurately represent the physical material and its disposition.

Once the processor processes the raw material to form a processes material, the system can create a processor record including that the raw material delivered to the processor is integrated into a processed material and is the same raw material that was harvested, shipped, and received. The metadata associated with processing the raw material can be captured and included in a processing record. The processing record can include information about the harvesting, shipping, processor, worker, and any combination. By capturing the processing event and verifying that the raw material harvested delivered to the processor and the virtual representation are paired, and stored on the persistent storage, the physical material and the virtual representation are paired from harvesting to processing allowing for reliance upon the digital record to accurately represent the physical material and its disposition.

Once processed, the processed material can be further shipped to be included as a component in another material. For example, the raw material can be aggregates, rocks, Portland cement and water. The processed material can be concrete. When an article (material) is made from the concrete, the article can be associated with a virtual representation that allows pairing of the article with the raw material and the events through the article process. Therefore, the physical article and the virtual representation are paired from harvesting to article creation allowing for reliance upon the digital record to accurately represent the physical article (material) and its disposition.

Figure 43A:
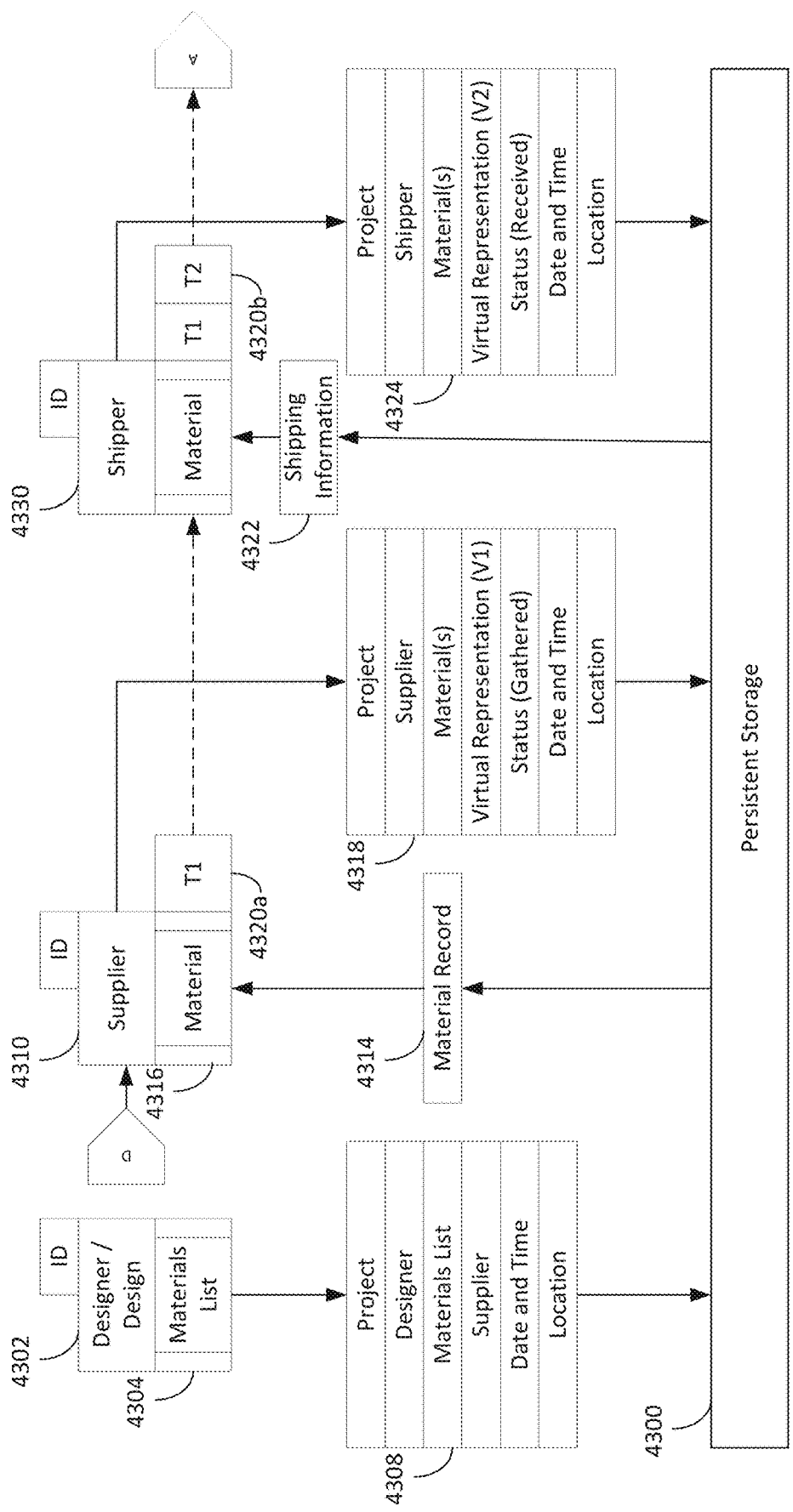
FIGS. 43A-43E shows schematics of aspects of the system.

Referring to FIG. 43A, an exemplary embodiment is shown. The persistent storage 4300 is accessible by a designer using a designer computer system 4302. The designer can have a unique ID associated with it. The designer can create a project design such as a part design, project, process, or other activity. For example, the project can include a design for a vehicle, a consumer product, construction, manufacturing, or other activity. The design can include a material list that will be used for the project. The system can create a designer record 4308 that can include information associated with the project, project location, designer, material list, supplier for one or more materials on the material list, the date and time the design was created or modified and the location where the design was created or modified and other metadata. The design record can be stored on the persistent storage that can be local or remote from the designer.

For example, if the project is a construction project, project location would be the physical location of the construction site. The material list can include a material requirement record which can be generated by a designer as well as integrators, service providers, resellers, and others and can be sent to suppliers or manufacturers so that the identification and cost of the material requirement and task to be performed with the materials are known prior to ordering the materials and finalizing a project plan or process. The material record can be stored on the persistent storage. The material requirement record can include a single component or multiple components. Each component or material in a set of materials can include a warranty that is from the manufacturer, distributor, installer, and any combination. The requirements for a warranty to remain in place can include requirements such as compliance with installation processes, environmental conditions, use of licensed workers, use of qualified and experienced workers and any combination.

A supplier, using a supplier computer system 4310, can select or otherwise acquire the material 4316 identified on the material list from a materials requirement record 4312 or designer record that can be retrieved or otherwise received by the supplier computer system from the persistent storage. The supplier can verify that the material matches the material requirement record, and the system can capture this event. For example, one method of associating the physical material with a virtual representation is using a tag 4320a ($T_1$) placed on the material. The tag is then physically verified to be associated with the material from the material list or the material requirement record. Therefore, the physical material and the virtual representation ($V_1$) are paired by recording this event and associating the physical material, $T_1$, and $V_1$. In one embodiment, the tag can include the following information:

| Description | Digits | Information |
| --- | --- | --- |
| Locations | 19-20 | GPS XX.XXXXXX XXX.XXXXXX |
| User ID | 8 | SSN XXXX + Initials XX + Gender X |
| Date | 10 | XX/XX/XXXX |
| Time | 7 | Zulu XXXX:XX |
| Material | 12 | UPC/Barcode XXXXXXXXXXXX |

A supplier record 4318 can be created and stored on the persistent storage. The capture event can include a unique number and include the supplier ID, date and time, location, material ID, status, and any combination. The material ID can be from an original manufacturer or the supplier. The status can include that the material has been gathered, packaged, ordered, is in stock or on back order, shipping information and any combination. The shipping information can include the origin, destination, shipping instructions, shipper, and any combination.

Figure 43B:
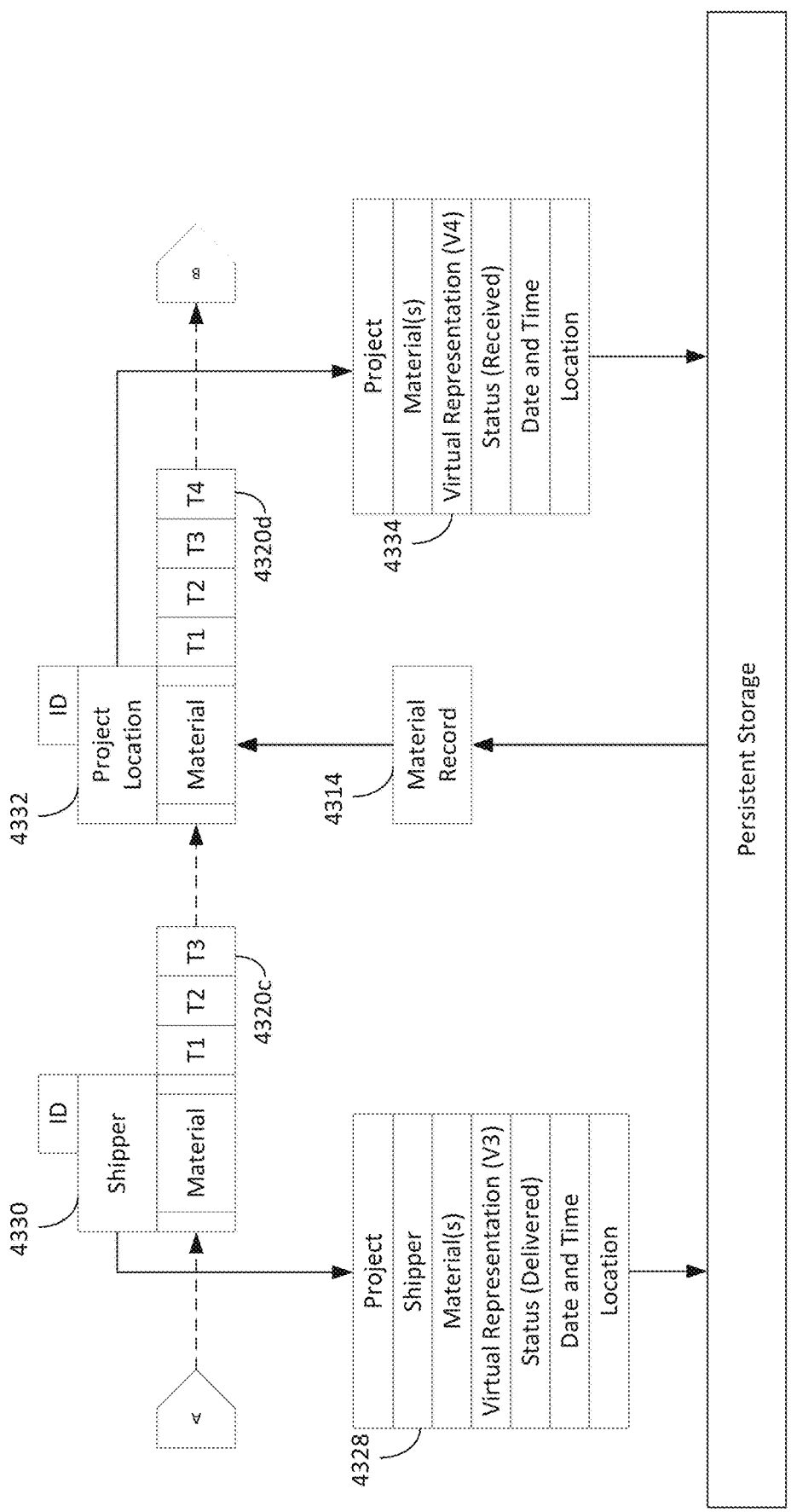

Referring to FIG. 43B, a shipper can retrieve shipping information from the persistent storage 4322 identifying the material location, load, destination, pick time, delivery time, and other information concerning the shipping of the materials. The shipper can verify that the physical materials being retrieved from the supplier match the virtual representation of the supplier record. If the materials are verified, the shipper can physically capture the event, for example, by affixing its tag 4320b ($T_2$) to the materials representing this verification. A supplier shipping pickup record 4324 can be created and stored on the persistent storage. The supplier shipping pickup record can include project, shipper, material, status, date, time, location, and any combination. The mode of transportation of the material can also be tracked and stored on the persistent storage. For example, if the shipper uses a vehicle, the date, time, location and other metadata associated with the vehicle can be gathered along the route and stored on the persistent storage. Verification can be provided using the metadata of the various events. For example, if the date, time, and location of the supplier record is within a certain range of values of the date, time and location of the supplier shipping pickup record, there will be verification that the proper materials were physically transmitted from the supplier to the shipper.

The shipper can deliver the material to the destination such as a project location. When the shipper delivers the materials to the project location, the shipper can capture this event by creating a supplier shipping delivery 4328 record using a shipper computer system 4330. The shipper can verify the event by methods including adding a tag 4320c ($T_3$) representing that the proper materials were delivered to the proper location. The project location computer system 4332 can be used to verify that the materials were properly delivered by retrieving the material record 4314 from the persistent storage and using the record to match the physical materials delivered. In one embodiment, the shipper can use the tags that are part of the virtual representation to match $T_3$ with the material and the information stored on the persistent storage to capture and verify the event. When the material is delivered, the project location can use a project computer system 4332 to retrieve the material record from the persistent storage and match the material delivered with the material record. The project location can add a tag 4320d ($T_4$) to the material to capture this event. The project location can create a project location material received record 4334 that can include the project, material, virtual representation ($V_4$), status, date, time, location, other metadata, and any combination. The shipper, worker at the project location, or both can physically inspect the material and verify that it is matches the virtual representation stored on the persistent storage. This verification can be included in the information that is stored on the persistent storage by the shipper and a worker or system at the project location.

Figure 43C:
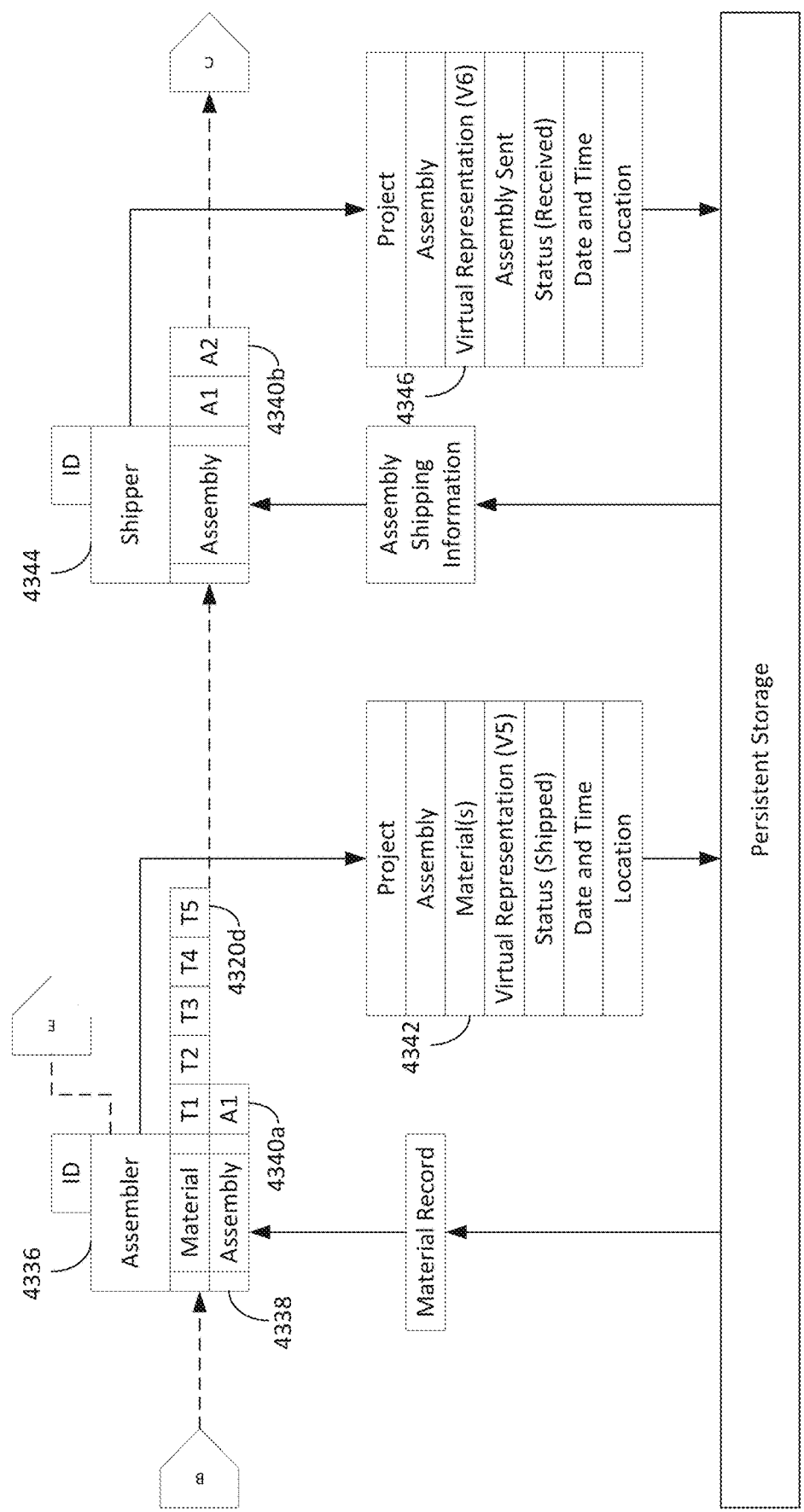

Referring to FIG. 43C, the project location can be an assembler, or the assembler can be at a separate location from the project. For example, in the manufacturing of a vehicle, the project location can be the assembly line for the vehicle and multiple assembly locations can be involved. The main assembly line can be the project location and the assembler can be a component or sub-component of the manufacturing process. This system can be used for the project, or sub-project that are included in the overall project. Further a sub-project can be treated as a project as discussed herein.

An assembler computer system 4336 can be used to retrieve the material record from the persistent storage. The material record can be used to match the materials delivered to the assembler to verify that the proper materials were received by the assembler. The assembler can add tag 4320d ($T_5$) to the material, or use other verification methods described herein, to capture the event. The assembler can also capture the material used and the assembly 4338 by adding a tag 4340a ($A_1$) to the assembly. An assembler record 4342 can be created and stored on the persistent storage. The assembler record can include the project, assembly description and other information, assembler, material(s) used, virtual representation, shipping information date, time, location of the assembly, other metadata, and any combination.

Once completed, the assembly may need to be delivered to another location. The assembler record can include shipping information, or an assembly shipping record can be created and stored on the persistent record. If the assembly needs to be delivered, a second shipper can use a second shipper computer system 4344 to retrieve the shipping record, assembler record or other shipping information that is used to identify the origin, locations, assembly, pick up time, delivery time and other information associated with the transportation of the assembly from one location to another. The assembly can be received by the second shipper and the second shipper can capture the event such as with a tag 4340b ($A_2$) to the assembly representing that the assembly has been verified by the second shipper as properly provided and received by the shipper. A second shipper pick up record 4346 can be created and stored on the persistent storage.

Figure 43D:
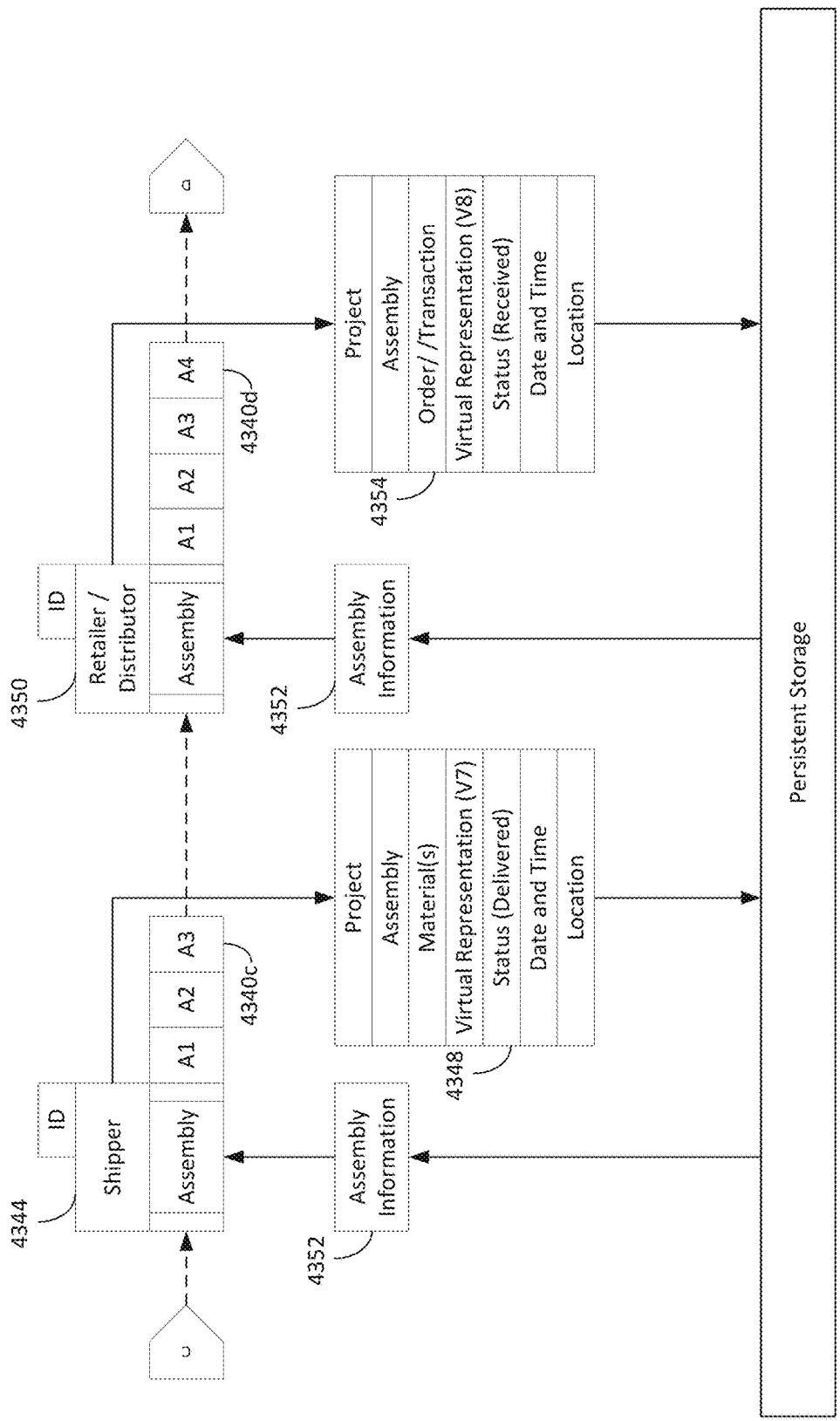

Referring to FIG. 43D, the second shipper can deliver the assembly to a retailer, distributor, or customer. The assembly can be a component to be further used or a final product. When the second shipper delivers the assembly to a retailer or distributor, the second shipper can create a second shipper delivery record 4348 using a second shipper computer system 4344. The second shipper can capture the event such as using a tag 4340c ($A_3$) representing that the proper assembly was delivered to the proper location. The second shipper can use the verifications that are part of the virtual representation to match $A_3$ with the material and the information stored on the persistent storage.

The retailer or distributor computer system 4350 can be used to verify that the materials were properly delivered by retrieving the assembly record 4352 or second shipper record 4348 from the persistent storage and using the record to match the physical assembly delivered. The retailer or distributor can capture the event and can add a tag 4340d ($A_4$) representing that the proper assembly was received at the proper location. A retailer distributor record 4354 can be created and stored on the persistent storage.

Figure 43E:
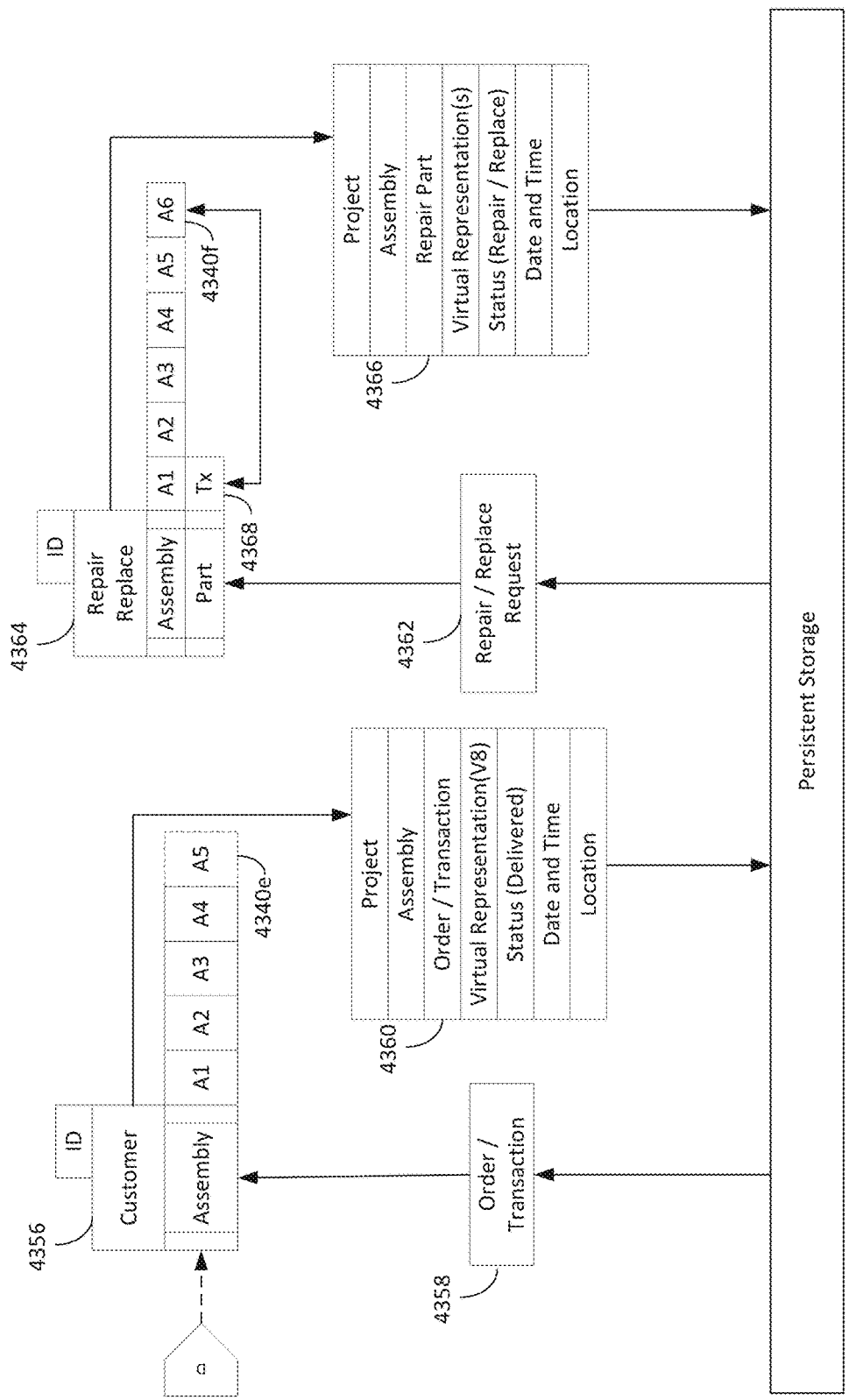

Referring to FIG. 43E, a customer can receive the assembly as using a customer computer system 4356 to retrieve or otherwise receive an order record 4358 from the persistent storage or other system requesting that a customer receive the assembly. The customer can be shipped the assembly using the system as described herein with a shipper performing the steps and the system performing the steps associated with the shipper and second shipper above. A third shipper can create a third shipper pickup and delivery record that can be stored on the persistent storage verifying that the assembly was properly provided from the realtor or distributer to the customer. The customer may capture the event and can add a tag 4340e ($A_5$) to the assembly that can be associated with the virtual representation ($V_8$). A customer record 4360 can be stored on the persistent storage.

Using this system, the customer can be assured that the assembly was independently verified and authenticated from the design to the delivery to the customer and that the virtual representation of the assembly and its components (e.g., materials) are paired.

In one embodiment, a repair request 4362 can be created and stored on the persistent server. The repair request can be associated with the assembly and retrieved by a repair computer system 4364. The repair company can receive a part using the system described herein, perform a repair or replacement action, and capture the event such as by using a tag 4340f ($A_6$) to the assembly indicating that the assembly has had a part repaired or replaced. The repair part can also have a preexisting tag from the use of the system herein and the repair company can capture the event such as by using a tag 4368 ($T_x$). A repair record 4366 can be created and stored on the persistent storage.

The system described herein can pair the physical material and/or assembly with a virtual representation. Failure to pair the physical material or assembly with the virtual representation can negatively impact areas such as regulatory requirements. Regulatory requirements are a set of rules that can specify the standards for a project. Regulatory requirements impact designs, materials, worker's license and experience the project and process. For example, a building code may require that construction materials be installed in accordance with manufacturer's specifications and warranty regulations. Failure to follow the building codes can result in the project not being approved, errors, lack of customer satisfaction, insurance claims, injury, litigation, and other negative ramifications. Tracking, management, and verification of materials to ensure compliance with regulatory requirements and proper installation according to applicable specifications is an important aspect to many projects and processes. Tracking and record keeping during the project or process can be beneficial, as it can be difficult to perform these tasks after project or process completion because the materials can be hidden from view or otherwise inaccessible. For example, electrical wiring in a project or process can be hidden behind walls and ceilings once the project is complete.

Systems at multiple locations may be interconnected using image capture devices, RFID, QR codes, barcodes, biometric scanners, still cameras, video cameras, and the like to identify individuals or machines that are performing verifications during the process. Further, multiple individuals or machines are performing verifications so that there is not a reliance upon any one entity for verifications. The processing of capturing data, including images, from the multiple systems at multiple locations can be used to improve the verification of proper materials and assemblies as well as to pair the physical items with the virtual representation.

Verification of processes, inspections, completions and deliveries with adjustments and notifications (manual and automated) with confirmation would ensure increased productivity, especially if accessible in real time at the location. Real time processes and procedures planned with corresponding training and manuals would improve quality control and efficiency. This has been a long felt need in the prior art that has not been satisfied with a controller that is uniquely associated with an asset location.

Automated verification of quantities, quality, and correct product deliveries along with after delivery tracking of materials with accountability is seldom used. Designated delivery areas with geofenced control and tracking of materials once delivered would help prevent loss. Confirmation of products integrated at the asset location provides transparency regarding sourcing, warranties, as well as future reference during the structure and individual product's life of use.

By using the various tags and virtual representations, each entity in the process can verify that the physical materials match any record the precedes that entity.

This process can include internal and external individuals and machines for performing inspections (e.g., verifications). For example, the system can receive a set of internal inspection information entered into the system from an internal inspector representing an internal physical inspection of the project, material or assembly. As the items travel, an internal inspector can provide inspection information representing the stages of the project. The system can also receive a set of external inspection information from an external inspector and an external inspection computer device representing a third-party physical inspection of the project at predetermined stages of the project. Based upon the internal inspection, external inspection or both, an inspection record can be created and stored on the persistent storage.

Figure 44:
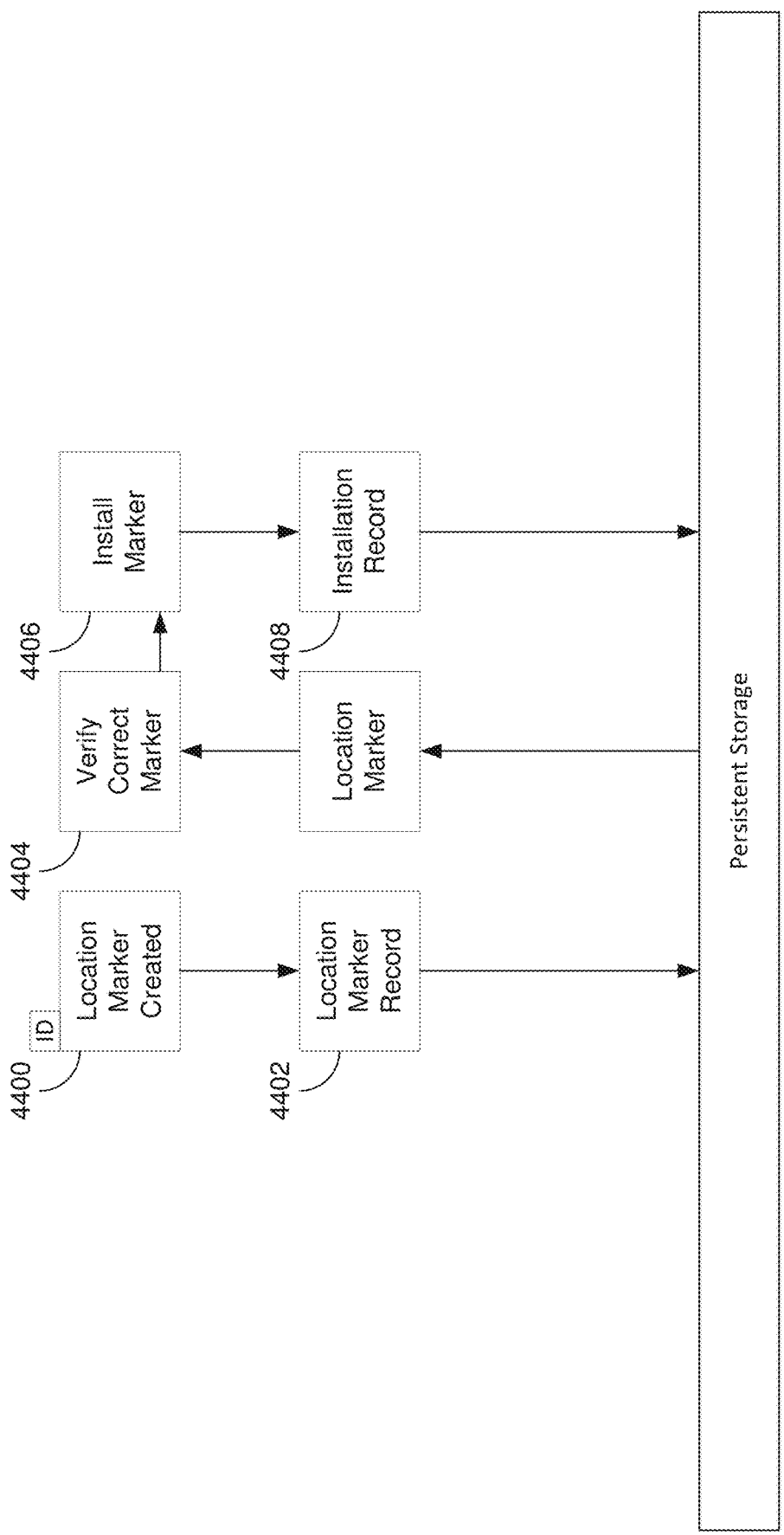
FIG. 44 shows schematics of aspects of the system.

Referring to FIG. 44, a location marker 4400 used to uniquely identify a location such as a project location and can include a construction site, business, distributor, retail or wholesale location, warehouse, asset location, or other physical location. The location marker can be a barcode, RF ID, placard, sign, plaque, QR code, or other symbolic, alphanumeric, digital, or electronic identifier. When creating the location marker, a location marker record 4402 can be created that includes the location marker identification information, creation date, maker, manufacturing location and other information that can be stored on the persistent storage. The installed information can retrieve the location marker record and match the retrieved information with the physical location marker to verify that the correct location marker is being installed at 4404. The installed can physically install the location marker and using a GPS enabled device, read the location marker and create a location marker installation record 4408. The installation can be paired with the physical location marker and/or the physical location of the project. The metadata from the GPS enabled device can be included in a location marker installation record that can also include installer information, date, time, location marker information and physical location information and can be stored on the persistent storage. Therefore, the physical location marker is verified to be paired with the project location and a virtual representation of the location market and project location.

Subsequently, an individual can scan the location marker, which is paired with the physical location, and associate the physical location with material, action, inspection, transaction, of other information or activity by using the location marker. Therefore, the material, action, inspection, transaction, of other information or activity can be paired with the project location. For example, when materials are delivered to the project location, the location marker is read, the material's identification is read and the two are verified to be in the same location. A delivery record that can include the location marker information is created and stored thereby paring the physical materials and action with the project location and virtual representation.

The verified pairing described herein can also be used to verifiable pair physical assets with installation instructions, storage instructions, warranties, ownership, service, maintenance, and any combination thereof.

What is claimed is:

1. A computerized system for verifiably pairing a physical asset with a digital representation comprising:
    a computer system disposed at a physical location and in communication with a persistent storage;
    a set of non-transitory computer readable instructions included in the computer system adapted for:
        retrieving, from the persistent storage, a design record having a material list including a material and created by a designer computer system wherein the designer computer system is adapted to store the design record on the persistent storage,
        retrieving, from the persistent storage, a supplier record created by a supplier computer system in communications with the persistent storage and according to a first verification representing receipt of the material by the supplier paired with a first virtual representation stored on the persistent storage,
        retrieving, from the persistent storage, a shipping record created by a shipper computer system in communications with the persistent storage and according to a second verification representing that the material is provided to the shipper, delivered to the physical location, and paired with a second virtual representation stored on the persistent storage, and
        creating a material receipt record including a third verification representing that the material is received at the location and is the same material that was designated by the designer, provided by the supplier, and received by the shipper is present at the physical location.

2. The computerized system of claim 1 including:
    a location marker associated with the physical location; and,
    the computer system is uniquely paired with the physical location using the location marker.

3. The computerized system of claim 2 including a sensor in communications with the computer system wherein the first verification utilizes the sensor and the location marker.

4. The computerized system of claim 2 wherein the supplier record is created according to a physical verification of a first tag affixed to the material and the physical location marker.

5. The computerized system of claim 1 wherein the second verification includes verifying that a second tag is affixed to the material.

6. The computerized system of claim 5 wherein the second verification includes verifying that a second tag is affixed to the material using a sensor in communications with the computer system.

7. The computerized system of claim 1 wherein the supplier record is created according to a physical verification of a first tag affixed to the material.

8. The computerized system of claim 1 wherein the supplier record includes metadata taken from the group consisting of date, time, location, worker, environmental condition, and any combination thereof.

9. The computerized system of claim 1 wherein the shipping record is created according to a physical verification performed by an individual that material is consistent with the second virtual representation.

10. The computerized system of claim 1 wherein the physical location is the location associated with an entity taken from the group consisting of an assembler, a retailer, a wholesaler, an installer, a builder, a manufacturer, a service provider, a customer, and any combination thereof.

11. The computerized system of claim 1 creating a distribution record representing that the material received at the physical location is the same material that was designated in the designer, provided by the supplier, retrieved from the supplier by the shipper, delivered to the physical location by the shipper and delivered to a distributor.

12. The computerized system of claim 11 creating a customer record representing that the material received at the physical location is the same material that was designated in the designer, provided by the supplier, retrieve from the supplier by the shipper, delivered to the distributor by the shipper and delivered to a customer.

13. The computerized system of claim 1 wherein the set of non-transitory computer readable instructions include instructions for
creating a repair request,
storing the repair request on the persistent storage, and
creating a repair record according to a replacement part and associating the replacement part with a replacement virtual representation and storing the repair record on the persistent storage.

14. A computerized system for pairing a physical asset with a digital representation comprising:
a computer system disposed at a physical location and in communications with a persistent storage;
a sensor in communications with the computer system;
a set of non-transitory computer readable instructions included in the computer system adapted for:
retrieving, from the persistent storage, a design record having a material list including a selected material and created with a design computer system wherein the designer computer system is in communications with the persistent storage,
retrieving, from the persistent storage, a supplier record created by a supplier computer system in communications with the persistent storage and according to the design record created by a designer computer system and according to a first verification representing receipt of the selected material by the supplier associated with a first virtual representation stored on the persistent storage,
retrieving, from the persistent storage, a shipping record created by a shipper computer system in communications with the persistent storage and according to the supplier record created by a supplier and according to a second verification representing that the selected material is provided to the shipper and associated with a second virtual representation stored on the persistent storage, and
creating an assembly record representing a third verification that the selected material received at the physical location is the same material as the selected material, was provided by the supplier, delivered by the shipper to the assembler by the shipper, and included in an assembly.

15. A computerized system of claim 14 wherein:
the physical location is a first location;
the shipping record is a first shipping record;
the shipper is a first shipper; and,
the set of non-transitory computer readable instructions include instructions for creating a second shipping record requesting shipping of the assemble to a second location wherein the second shipping record includes a fourth verification.

16. The computerized system of claim 15 wherein the fourth verification utilizes the sensor.

17. The computerized system of claim 15 including:
a location marker associated with the physical location; and,
the computer system is uniquely associated with the physical location using the location marker.

18. The computerized system of claim 15 wherein the computer system is contained in a kiosk affixed to the physical location.

19. A computerized system for verifiably pairing a physical asset with a digital representation comprising:
a computer system uniquely associated with a physical location;
a location marker disposed at the physical location;
a sensor in communications with the computer system;
a set of non-transitory computer readable instructions included in the computer system adapted for:
retrieving, from a persistent storage, a design record created by a designer computer system in communications with the persistent storage and having a material,
retrieving, from the persistent storage, a supplier record created by a supplier computer system in communications with the persistent storage and according to the design record created by a designer computer system in communications with the persistent storage and according to a first verification representing receipt of the material by the supplier associated with a first virtual representation stored on the persistent storage,
retrieving, from the persistent storage, a shipping record created by a shipper computer system in communications with the persistent storage according to the supplier record created by a supplier and according to a second verification representing that the material is provided to the shipper and associated with a second virtual representation stored on the persistent storage, and,
creating a material receipt record having a third verification representing that the material received at the location is the same material designated in the designer, provided by the supplier, retrieved from the supplier by the shipper and delivered to the location by the shipper.

20. The computerized system of claim 19 wherein the design record includes metadata taken from the group consisting of date, time, geographic location, designer, environmental condition, and any combination thereof.

21. The computerized system of claim 19 wherein the supplier record includes metadata taken from the group consisting of date, time, geographic location, supplier, environmental condition, and any combination thereof.

22. The computerized system of claim 19 wherein the shipping record includes metadata taken from the group consisting of date, time, geographic location, shipper, environmental condition, and any combination thereof.

23. The computerized system of claim 19 wherein the material receipt record includes metadata taken from the group consisting of date, time, geographic location, receiver, environmental condition, and any combination thereof.

* * * * *